US012570638B2

(12) United States Patent
Bartolozzi et al.

(10) Patent No.: US 12,570,638 B2
(45) Date of Patent: Mar. 10, 2026

(54) FUSED IMIDAZOLE DERIVATIVES AS AHR ANTAGONISTS

(71) Applicant: Sail Biomedicines, Inc., Cambridge, MA (US)

(72) Inventors: Alessandra Bartolozzi, Gladwyne, PA (US); John Robert Proudfoot, Newtown, CT (US); Timothy Briggs, Waltham, MA (US); John Mancuso, Saint-Marthe-sur-le-Lac (CA); Maxence Bos, Montreal (CA); Vu Linh Ly, Montreal (CA); Anna Blois, Chestnut Hill, MA (US); Bernard Lanter, Somerville, MA (US); Steven John Taylor, Winchester, MA (US); Leonard Buckbinder, East Greenwich, RI (US)

(73) Assignee: Sail Biomedicines, Inc., Cambridge, MA (US)

( * ) Notice: Subject to any disclaimer, the term of this patent is extended or adjusted under 35 U.S.C. 154(b) by 562 days.

(21) Appl. No.: 17/999,254

(22) PCT Filed: May 19, 2021

(86) PCT No.: PCT/US2021/033078
§ 371 (c)(1),
(2) Date: Nov. 18, 2022

(87) PCT Pub. No.: WO2021/236717
PCT Pub. Date: Nov. 25, 2021

(65) Prior Publication Data

US 2023/0331705 A1 Oct. 19, 2023

Related U.S. Application Data

(60) Provisional application No. 63/027,934, filed on May 20, 2020.

(51) Int. Cl.

| | |
|---|---|
| ***C07D 403/12*** | (2006.01) |
| ***A61K 45/06*** | (2006.01) |
| ***A61P 35/04*** | (2006.01) |
| ***C07D 235/18*** | (2006.01) |

(52) U.S. Cl.
CPC ............ *C07D 403/12* (2013.01); *A61K 45/06* (2013.01); *A61P 35/04* (2018.01); *C07D 235/18* (2013.01)

(58) Field of Classification Search
None
See application file for complete search history.

(56) References Cited

U.S. PATENT DOCUMENTS

| | | | |
|---|---|---|---|
| 3,646,049 A * | 2/1972 | Hoff et al. | C07H 19/052 548/134 |
| 10,570,138 B2 | 2/2020 | Castro et al. | |
| 10,696,650 B2 | 6/2020 | Castro et al. | |
| 11,040,035 B2 | 6/2021 | Schmees et al. | |
| 11,304,946 B2 | 4/2022 | Lefranc et al. | |
| 11,459,312 B2 | 10/2022 | Zorn et al. | |
| 2005/0288311 A1 | 12/2005 | Rault et al. | |
| 2012/0295904 A1 | 11/2012 | Zhi et al. | |
| 2020/0283395 A1 | 9/2020 | Lefranc et al. | |
| 2021/0017153 A1 | 1/2021 | Castro et al. | |
| 2022/0195533 A1 | 6/2022 | Opitz et al. | |
| 2022/0233513 A1 | 7/2022 | Li et al. | |
| 2023/0121195 A1 | 4/2023 | Gutcher et al. | |
| 2023/0234967 A1 | 7/2023 | Bartolozzi et al. | |

FOREIGN PATENT DOCUMENTS

| | | |
|---|---|---|
| CN | 101547922 A | 9/2009 |
| CN | 115443276 A | 12/2022 |
| EP | 3713923 A1 | 9/2020 |
| EP | 3974422 A1 | 3/2022 |
| WO | 2004/077058 A1 | 9/2004 |
| WO | 200841118 A2 | 4/2008 |
| WO | 2010/008843 A1 | 1/2010 |
| WO | 2010/008847 A2 | 1/2010 |
| WO | 2010/100144 A1 | 9/2010 |
| WO | 2010/144909 A1 | 12/2010 |
| WO | 2016/046530 A1 | 3/2016 |
| WO | 2017/202816 A1 | 11/2017 |
| WO | 2018/141857 A1 | 8/2018 |
| WO | 2018/146010 A1 | 8/2018 |
| WO | 2018/195397 A2 | 10/2018 |
| WO | 2019/036657 A1 | 2/2019 |
| WO | 2019/101643 A1 | 5/2019 |

(Continued)

OTHER PUBLICATIONS

Wright et. al. "The Chemistry of the Benzimidazoles" Chem. Rev. 1951, 48, 397-541. DOI: 10.1021/cr60151a002. Only pp. 397-401 Attached. (Year: 1951).*
Li et. al. "Aryl Hydrocarbon Receptor Signaling Cell-intrinsically Inhibits Intestinal Group 2 Innate Lymphoid Cell Function" Immunity. 2018, 49, 5, 915-928 DOI:10.1016/j.immuni.2018.09.015. (Year: 2018).*
Roberts et. al. "Characterization of the Ah Receptor Mediating Aryl Hydrocarbon Hydroxylase Induction in the Human Liver Cell Line Hep GZ" Archives of Biochemistry and Biophysics, 1990, 276, 2, 442-450. DOI: 10.1016/0003-9861(90)90743-1 (Year: 1990).*

(Continued)

*Primary Examiner* — Jennifer A Berrios
*Assistant Examiner* — Sophia Reilly
(74) *Attorney, Agent, or Firm* — McNeill PLLC

(57) ABSTRACT

The present disclosure relates to compounds of formulae (I)-(VI) and pharmaceutically acceptable salts thereof, pharmaceutical compositions comprising the same, methods of preparing the same, intermediate compounds useful for preparing the same, and methods for treating or prophylaxis of diseases, in particular cancer or conditions with dysregulated immune responses or other disorders associated with aberrant AHR signaling.

20 Claims, No Drawings

(56) References Cited

FOREIGN PATENT DOCUMENTS

| | | | |
|---|---|---|---|
| WO | 2019/156987 | A1 | 8/2019 |
| WO | 2019/178542 | A1 | 9/2019 |
| WO | 2020/021024 | A1 | 1/2020 |
| WO | 2020/051207 | A2 | 3/2020 |
| WO | 2020/081636 | A1 | 4/2020 |
| WO | 2020/233641 | A1 | 11/2020 |
| WO | 2021/028382 | A1 | 2/2021 |
| WO | 2021/102288 | A1 | 5/2021 |
| WO | 2021/108469 | A1 | 6/2021 |
| WO | 2021/108528 | A1 | 6/2021 |
| WO | 2021/122434 | A1 | 6/2021 |
| WO | 2021/127301 | A1 | 6/2021 |
| WO | 2021/127302 | A1 | 6/2021 |
| WO | 2021/142180 | A1 | 7/2021 |
| WO | 2021/210970 | A1 | 10/2021 |
| WO | 2021/236717 | A1 | 11/2021 |
| WO | 2021/242955 | A1 | 12/2021 |
| WO | 2022/029063 | A1 | 2/2022 |
| WO | 2022/081649 | A1 | 4/2022 |
| WO | 2022/094567 | A1 | 5/2022 |
| WO | 2022/133480 | A1 | 6/2022 |

OTHER PUBLICATIONS

Chen, et al. "IDO, TDO, and AHR overexpression is associated with poor outcome in diffuse large B-cell lymphoma patients in the rituximab era", Medicine (Baltimore), May 22, 2020; 99(21), 8 pages.
International Search Report and Written Opinion received for PCT Patent Application No. PCT/US2021/034413, mailed on Oct. 14, 2021, 19 pages.
International Search Report issued for PCT Application No. PCT/US2020/061548 dated Feb. 17, 2021 (4 pages).
Written Opinion for International Application No. PCT/US2020/061548 dated Feb. 17, 2021, 7 pages.
Adis Insight, "BAY 218" Drug Profile; Bayer, Last Updated: May 3, 2019; 9 pages.
Adis Insight, "BAY 2416964" Drug Profile; Bayer, Last Updated: Oct. 2, 2021; 12 pages.
Adis Insight, "HP 163" Drug Profile; Hercules Pharmaceuticals, Last Updated: Sep. 21, 2020; 10 pages.
Adis Insight, "IK 175" Drug Profile; Ikena Oncology, Last Updated: Aug. 20, 2021; 18 pages.
Adis Insight, "IK 175" Drug Profile; Ikena Oncology, Last Updated: May 6, 2022; 14 pages.
Adis Insight, "Research programme: immuno-oncology therapies—JAGUAHR Therapeutics," Drug Profile; JAGUAHR Therapeutics, Last Updated: Jun. 24, 2021; 8 pages.
Aggen, D.H. et al., "(661) Initial Results from a Phase 1a/b Study of IK-175, an Oral AHR Inhibitor, as Single Agent and in Combination with Nivolumab in Patients with Advanced Solid Tumors and Urothelial Cancer," Ikena Oncology, Poster, Nov. 7, 2022.
Andersson, P. et al., "A constitutively active dioxin/aryl hydrocarbon receptor induces stomach tumors," PNAS, vol. 99; No. 15; 9990-9995 (2002).
Antonia, S.J. et al., "Durvalumab after Chemoradiotherapy in Stage III Non-Small-Cell Lung Cancer," N Engl J Med, vol. 377; No. 20; 1919-1929 (2017).
Bayer Pharmaceuticals, " BAY 2416964: The first Aryl Hydrocarbon Receptor (AhR) inhibitor to enter phase I clinical development as a novel cancer immunotherapy," Photograph of Powerpoint Slide 19, 1 Page, Presented at AACR Virtual Annual Meeting I 2020 (Apr. 27, 2020).
Bayer Pharmaceuticals, "BAY 2416964 Is a Highly Selective AhR Inhibitor," Powerpoint Slide, 1 Page (2020).
Bayer Pharmaceuticals, "Identification of BAY-218, a potent and selective small-molecule AhR inhibitor, as a new modality to counteract tumor immunosuppression," Powerpoint Slide 10, 1 Page, Presented at AACR Annual Meeting 2019 (Apr. 2, 2019).
Bui, L. et al., "Nedd9/Hef1/Cas-L mediates the effects of environmental pollutants on cell migration and plasticity," Oncogene, vol. 28; 3642-3651 (2009).
Campesato, L.F. et al., "Blockade of the AHR restricts a Treg-macrophage suppressive axis induced by L-Kynurenine," Nature Communications, vol. 11; 4011; 11 pages (2020).
Campesato, L.F. et al., "Blockade of the AHR restricts a Treg-macrophage suppressive axis induced by L-Kynurenine," Nature Communications, vol. 11; 4011; Reporting Summary (2020).
Campesato, L.F. et al., "Blockade of the AHR restricts a Treg-macrophage suppressive axis induced by L-Kynurenine," Nature Communications, vol. 11; 4011; Supplementary Data (2020).
Cella, D. et al., "Patient-reported outcomes of patients with advanced renal cell carcinoma treated with nivolumab plus ipilimumab versus sunitinib (CheckMate 214): a randomised, phase 3 trial," Lancet Oncol., vol. 20; No. 2; 297-310 (2019).
Chamoto et al., "Role of PD-1 in Immunity and Diseases," Curr Top Microbiol Immunol., 2017, 410, 75-97.
Das, S. and Johnson, D.B., "Immune-related adverse events and anti-tumor efficacy of immune checkpoint inhibitors," Journal of ImmunoTherapy of Cancer, vol. 7; 306; 11 Pages (2019).
Di Meglio, P. et al., "Activation of the Aryl Hydrocarbon Receptor Dampens the Severity of Inflammatory Skin Conditions," Immunity, vol. 40; 989-1001 (2014).
Di Meglio, P. et al., "Activation of the Aryl Hydrocarbon Receptor Dampens the Severity of Inflammatory Skin Conditions," Immunity, vol. 40; 989-1001; Supplemental Information (2014).
Dieterich, W. et al., "Microbiota in the Gastrointestinal Tract," Med. Sci., vol. 6; No. 4; 116; 15 Pages (2018).
Dietrich, C. and Kaina, B., "The aryl hydrocarbon receptor (AhR) in the regulation of cell-cell contract and tumor growth," Carcinogenesis, vol. 31; No. 8; 1319-1328 (2010).
Dinatale, B.C. et al., "Kynurenic Acid is a Potent Endogenous Aryl Hydrocarbon Receptor Ligand that Synergistically Induces Interleukin-6 in the Presence of Inflammatory Signaling," Toxicol. Sci, vol. 115; No. 1; 89-97 (2010).
Donaldson, G.P. et al., "Gut biogeography of the bacterial microbiota," Nat Rev Microbiol, vol. 14; No. 1; 20-32 (2016).
Esser, C. et al., "The aryl hydrocarbon receptor in immunity," Trends Immunol., 2009, 30, 447-454.
Fallarino, F. et al., "T cell apoptosis by tryptophan catabolism," Cell Death Differ, 2002, 9(10), 1069-1077.
Ferns, D.M. et al., "Indoleamine-2,3-dioxygenase (IDO) metabolic activity is detrimental for cervical cancer patient survival," Oncoimmunology, 2015, 4(2); e981457-2.
Fife, B.T. and Bluestone, J.A., "Control of peripheral T-cell tolerance and autoimmunity via the CTLA-4 and PD-1 pathways," Immunol Rev., 2008, 224, 166-182.
Funatake et al., "Cutting Edge: Activation of the Aryl Hydrocarbon Receptor by 2,3,7,8-Tetrachlorodibenzo-p-dioxin Generates a Population of CD4+CD25+ Cells with Characteristics of Regulatory T Cells," J Immunol, 2005, 175(7), 4184-4188.
G. Kulkarni Ravindra et al: "Synthesis, p38 kinase inhibitory and anti-inflammatory activity of new substituted benzimidazole derivatives." Medicinal Chemistry vol. 9. No. 1 (2013): pp. 91-99.
Gandhi, L. et al., "Pembrolizumab plus Chemotherapy in Metastatic Non-Small-Cell Lung Cancer," N Engl J Med, 2018, 378(22) 2078-2092.
Gargaro, M. et al., "Indoleamine 2,3-dioxygenase 1 activation in mature cDC1 promotes tolerogenic education of inflammatory cDC2 via metabolic communication," Immunity, vol. 55; 1032-1050 (2022).
Gopalakrishnan et al., "Gut microbiome modulates response to anti-PD-1 immunotherapy in melanoma patients," Science, 2018, 359(6371), 97-103.
Gramatzki, D. et al., "Aryl hydrocarbon receptor inhibition downregulates the TGF-B/Smad pathway in human glioblastoma cells," Oncogene, 2009, 28, 28, 2593-2605.
Gutcher Ilona et al: "Blocking tumor-associated immune suppression with BAY-218, a novel, selective aryl hydrocarbon receptor (AhR) inhibitor." Cancer Research 79.13_Supplement (2019): 1288-1288.

(56) References Cited

OTHER PUBLICATIONS

Hankinson et al., "Role of coactivators in transcriptional activation by the aryl hydrocarbon receptor," Arch Biochem Biophys, 2005, 433(2), 379-386.
Hezaveh, K. et al., "Tryptophan-derived microbial metabolites activate the aryl hydrocarbon receptor in tumor-associated macrophages to suppress anti-tumor immunity," Immunity, vol. 55; 324-340 (2022).
Hidaka, T. et al., "Aryl Hydrocarbon Receptor Modulates Carcinogenesis and Maintenance of Skin Cancers," Frontiers in Medicine, vol. 6; Article 194; 7 pages (2019).
Hoffman, T., "Discovery of Small Molecule Aryl Hydrocarbon Receptor (AhR) Antagonists for Cancer Immunotherapy," Discovery on Target, Boston Massachusetts, Presentation; 30 pages (2019).
Horsman, M.R. et al., "Tumors Resistant to Checkpoint Inhibitors Can Become Sensitive after Treatment with Vascular Disrupting Agents," Int J Mol Sci, 2020, 21(13). 4778.
I. R. Gelling et al: "Pyridopyrimidines. Part V. Syntheses and properties of pyrido [3, 4-d]-pyrimidin-4 (3 H)-ones and-pyrimidine-2, 4-(1 H, 3 H)-diones." Journal of the Chemical Society C: Organic vol. 6 (1969): pp. 931-934.
Ikena Oncology. (2022) Form 10-K 2021. U.S. Securities and Exchange Commission.
Ikena Oncology. (2022) Form 8-K Apr. 6, 2022. U.S. Securities and Exchange Commission.
International Search Report and Written Opinion received for PCT Patent Application No. PCT/US2021/033078, mailed on Sep. 21, 2021, 17 pages.
Karayama M et al: "Comprehensive assessment of multiple tryptophan metabolites as potential biomarkers for immune checkpoint inhibitors in patients with non-small cell lung cancer." Clinical and Translational Oncology 2, 3 (2021): pp. 418-423.
Kenison, J.E. et al., "The aryl hydrocarbon receptor suppresses immunity to oral squamous cell carcinoma through immune checkpoint regulation," PNAS, vol. 118; No. 19; e2012692118; 12 pages (2021).
Kim, N. et al., "Discovery of novel HCV polymerase inhibitors using pharmacophore-based virtual screening," Bioorganic & medicinal chemistry letters vol. 21. No. 11 (2011): pp. 3329-3334.
Kim, S. et al., "Novel Compound 2-Methyl-2H-pyrazole-3-carboxylic Acid (2-methyl-4-o-tolylazo-phenyl)-amide (CH-223191) Prevents 2,3,7,8-TCDD-Induced Toxicity by Antagonizing the Aryl Hydrocarbon Receptor," Molecular Pharmacology, vol. 69; No. 6; 1871-1878 (2006).
Lin, L. and Zhang, J., "Role of intestinal microbiota and metabolites on gut homeostasis and human diseases," BMC Immunol., 2017, 18(1), 2.
Liu, X. et al., "Selective inhibition of IDO1 effectively regulates mediators of antitumor immunity," Blood, vol. 115; No. 17; 3520-3530 (2010).
Liu, X. et al., "The serratus anterior plan block for analgesia after thoracic surgery," Medicine, vol. 99; No. 21; 8 pages (2020).
Matson et al., "The commensal microbiome is associated with anti-PD-1 efficacy in metastatic melanoma patients," Science, 2018, 359(6371) 104-108.
McGovern, K. et al., "Discovery and characterization of a novel aryl hydrocarbon receptor inhibitor, IK-175, and its inhibitory activity on tumor immune suppression," Mol Cancer Ther (2022) 21 (8): 1261-1272.
McKean, M.A. et al., "A Phase 1a/b Study of IK-175, an Oral AHR Inhibitor, Alone and in Combination with Nivolumab in Patients with Locally Advanced or Metastatic Solid Tumors and Urothelial Carcinoma," Ikena Oncology, SITC 36th Annual Meeting, Poster #550, Nov. 13, 2021.
Metz, R. et al., "Novel Tryptophan Catabolic Enzyme IDO2 Is the Preferred Biochemical Target of the Antitumor Indoleamine 2,3-Dioxygenase Inhibitory Compound D-1-Methyl-Tryptophan," Cancer Res, 2007, 67, 15; 7082-7087.
Mezrich, J.D. et al., "An Interaction between Kynurenine and the Aryl Hydrocarbon Receptor Can Generate Regulatory T Cells," J Immunol, 2010, 185, 6, 3190-3198.
Mo, Z. et al., "A Comprehensive Pan-Cancer Analysis of 33 Human Cancers Reveals the Immunotherapeutic Value of Aryl Hydrocarbon Receptor," Frontiers in Immunology, vol. 12; Article 564948; 13 pages (2021).
Muller, A.J. et al., "Inhibiting IDO pathways to treat cancer: lessons from the ECHO-301 trial and beyond," Semin Immunopathol., 2019, 41(1), 9 pages.
Muller, A.J. et al., "Inhibition of indoleamine 2,3-dioxygenase, an immunoregulatory target of the cancer suppression gene Bin 1, potentiates cancer chemotherapy," Nat Med, 11, 3, 312-319.
Nguyen, L.P. and Bradfield, C.A., "The Search for Endogenous Activators of the Hydrocarbon Receptor," Chem Res Toxicol, vol. 21; No. 1; 102-116 (2008).
Nguyen, N.T. et al., "Aryl hydrocarbon receptor and kynurenine: recent advances in autoimmune disease research," Front. Immunol., vol. 5; Article 551; 6 Pages (2014).
Nguyen, N.T. et al., "Aryl hydrocarbon receptor negatively regulates dendritic cell immunogenicity via a kynurenine-dependent mechanism," PNAS, vol. 107; No. 46; 19961-19966 (2010).
Notification Concerning Transmittal of International Preliminary Report on Patentability for International Application No. PCT/US2020/061548, mailed Jun. 2, 2022.
Notification Concerning Transmittal of International Preliminary Report on Patentability for International Application No. PCT/US2021/033078, mailed Dec. 1, 2022.
Notification Concerning Transmittal of the International Preliminary Report on Patentability for International Application No. PCT/US2021/034413, mailed Dec. 8, 2022.
Notification of Transmittal of the International Search Report and Written Opinion for International Application No. PCT/US2021/033078, mailed Sep. 21, 2022.
Notification of Transmittal of the International Search Report and Written Opinion for International Application No. PCT/US2021/034413, mailed Oct. 14, 2021.
Notification of Transmittal of the International Search Report and Written Opinion for International Application No. PCT/US2021/054698, mailed Feb. 4, 2022.
Opitz Christiane A et al: "The therapeutic potential of targeting tryptophan catabolismin cancer." British journal of cancer vol. 122. No. 1 (2020): pp. 30-44.
Opitz, C.A. et al., "An endogenous tumour-promoting ligand of the human aryl hydrocarbon receptor," Nature, vol. 478; 197-203 (2011).
Pandiyan, P. et al., "Microbiome Dependent Regulation of Tregs and Th17 Cells in Mucosa," Front Immunol, vol. 10; Article 426; 17 Pages (2019).
Paris, A. et al., "AhR and Cancer: From Gene Profiling to Targeted Therapy," International Journal of Molecular Sciences, vol. 22; 752; 22 pages (2021).
Platten, M. et al., "Cancer immunotherapy by targeting IDO1/TDO and their downstream effectors," Front Immunol., vol. 5; Article 673; 7 Pages (2015).
Qin, S. et al., "Novel immune checkpoint targets: moving beyond PD-1 and CTLA-4," Molecular Cancer, vol. 18; 155; 14 Pages (2019).
Quintana, F.J. and Weiner, H.L., "Environmental control of Th17 differentiation," Eur J Immunol., vol. 39; No. 3; 655-657 (2009).
Quintana, F.J. et al., "Control of Treg and Th17 cell differentiation by the aryl hydrocarbon receptor," Nature, vol. 453; 65-71 (2008).
Reyes, H. et al., "Identification of the Ah receptor nuclear translocator protein (Arnt) as a component of the DNA binding form of the Ah receptor," Science, 1992, 256, 5060, 1193-1195.
Richards M L et al: "Substituted 2-phenyl-benzimidazole derivatives: novel compounds that suppress key markers of allergy." European journal of medicinal chemistry vol. 41. No. 8 (2006): pp. 950-969.
Rossi, M. and Bot, A., "The Th17 Cell Population and the Immune Homeostasis of the Gastrointestinal Tract," Int Rev Immunol, 2013, 32(5-6), 471-474.

(56) References Cited

OTHER PUBLICATIONS

Rothhammer, V. and Quintana, F.J., "The aryl hydrocarbon receptor: an environmental sensor integrating immune responses in health and disease," Nat Rev Immunol., 2019, 19(3), 184-197.
Routy, B. et al., "Gut microbiome influences efficacy of PD-1-based immunotherapy against epithelial tumors," Science, 2018, 359(6371), 91-97.
Safe, Stephen, et al. "Aryl hydrocarbon receptor (AHR) ligands as selective AHR modulators (SAhRMs)." International journal of molecular sciences vol. 21. No. 6654 (2020).
Sanchez-Martin, M. et al., "Computational Biology and Tissue-based Approaches to Inform Indication Selection for Novel AHR Inhibitor," Presented in Boston, Massachusetts, SITC 36th Annual Meeting, Abstract 15472; Poster# 93, Nov. 12, 2021.
Socinski, M.A. et al., "Atezolizumab for First-Line Treatment of Metastatic Nonsquamous NSCLC," N Engl J Med, vol. 378; No. 24; 2288-2301 (2018).
Suzuki, Y. et al., "Increased serum kynurenine/tryptophan ratio correlates with disease progression in lung cancer," et al., Lung Cancer, 2010, 67(3), 361-365.
Tsai, H. and Hsu, P., "Cancer immunotherapy by targeting immune checkpoints: mechanism of T cell dysfunction in cancer immunity and new therapeutic targets," Journal of Biomedical Science, vol. 24; No. 35; 8 Pages (2017).
Uyttenhove, C. et al., "Evidence for a tumoral immune resistance mechanism based on tryptophan degradation by indoleamine 2,3-dioxygenase," Nat Med, 2003, 9, 10, 1269-1274.
Veldhoen, M. et al., "Natural agonists for aryl hydrocarbon receptor in culture medium are essential for optimal differentiation of Th17 T cells," J. Exp. Med., vol. 206; No. 1; 43-49 (2009).
Veldhoen, M. et al., "Natural agonists for aryl hydrocarbon receptor in culture medium are essential for optimal differentiation of Th17 T cells," J. Exp. Med., vol. 206; No. 1; 43-49; Supplemental Material (2009).
Veldhoen, M. et al., "The aryl hydrocarbon receptor links TH17-cell-mediated autoimmunity to environmental toxins," Nature, vol. 453; 106-109 (2008).
Veldhoen, M. et al., "The aryl hydrocarbon receptor links TH17-cell-mediated autoimmunity to environmental toxins," Nature, vol. 453; 106-110 (2008). (Supplementary Information).
Vlaar, J. et al., "Recurrent activating mutations in AHR act as drivers of urinary tract cancer," BioRxiv 10.1101/2021.11.09. 468005, 25 pages (2021).
Wang, C. et al., "Activation of the aryl hydrocarbon receptor affects activation and function of human monocyte-derived dendritic cells," Clin Exp Immunol., vol. 177; 521-530 (2014).
Wang, L. et al., "Analytical validation of a novel immunohistochemistry assay to determine nuclear AHR expression in human bladder cancer," Ikena Oncology, Inc., SITC 36th Annual Meeting, Poster #58; Nov. 13, 2021.
Wang, Z. et al., "How the AHR Became Important in Cancer: The Role of Chronically Active AHR in Cancer Aggression," International Journal of Molecular Sciences, vol. 22; 387; 22 pages (2021).
Wei, P. et al., "An aryl hydrocarbon receptor ligand acts on dendritic cells and T cells to suppress the Th17 response in allergic rhinitis patients," Lab Invest, vol. 94; No. 5; 528-535 (2014).
Wolchok, J.D. et al., "Overall Survival with Combined Nivolumab and Ipilimumab in Advanced Melanoma," N. Engl. J. Med., vol. 377; No. 14; 1345-1356 (2017).
Xiong, J. et al., "Aryl hydrocarbon receptor mediates Jak2/STAT3 signaling for non-small cell lung cancer stem cell maintenance," Exp Cell Res, 2020, 112288, 13 pages.
Yamada, T. et al., "Constitutive aryl hydrocarbon receptor signaling constrains type I interferon-mediated antiviral innate defense," Nat Immunol., vol. 17; No. 6; 687-694 (2016).
Yeste, A. et al., "IL-21 induces IL-22 production in CD4+ T-cells," Nat Commun, vol. 5; 3753; 29 pages (2014).
Yuan Xu et al: "Design, synthesis and in vitro evaluation of 6-amide-2-aryl benzoxazole/benzimidazole derivatives against tumor cells by inhibiting VEGFR-2 kinase." European journal of medicinal chemistry vol. 179 (2019): pp. 147-165.
Zierer, J. et al., "The fecal metabolome as a functional readout of the gut microbiome," Nat Genet, vol. 50; No. 6; 790-795 (2018).
Bavetsias, V., Lanigan, R. M., Ruda, G. F., Atrash, B., McLaughlin, M. G., Tumber, A., Blagg, J. (2016). 8-Substituted Pyrido[3,4-d]pyrimidin-4(3H)-one Derivatives As Potent, Cell Permeable, KDM4 (JMJD2) and KDM5 (JARID1) Histone Lysine Demethylase Inhibitors. Journal of Medicinal Chemistry, 59(4), 1388-1409.
Le Bihan, Yann-Vaï et al. "C8-substituted pyrido[3,4-d]pyrimidin-4(3H)-ones: Studies towards the identification of potent, cell penetrant Jumonji C domain containing histone lysine demethylase 4 subfamily (KDM4) inhibitors, compound profiling in cell-based target engagement assays." European journal of medicinal chemistry vol. 177 (2019): 316-337.

* cited by examiner

FUSED IMIDAZOLE DERIVATIVES AS AHR ANTAGONISTS

This application is the U.S. National Stage of International Application No. PCT/US2021/033078, filed May 19, 2021, which designates the U.S., published in English, and claims the benefit of U.S. Provisional Application No. 63/027,934, filed May 20, 2020. The above applications are incorporated herein by reference in their entirety.

Disclosed herein are novel compounds of formulae (I)-(VI) and pharmaceutically acceptable salts thereof, methods of preparing said compounds and salts, intermediate compounds useful for preparing said compounds and salts, pharmaceutical compositions comprising said compounds and salts, and methods of using said compounds and salts for the treatment or prophylaxis of diseases, in particular of cancer or conditions with dysregulated immune responses or other disorders associated with aberrant AHR signaling.

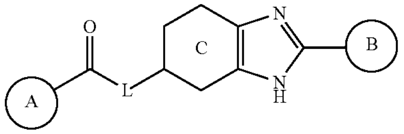

(I)

The Aryl Hydrocarbon Receptor (AHR) is a ligand-activated transcription factor, belonging to the basic helix-loop-helix/Per-Arnt-Sim (bHLH/PAS) family that is located in the cytosol. Upon ligand binding, the AHR translocates to the nucleus where it heterodimerises with ARNT (AHR Nuclear Translocator) upon which it interacts with DREs (Dioxin Response Elements) of AHR-responsive genes to regulate their transcription. The AHR is best known for binding to environmental toxins and inducing the metabolic machinery, such as cytochrome P 450 enzymes (eg. CYP1A1, CYP1A2 and CYP1B1), required for their elimination (Reyes et al., Science, 1992, 256(5060):1 193-5). Activation of AHR by xenobiotics has demonstrated its role in numerous cellular processes such as embryogenesis, tumorigenesis and inflammation.

AHR is expressed in many cells of the immune system, including dendritic cells (DCs), macrophages, T cells and NK cells, and plays an important role in immunoregulation (Nguyen et al., *Front. Immunol.,* 2014, 5:551). The classic exogenous AHR ligands TCDD and 3-methylcholanthrene, for example, are known to induce profound immunosuppression, promote carcinogenesis and induce tumour growth (Gramatzki et al., *Oncogene,* 2009, 28(28):2593-605; Bui et al., *Oncogene,* 2009, 28(41):3642-51; Esser et al., *Trends Immunol.,* 2009, 30:447-454). In the context of immunosuppression, AHR activation promotes regulatory T cell generation, inhibits Th1 and Th17 differentiation, directly and indirectly, and decreases the activation and maturation of DCs (Wang et al., *Clin. Exp. Immunol.,* 2014, 177(2): 521-30; Mezrich et al., *J. Immunol.,* 2010, 185(6):3190-8; Wei et al., *Lab. Invest.,* 2014, 94(5):528-35; Nguyen et al., *PNAS,* 2010, 107(46):19961-6). AHR activation modulates the innate immune response and constitutive AHR expression has been shown to negatively regulate the type-1 interferon response to viral infection (Yamada et al., *Nat. Immunol.,* 2016, 17(6):687-94). Additionally, mice with a constitutively active AHR spontaneously develop tumours (Andersson et al., *PNAS,* 2002, 99(15):9990-5).

In addition to xenobiotics, the AHR can also bind metabolic products of tryptophan degradation. Tryptophan metabolites, such as kynurenine and kynurenic acid, are endogenous AHR ligands that activate the AHR under physiological conditions (DiNatale et al., *Toxicol. Sci.,* 2010, 115(1):89-97; Mezrich et al., *J. Immunol.,* 2010, 185(6): 3190-8; Opitz et al., *Nature,* 2011, 478(7368):197-203). Other endogenous ligands are known to bind the AHR, although their physiological roles are currently unknown (Nguyen & Bradfield, *Chem. Res. Toxicol.,* 2008, 21(1):102-116).

The immunosuppressive properties of kynurenine and tryptophan degradation are well described and are implicated in cancer-associated immunosuppression. The enzymes indoleamine-2,3-dioxygenases 1 and 2 (IDO1/IDO2) as well as tryptophan-2,3-dioxygenase 2 (TDO2) are responsible for catalysing the first and rate-limiting step of tryptophan metabolism. IDO1/2-mediated degradation of tryptophan in tumours and tumour-draining lymph nodes reduces anti-tumour immune responses and inhibition of IDO can suppress tumour formation in animal models (Uyttenhove et al., *Nat. Med.,* 2003, 9(10):1269-74; Liu et al., *Blood,* 2005, 115(17): 3520-30; Muller et al., *Nat. Med.,* 11(3):312-9; Metz, *Cancer Res.,* 2007, 67(15):7082-7).

TDO2 is also strongly expressed in cancer and can lead to the production of Immunosuppressive kynurenine. In glioma, activation of the AHR by kynurenine, downstream of TDO-mediated tryptophan degradation, enhances tumour growth as a consequence of inhibiting anti-tumour immune responses as well as directly promoting tumour cell survival and motility (Opitz et al., Nature, 2011, 478(7368):197-203). AHR ligands generated by tumour cells therefore act in both an autocrine and paracrine fashion on tumour cells and lymphocytes, respectively, to promote tumour growth.

The present disclosure is drawn to novel compounds of formulae (I)-(VI) and/or pharmaceutically acceptable salts thereof. Compounds of the present disclosure have surprisingly been found to effectively inhibit AHR and may therefore be used for treatment or prophylaxis of cancer and/or other conditions where exogenous and endogenous AHR ligands induce dysregulated immune responses, uncontrolled cell growth, proliferation and/or survival of tumor cells, immunosuppression in the context of cancer, inappropriate cellular immune responses, or inappropriate cellular inflammatory responses or diseases that are accompanied by uncontrolled cell growth, proliferation and/or survival of tumor cells, immunosuppression in the context of cancer inappropriate cellular immune responses, or inappropriate cellular inflammatory responses, particularly in which the uncontrolled cell growth, proliferation and/or survival of tumor cells, immunosuppression in the context of cancer, inappropriate cellular immune responses, or inappropriate cellular inflammatory responses is mediated by AHR, such as, for example, liquid and solid tumors, and/or metastases thereof, e.g. head and neck tumors including brain tumors and brain metastases, tumors of the thorax including non-small cell and small cell lung tumors, gastrointestinal tumors including colon, colorectal and pancreatic tumors, liver tumors, endocrine tumors, mammary and other gynecological tumors, urological tumors including renal, bladder and prostate tumors, skin tumors, and sarcomas, and/or metastases thereof.

The present disclosure also relates to pharmaceutical compositions comprising at least one entity chosen from compounds of formulae (I)-(VI) and pharmaceutically acceptable salts thereof. The present disclosure also relates to methods of treatment comprising administering at least one compound, pharmaceutically acceptable salt thereof, and/or pharmaceutical composition of the present disclosure. In some embodiments, the disclosure provides a method of treating a disease or condition mediated by AHR signaling. In some embodiments, the disclosure provides a method of treating a disease or condition associated with aberrant AHR signaling. In some embodiments, the disclosure provides a method of inhibiting cancer cell proliferation mediated by AHR signaling.

As used herein, the term "pharmaceutically acceptable salt" refers to a salt that is pharmaceutically acceptable as defined herein and that has the desired pharmacological activity of the parent compound. Non-limiting examples of pharmaceutically acceptable salts include those derived from inorganic acids, non-limiting examples of which include hydrochloric acid, hydrobromic acid, hydroiodic acid, sulfuric acid, nitric acid, and phosphoric acid, and those derived from organic acids, non-limiting examples of which include acetic acid, trifluoroacetic acid, propionic acid, glycolic acid, pyruvic acid, oxalic acid, stearic acid, malic acid, maleic acid, malonic acid, salicylic acid, succinic acid, fumaric acid, tartaric acid, citric acid, benzoic acid, cinnamic acid, mandelic acid, p-toluenesulfonic acid, methanesulfonic acid, ethanesulfonic acid, and lactic acid.

Additional non-limiting examples of pharmaceutically acceptable salts include those formed when an acidic proton in a parent compound is replaced by a metal ion, non-limiting examples of which include an alkali metal ion and an alkaline earth metal ion, and those formed when an acidic proton present in a parent compound is replaced by a ammonium ion, a primary ammonium ion, a secondary ammonium ion, a tertiary ammonium ion, or a quaternary ammonium ion. Non-limiting examples of alkali metals and alkaline earth metals include sodium, potassium, lithium, calcium, aluminum, magnesium, copper, zinc, iron, and manganese. Additional non-limiting examples of pharmaceutically acceptable salts include those comprising one or more counterions and zwitterions.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. The same rule applies for any other ranges described herein, even if the values within the range are not specifically called out in this disclosure.

The term "compound," as used herein unless otherwise indicated, refers to a collection of molecules having an identical chemical structure as a collection of stereoisomers (for example, a collection of racemates, a collection of cis/trans stereoisomers, or a collection of (E) and (Z) stereoisomers). Therefore, geometric and conformational mixtures of the present compounds and salts are within the scope of the disclosure. Unless otherwise stated, all tautomeric forms of the compounds of the disclosure are within the scope of the disclosure.

"Stereoisomer" as used herein refers to enantiomers and diastereomers.

The term "tautomer," as used herein, refers to one of two or more isomers of a compound that exist together in equilibrium, and are readily interchanged by migration of an atom or group within the molecule.

Unless indicated otherwise, nomenclature used to describe chemical groups or moieties as used herein follow the convention where, reading the name from left to right, the point of attachment to the rest of the molecule is at the right-hand side of the name. For example, the group "($C_{1-3}$ alkoxy)$C_{1-3}$ alkyl," is attached to the rest of the molecule at the alkyl end. Further examples include methoxyethyl, where the point of attachment is at the ethyl end, and methylamino, where the point of attachment is at the amine end.

Unless indicated otherwise, where a chemical group is described by its chemical formula or structure having a terminal bond moiety indicated by "—", it will be understood that the "—" represents the point of attachment. In some embodiments, a wavy line (i.e.,  ) depicts the point of attachment.

As used herein, an "acyl" or "alkanoyl" is a functional group with formula RCO— (i.e., RC(O)—) where R is bound to the carbon atom of the carbonyl functional group by a single bond and the "—" denotes the point of attachment to the rest of the molecule. Non-limiting examples of acyls include formyl (HC(O)— (i.e., —C(O)H) also called methanoyl), acetyl ($CH_3C(O)$—, also called ethanoyl), and benzoyl (PhC(O)—).

The term "alkyl" or "aliphatic" as used herein, means a straight-chain (i.e., unbranched) or branched, substituted or unsubstituted hydrocarbon chain that is completely saturated and that has a single point of attachment to the rest of the molecule. Unless otherwise specified, an alkyl group is a hydrocarbon chain of 1 to 20 alkyl carbon atoms. In some embodiments, an alkyl group contains one to twelve carbon atoms ($C_1$-$C_{12}$). In some embodiments, an alkyl group contains one to eight carbon atoms ($C_1$-$C_8$). In some embodiments, an alkyl group contains one to six carbon atoms ($C_1$-$C_6$). In some embodiments, an alkyl group contains one to four carbon atoms ($C_1$-$C_4$). In some embodiments, a cyclic alkyl group contains three to six carbon atoms ($C_3$-$C_6$). Non-limiting examples of substituted and unsubstituted linear, branched, and cyclic alkyl groups include methyl, ethyl, n-propyl, iso-propyl, cyclopropyl, n-butyl, sec-butyl, iso-butyl, tert-butyl, cyclobutyl, cyclopentyl, cyclohexyl, hydroxymethyl, chloromethyl, fluoromethyl, trifluoromethyl, aminomethyl, 2-aminoethyl, 3-aminopropyl, 4-aminobutyl, dimethylaminomethyl, 2-dimethylaminoethyl, 3-dimethylaminopropyl, 4-dimethylaminobutyl, cyclopropylmethyl, cyclobutylmethyl, cyclopentylmethyl, trifluoroethyl, and trifluoropropyl.

"Alkoxy," as used herein, refers to an alkyl group, as previously defined, attached to the principal carbon chain through an oxygen ("alkoxy") atom.

"Halo" and "halogen," as used herein, are interchangeable and refer to halogen atoms such as fluoro (F), chloro (Cl), bromo (Br), and iodo (I).

"Haloalkyl" refers to an alkyl group substituted with one or more halo atoms (F, Cl, Br, I). For example, "fluoromethyl" refers to a methyl group substituted with one or more fluoro atoms (e.g., monofluoromethyl, difluoromethyl, or trifluoromethyl).

"Haloalkoxy" refers to an alkoxy group substituted with one or more halo atoms (F, Cl, Br, I). For example, "fluoromethoxy" refers to a methoxy group substituted with one or more fluoro atoms (e.g., monofluoromethoxy, difluoromethoxy, or trifluoromethoxy).

"Hydroxyalkyl" refers to an alkyl group substituted with one or more hydroxy groups (—OH).

The terms "cycloalkyl" and "cycloalkyl group" as used interchangeably herein refer to a cyclic saturated monovalent hydrocarbon ring of three to twelve carbon atoms that has a single point of attachment to the rest of the molecule.

Cycloalkyl groups may be unsubstituted or substituted. In some embodiments, a cycloalkyl group comprises three to eight carbon atoms ($C_3$-$C_8$). In some embodiments, a cycloalkyl group comprises three to six carbon atoms ($C_3$-$C_6$). Non-limiting examples of substituted and unsubstituted cycloalkyls include cyclopropyl, cyclopropylmethyl, cyclobutyl, cyclobutylmethyl, cyclopentyl, cyclopentylmethyl, cyclohexyl, cycloheptyl, and cyclooctyl.

The terms "cyclohexenyl" and "cyclohexenyl group" as used interchangeably herein refer to a cyclic six carbon ring comprising at least one unsaturated bond. Cyclohexenyl groups may be unsubstituted or substituted. In some embodiments, a cyclohexenyl group comprises one or two double bonds.

The terms "alkylene" and "alkylene group" as used interchangeably herein refer to a saturated divalent (i.e., having two points of attachment to the rest of the molecule) hydrocarbon radical comprising one to twelve carbon atoms ($C_1$-$C_{12}$). Alkylene groups may be linear, branched, or cyclic. Alkylene groups may be unsubstituted or substituted. In some embodiments, an alkylene group comprises one to eight carbon atoms ($C_1$-$C_8$). In some embodiments, an alkylene group comprises one to six carbon atoms ($C_1$-$C_6$). In some embodiments, an alkylene group comprises one to four carbon atoms ($C_1$-$C_4$). Non-limiting examples of alkylene groups include methylene and ethylene.

The terms "alkenyl" and "alkenyl group" as used interchangeably herein refer to a monovalent (i.e., having a single point of attachment to the rest of the molecule) hydrocarbon radical comprising two to eight carbon atoms ($C_2$-$C_8$) with at least one site of unsaturation (i.e., an sp2 carbon-carbon double bond). Alkenyl groups may be linear, branched, or cyclic. Alkenyl groups may be unsubstituted or substituted. In some embodiments, an alkenyl group contains two to six carbon atoms ($C_2$-$C_6$). In some embodiments, an alkenyl group contains two to four carbon atoms ($C_2$-$C_4$). Alkenyl groups may have E or Z orientations. Non-limiting examples of alkenyl groups include ethenyl (also called vinyl), 1-propenyl, iso-propenyl, and 2-chloroethenyl.

The terms "alkenylene" and "alkenylene group" as used interchangeably herein refer to a divalent (i.e., having two points of attachment to the rest of the molecule) hydrocarbon radical of two to eight carbon atoms ($C_2$-$C_8$) with at least one site of unsaturation (e.g., an sp2 carbon-carbon double bond). Alkenylene groups may be linear, branched, or cyclic. Alkenylene groups may be unsubstituted or substituted. In some embodiments, an alkylene group contains two to six carbon atoms ($C_2$-$C_6$). In some embodiments, an alkylene group contains two to four carbon atoms ($C_2$-$C_4$). Alkylene groups may have E or Z orientations. A non-limiting example of an alkenyl group is ethenylene (also called vinylene).

The terms "alkynyl" and "alkynyl group" as used interchangeably herein refer to a monovalent (i.e., having a single point of attachment to the rest of the molecule) hydrocarbon radical of two to eight carbon atoms ($C_2$-$C_8$) with at least one site of unsaturation (i.e., an sp carbon-carbon triple bond). Alkynyl groups may be linear or branched. Alkynyl groups may be unsubstituted or substituted. In some embodiments, an alkynyl group contains two to six carbon atoms ($C_2$-$C_6$). In some embodiments, an alkynyl group contains two to four carbon atoms ($C_2$-$C_4$). A non-limiting example of an alkynyl group is ethynyl.

The terms "alkynylene" and "alkynylene group" as used interchangeably herein refer to a divalent (i.e., having two points of attachment to the rest of the molecule) hydrocarbon radical of two to eight carbon atoms ($C_2$-$C_8$) with at least one site of unsaturation (i.e., an sp carbon-carbon triple bond). Alkynylene groups may be linear or branched. Alkynylene groups may be unsubstituted or substituted. In some embodiments, an alkynylene group contains two to six carbon atoms ($C_2$-$C_6$). In some embodiments, an alkynylene group contains two to four carbon atoms ($C_2$-$C_4$). A non-limiting example of an alkynylene group is ethynylene.

As used herein, "aromatic groups" or "aromatic rings" refer to chemical groups that contain conjugated, planar ring systems with delocalized pi electron orbitals comprised of [4n+2] p orbital electrons, wherein n is an integer ranging from 0 to 6. Nonlimiting examples of aromatic groups include aryl and heteroaryl groups.

The terms "aryl" and "aryl group" as used interchangeably herein refer to a monovalent (i.e., having a single point of attachment to the rest of the molecule) aromatic hydrocarbon radical of 6-20 carbon atoms ($C_6$-$C_{20}$). Aryl groups can be unsubstituted or substituted. Non-limiting examples of unsubstituted and substituted aryl groups include phenyl, 2-fluorophenyl, 3-fluorophenyl, 4-fluorophenyl, 2-methylphenyl, 3-methylphenyl, 4-methylphenyl, 2-chlorophenyl, 3-chlorophenyl, 4-chlorophenyl, 2,6-dichlorophenyl, 3,4-difluorophenyl, 2-hydroxyphenyl, 3-hydroxyphenyl, 4-hydroxyphenyl, 2-methoxyphenyl, 3-methoxyphenyl, 4-methoxyphenyl, 2-phenoxyphenyl, 3-phenoxyphenyl, 4-phenoxyphenyl, 2-cyanophenyl, 3-cyanophenyl, 4-cyanophenyl, 2-dimethylaminophenyl, 3-dimethylaminophenyl, 4-dimethylaminophenyl, 3-methylsulfonylphenyl, 4-methylsulfonylphenyl, 3-aminophenyl, 3-methylaminophenyl, 3-(2-hydroxyethoxy)phenyl, 2-trifluoromethylphenyl, 3-trifluoromethylphenyl, 4-trifluoromethylphenyl, 2-isopropylphenyl, 3-isopropylphenyl, 4-isopropylphenyl, 1-naphthyl and 2-naphthyl.

The term "heteroalkyl" as used herein refers to an alkyl group wherein at least one of the carbon atoms in the chain is replaced by a heteroatom, such as nitrogen, oxygen, phosphorous, and sulfur. A heteroalkyl group may be unsubstituted or substituted.

The terms "heterocycloalkyl," "heterocycle," "heterocyclyl," and "heterocyclic group" as used interchangeably herein refer to a saturated or partially unsaturated ring system of 3 to 20 atoms, wherein at least one of the ring atoms is a heteroatom, such as nitrogen, oxygen, phosphorous, and sulfur. A heterocycloalkyl group may be unsubstituted or substituted. In some embodiments, a heterocycloalkyl group comprises 3 to 10 atoms. In some embodiments, a heterocycloalkyl group contains 3 to 7 atoms. In some embodiments, a heterocycloalkyl group is monocyclic. In some embodiments, a heterocycloalkyl group is bicyclic. In some embodiments, a heterocycloalkyl group comprises fused rings. Non-limiting examples of unsubstituted and substituted heterocycloalkyl groups include pyrrolidinyl, N-methylpyrrolidinyl, azetidinyl, dihydrofuranyl, tetrahydrofuranyl, tetrahydropyranyl, 3-hydroxypyrrolidinyl, 3-methoxypyrrolidinyl, and benzodioxolyl.

The terms "heteroaryl" and "heteroaryl group" as used interchangeably herein refer to an aromatic ring system of 3 to 20 atoms, wherein at least one of the ring atoms is a heteroatom, such as nitrogen, oxygen, phosphorous, and sulfur. A heteroaryl group may be unsubstituted or substituted. In some embodiments, a heteroaryl group contains 5 to 20 atoms. In some embodiments, a heteroaryl group contains 5 to 9 atoms. In some embodiments, a heteroaryl group contains 5 atoms. In some embodiments, a heteroaryl group contains 6 atoms. In some embodiments, a heteroaryl group contains 7 atoms. In some embodiments, a heteroaryl group is monocyclic. In some embodiments, a heteroaryl group is bicyclic. In some embodiments, a heteroaryl group contains fused rings. Non-limiting examples of heteroaryl groups include pyridinyl, imidazolyl, imidazopyridinyl, pyrimidinyl, pyrazolyl, triazolyl, pyrazinyl, tetrazolyl, furyl, 2-thienyl, 3-thienyl, isoxazolyl, thiazolyl, oxadiazolyl, 3-methyl-1,2,4-oxadiazolyl, 3-phenyl-1,2,4-oxadiazolyl, oxazolyl, isothiazolyl, pyrrolyl, quinolinyl, isoquinolinyl, tetrahydroisoquinolinyl, indolyl, benzimidazolyl, benzofuranyl, indazolyl, indolizinyl, phthalazinyl, pyridazinyl, triazinyl, thiadiazolyl, furazanyl, benzofurazanyl, benzothiophenyl, benzothiazolyl, benzoxazolyl, quinazolinyl, quinoxalinyl, naphthyridinyl, furopyridinyl, and 1H-pyrrolo[2,3-b]pyridinyl. Non-limiting examples of heteroaryl groups include:

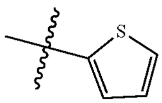 ; 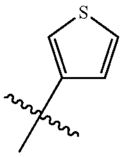 ; 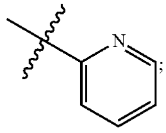 ;

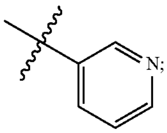 ; 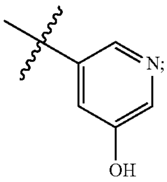 ; 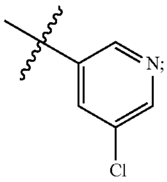 ;

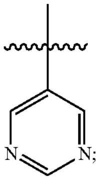 ; 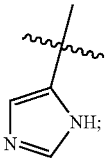 ; 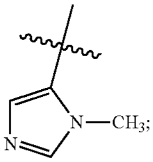 ; 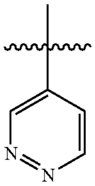 ;

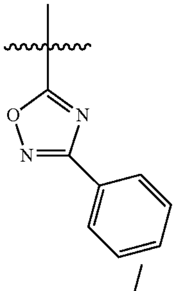 ; 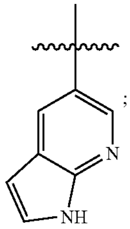 ; and

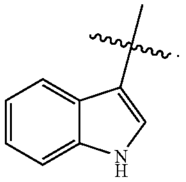 .

The phrase "optionally substituted" as used herein means may or may not be "substituted." The term "substituted" as used herein refers to the replacement of one or more hydrogen atoms on a group (such as on an alkyl group, alkylene group, alkenyl group, alkenylene group, alkynyl group, alkynylene group, aryl group, heterocycloalkyl group, or heteroaryl group) by one or more substituents. Non-limiting examples of substituents that replace a single hydrogen atom include halogen, hydroxyl, and amino. Non-limiting examples of substituents that replace two hydrogen atoms include oxo and methene. Non-limiting examples of substituents that replace three hydrogen atoms include nitrile.

Additional non-limiting examples of substituents include:

$C_1$-$C_6$ linear, branched, and cyclic alkyl groups, non-limiting examples of which include methyl, ethyl, n-propyl, iso-propyl, cyclopropyl, n-butyl sec-butyl, iso-butyl, tert-butyl, cyclobutyl, cyclopentyl, and cyclohexyl;

$C_2$-$C_8$ linear, branched, and cyclic alkenyl groups, non-limiting examples of which include ethenyl (also called vinyl), 1-propenyl, and iso-propenyl;

$C_2$-$C_8$ linear and branched alkynyl groups, non-limiting examples of which include ethynyl;

substituted and unsubstituted aryl groups, non-limiting examples of which include phenyl, 2-fluorophenyl, 3-methylphenyl, 4-chlorophenyl, 2,6-dichlorophenyl, 3,4-difluorophenyl, 3-hydroxyphenyl, 4-cyanophenyl, 2-dimethylaminophenyl, 3-methylsulfonylphenyl, 4-trifluoromethylphenyl, 3-isopropylphenyl, 1-naphthyl, and 2-naphthyl;

substituted and unsubstituted heterocyclic groups, non-limiting examples of which include pyrrolidinyl, N-methylpyrrolidinyl, azetidinyl, dihydrofuranyl, tetrahydrofuranyl, tetrahydropyranyl, 3-hydroxypyrrolidinyl, and 3-methoxypyrrolidinyl;

substituted and unsubstituted heteroaryl groups, non-limiting examples of which include pyridinyl, imidazolyl, pyrimidinyl, pyrazolyl, furyl, 2-thienyl, 3-thienyl, isoxazolyl, thiazolyl, oxadiazolyl, 3-methyl-1,2,4-oxadiazolyl, 3-phenyl-1,2,4-oxadiazolyl, indolyl, benzothiazolyl, and 1H-pyrrolo[2,3-b]pyridinyl;

$-(CR_aR_b)_zOR_c$, non-limiting examples of which include $-OH$, $-OCH_3$, $-OCH_2OH$, and $-OCH_2CH_3$;

$-(CR_aR_b)_zN(R_c)(R_d)$, non-limiting examples of which include $-NH_2$, $-NHCH_3$, $-N(CH_3)_2$, $-CH_2NH_2$, $-CH_2NHCH_3$, a halogen atom, non-limiting examples of which include a fluorine atom ($-F$) and a chlorine atom ($-Cl$);

$-(CR^aR^b)_zCN$;

$-(CR^aR^b)_zNO_2$;

$-CH_xX_y$, wherein X is a halogen atom and x+y sum to 3, non-limiting examples of which include $-CH_2F$, $-CHF_2$, and $-CF_3$;

$-(CR^aR^b)_zC(O)R^c$, non-limiting examples of which include $-COCH_3$, $-COCH_2CH_3$, and $-CH_2COCH_3$;

$-(CR^aR^b)_zC(O)OR^c$, non-limiting examples include $CO_2H$, $-CO_2CH_3$, $-CO_2CH_2CH_3$, and $-CH_2CO_2CH_3$;

$-(CR^aR^b)_zC(O)N(R^c)(R^d)$, non-limiting examples of which include $-CONH_2$, $-CONHCH_3$, $-CON(CH_3)_2$, $-CH_2CONH_2$, $-CH_2CONHCH_3$, $-CH_2CON(CH_3)_2$;

$-(CR^aR^b)_zSO_2R^c$; non-limiting examples of which include $-SO_2H$, $-SO_2CH_3$, $-CH_2SO_2H$, $-CH_2SO_2CH_3$, $-SO_2C_6H_5$, and $-CH_2SO_2C_6H_5$; and $-(CR^aR^b)_zSO_3R^c$; non-limiting examples of which include $-SO_3H$, $-SO_3CH_3$, $-CH_2SO_3H$, $-CH_2SO_3CH_3$, $-SO_3C_6H_5$, and $-CH_2SO_3C_6H_5$;

wherein each of $R^a$ and $R^b$ is independently chosen from hydrogen and substituted or unsubstituted $C_1$-$C_6$ linear, branched, or cyclic alkyl, each of $R^c$ and $R^d$ is independently chosen from hydrogen, substituted or unsubstituted $C_1$-$C_6$ linear, branched, or cyclic alkyl, and aryl, or wherein $R^c$ and $R^d$ together form a ring system comprising 3 to 7 atoms, and z is chosen from 0, 1, 2, 3, and 4.

As used herein, the term "pharmaceutical composition" refers to a preparation that is in such form as to permit the biological activity of the active ingredient to be effective, and that contains no additional components that are unacceptably toxic to a subject to which the composition would be administered. In some embodiments, such compositions may be sterile.

The term "pharmaceutically acceptable," as used herein in "pharmaceutically acceptable salt" and "pharmaceutically acceptable excipient," refers to a component that is, within the scope of sound medical judgment, suitable for use in contact with the tissues of humans and other mammals without undue toxicity, irritation, allergic response and the like, and are commensurate with a reasonable benefit/risk ratio.

The phrase "pharmaceutically acceptable excipient" is employed herein to refer to a pharmaceutically acceptable material chosen from a solvent, dispersion media, diluent, dispersion, suspension aid, surface active agent, isotonic agent, thickening or emulsifying agent, preservative, polymer, peptide, protein, cell, hyaluronidase, and mixtures thereof. In some embodiments, the solvent is an aqueous solvent.

"Treatment," "treat," and "treating" refer to reversing, alleviating (e.g., alleviating one or more symptoms), and/or delaying the progression of a medical condition or disorder described herein.

The terms "disease" and "disorder" are used interchangeably herein and refer to any alteration in state of the body or of some of the organs, interrupting or disturbing the performance of the functions and/or causing symptoms such as discomfort, dysfunction, distress, or even death to the person afflicted or those in contact with a person. A disease or disorder can also relate to a distemper, ailing, ailment, malady, sickness, illness, complaint, indisposition, or affection.

"Subject," as used herein, means an animal subject, such as a mammalian subject, and particularly human beings.

As used herein, the term "administering" refers to the placement of a compound, pharmaceutically acceptable salt thereof, and/or a pharmaceutical composition comprising into a mammalian tissue or a subject by a method or route that results in at least partial localization of the compound, salt, and/or composition at a desired site or tissue location.

The term "therapeutically effective amount" as used herein refers to an amount of a compound or salt that produces a desired effect for which it is administered (e.g., improvement in symptoms of a disease or condition mediated by AhR signaling, lessening the severity of such a disease or condition or a symptom thereof, and/or reducing progression any one of the foregoing). The exact amount of an effective dose will depend on the purpose of the treatment and will be ascertainable by one skilled in the art using known techniques (see, e.g., Lloyd (1999) The Art, Science and Technology of Pharmaceutical Compounding).

One of ordinary skill in the art would recognize that, when an amount of a compound is disclosed, the relevant amount of a pharmaceutically acceptable salt form of the compound is an amount equivalent to the amount of the free base of the compound. The amounts of the compounds and pharmaceutically acceptable salts disclosed herein are based upon the free base form of the relevant compound. For example, "10 mg of at least one entity chosen from compounds of Formulas I or Ia and pharmaceutically acceptable salts thereof" refers to 10 mg of a compound of Formulas I or Ia or an amount of a pharmaceutically acceptable salt of the compound of Formulas I or Ia equivalent to 10 mg of the relevant compound of Formulas I or Ia.

The "effectiveness" of a compound or composition of the disclosure can be assessed by any method known to one of ordinary skill in the art, including those described in the examples of this disclosure. Effectiveness can be established in vitro (biochemical and/or biological in cultured cells) and/or in vivo. Effectiveness in vitro may be used to extrapolate or predict some degree of effectiveness in vivo, in an animal or in a human subject. A reference or standard or comparison may be used. The term "effective" at inhibiting a receptor (such as AhR), and/or signaling mediated by the enzyme in the context of this disclosure and claims means reducing/activating the activity of the receptor and/or the activation and propagation of the signaling pathway in terms of activation of a downstream molecule or known biological effect by a detectable or measurable amount relative to the baseline activity. This can be assessed in vitro or in vivo and, in some cases, extrapolated to what an activity or benefit in vivo might be by one of ordinary skill in the art. In some embodiments, the reduction or activation is measured in terms of percentage reduction or activation, relative to the activity in the absence of exposure to the compound of the disclosure, including, for example, at least 5%, at least 10%, 20%, at least 30%, at least 40%, at least 50%, at least 60%, at least 70%, at least 80%, at least 90%, or about 100%. The activity might also fall within a range, e.g., 5-10%, 10-20%, and any other range interval between 1% and 100%. An amount is "effective" in vivo if it produces any benefit to the subject to whom the compound or salt is administered.

Disclosed herein are compounds of Formula I:

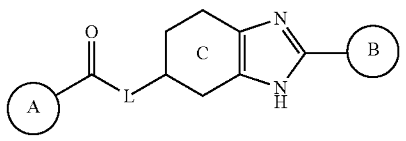

(I)

and pharmaceutically acceptable salts thereof,
wherein:

ring A is chosen from optionally substituted 5-10 membered aryls, optionally substituted 4-10 membered heteroaryls, optionally substituted 3-10 membered cycloalkyls, and optionally substituted 3-10 membered heterocycloalkyls;

ring B is chosen from optionally substituted 5-10 membered aryls, optionally substituted 4-10 membered heteroaryls, optionally substituted 3-10 membered cycloalkyls, and optionally substituted 3-10 membered heterocycloalkyls;

ring C is chosen from optionally substituted cyclohexenyls and optionally substituted phenyls; and L is chosen from divalent linking groups, provided that ring B is not

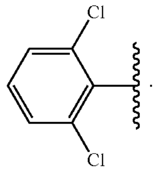 [SMILES: *c1c(Cl)cccc1Cl ; "."]

In some embodiments, ring C is chosen from optionally substituted cyclohexenyls, i.e., cyclohexenyl rings having at least one substituent in addition to the L group. In some embodiments, ring C is chosen from optionally substituted cyclohexenyls comprising one double bond. In some embodiments, ring C is chosen from optionally substituted cyclohexenyls comprising two double bonds. In some embodiments, ring C is chosen from optionally substituted phenyl groups.

In some embodiments, at least one substituent on ring C is chosen from halos, hydroxy, cyano, $C_1$-$C_{10}$ alkyls, $C_1$-$C_{10}$ alkoxys, $C_1$-$C_{10}$ haloalkyls, 3-10 membered cycloalkyls, 3-10 membered heterocycloalkyls, 6-10 membered aryls, and 5-10 membered heteroaryls.

In some embodiments, ring C is chosen from optionally substituted phenyl groups. Accordingly, also disclosed herein are compounds of formula (II):

(II)

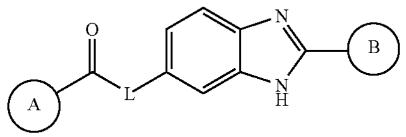

and pharmaceutically acceptable salts thereof, wherein:

ring A is chosen from optionally substituted 5-10 membered aryls, optionally substituted 4-10 membered heteroaryls, optionally substituted 3-10 membered cycloalkyls, and optionally substituted 3-10 membered heterocycloalkyls;

ring B is chosen from optionally substituted aryls, optionally substituted heteroaryls, optionally substituted cycloalkyls, and optionally substituted heterocycloalkyls; and L is chosen from divalent linking groups, provided that ring B is not

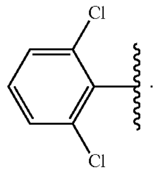 [SMILES: *c1c(Cl)cccc1Cl ; "."]

In some embodiments, in compounds of formula (I) and (II), ring B is chosen from 6-10 membered aryls, 5-10 membered heteroaryls, 3-10 membered cycloalkyls, and 3-10 membered heterocycloalkyls, wherein each 6-10 membered aryl, 5-10 membered heteroaryl, 3-10 membered cycloalkyl, and 3-10 membered heterocycloalkyl is independently optionally substituted with 1 to 5 instances of $R^B$.

In some embodiments, ring B is chosen from 6-8 membered aryls optionally substituted with 1 to 5 instances of $R^B$. In some embodiments, ring B is phenyl optionally substituted with 1 to 3 instances of $R^B$. In some embodiments, ring B is chosen from 6-8 membered heteroaryls optionally substituted with 1 to 5 instances of $R^B$. In some embodiments, ring B is chosen from benzodioxolyl, pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, pyridinonyl, and pyrimidinyl, wherein each of benzodioxolyl, pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl is independently optionally substituted with 1 to 3 instances of $R^B$. In some embodiments, ring B is chosen from pyrazolyl, isothiazoyl, isoxazolyl, pyridinyl, pyrimidinyl, and thiophenyl, wherein each of pyrazolyl, isothiazoyl, isoxazolyl, pyridinyl, pyrimidinyl, and thiophenyl is independently optionally substituted with 1 to 3 instances of $R^B$.

In some embodiments, each $R^B$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and —NR"R".

In some embodiments, each R" is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls.

In some embodiments, in compounds of formula (I) and (II), ring B is chosen from optionally substituted 6-10 membered aryls, optionally substituted 5-10 membered heteroaryls, optionally substituted 3-10 membered cycloalkyls, and optionally substituted 3-10 membered heterocycloalkyls.

In some embodiments, in compounds of formula (I) and (II), ring A is chosen from 5-10 membered aryls, 5-8 membered heteroaryls, 3-10 membered cycloalkyls, and 3-10 membered heterocycloalkyls, wherein each 6-10 membered aryl, 5-10 membered heteroaryl, 3-10 membered cycloalkyl, and 3-10 membered heterocycloalkyl is independently optionally substituted with 1 to 5 instances of $R^A$;

ring B is chosen from 6-10 membered aryls, 5-10 membered heteroaryls, 3-10 membered cycloalkyls, and 3-10 membered heterocycloalkyls, wherein each 6-10 membered aryl, 5-10 membered heteroaryl, 3-10 membered cycloalkyl, and 3-10 membered heterocycloalkyl is independently optionally substituted with 1 to 5 instances of $R^B$;

each $R^A$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and NR"R";

each $R^B$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and NR"R"; and each R" is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls.

In some embodiments, in compounds of formula (I) and (II), ring A is chosen from 3-10 membered cycloalkyl optionally substituted with 1 to 5 instances of $R^A$. In some embodiments, ring A is chosen from cyclopropyl, cyclobutyl, cyclopentyl, cyclohexyl, cycloheptyl, and cyclooctyl optionally substituted with 1 to 5 instances of $R^A$. In some embodiments, ring A is chosen from 6-8 membered aryls optionally substituted with 1 to 5 instances of $R^A$. In some embodiments, ring A is phenyl optionally substituted with 1 to 3 instances of $R^A$. In some embodiments, ring A is chosen from 5-8 membered heteroaryls optionally substituted with 1 to 5 instances of $R^A$.

In some embodiments, ring B is phenyl optionally substituted with 1 to 5 instances of $^{RB}$. Accordingly, also disclosed herein are compounds of formula (III):

(III)

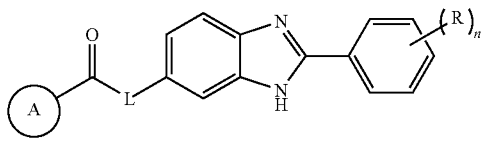

and pharmaceutically acceptable salts thereof,
wherein:

ring A is chosen from optionally substituted 5-10 membered aryls, optionally substituted 4-10 membered heteroaryls, optionally substituted 3-10 membered cycloalkyls, and optionally substituted 3-10 membered heterocycloalkyls;

L is chosen from divalent linking groups;

n is 0, 1, 2, 3, 4, or 5; and each R is independently chosen from optionally substituted $C_1$-$C_{10}$ alkyls, optionally substituted $C_1$-$C_{10}$ alkoxys, optionally substituted aminos, cyano, halos, hydroxy, and —C(O)H.

In some embodiments, in compounds of formulae (I)-(III), L is chosen from $C_1$-$C_5$ alkyl divalent linking groups, $C_1$-$C_5$ heteroalkyl divalent linking groups, —O—, $C_1$-$C_5$ alkoxy divalent linking groups, —NH—, substituted divalent amines, $C_1$-$C_5$ amino divalent linking groups, —S—, and $C_1$-$C_5$ thio divalent linking groups. In some embodiments, L is chosen from —NH— and substituted divalent amines of formula —NR'—, wherein R' is chosen from halos, $C_1$-$C_{10}$ alkyls, $C_1$-$C_{10}$ haloalkyls, $C_1$-$C_{10}$ alkoxys, and $C_1$-$C_{10}$ haloalkoxys.

In some embodiments, in compounds of formulae (I)-(VI), n is 0, 1, 2, 3, 4, or 5. In some embodiments, n is 0, 1, or 2. In some embodiments, n is 1 or 2. In some embodiments, n is 1.

In some embodiments, in compounds of formulae (I)-(VI), each R is independently chosen from halos, optionally substituted $C_1$-$C_{10}$ alkyls, and optionally substituted $C_1$-$C_{10}$ alkoxys. In some embodiments, each R is independently chosen from halos and optionally substituted $C_1$-$C_5$ alkyls. In some embodiments, each R is independently chosen from optionally substituted $C_1$ alkyls. In some embodiments, each R is independently chosen from methyl and halogenated methyls. In some embodiments, each R is independently chosen from fluoro, methyl, monofluoromethyl, difluoromethyl, and trifluoromethyl.

In some embodiments, disclosed herein are compounds of formula (IV):

(IV)

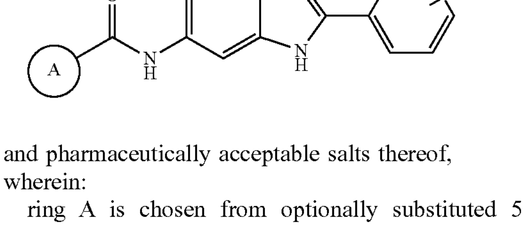

and pharmaceutically acceptable salts thereof,
wherein:

ring A is chosen from optionally substituted 5-10 membered aryls, optionally substituted 4-10 membered heteroaryls, optionally substituted 3-10 membered cycloalkyls, and optionally substituted 3-10 membered heterocycloalkyls;

n is 0, 1, 2, 3, 4, or 5; and each R is independently chosen from optionally substituted $C_1$-$C_{10}$ alkyls, optionally substituted $C_1$-$C_{10}$ alkoxys, optionally substituted aminos, cyano, halos, hydroxy, and —C(O)H.

In some embodiments, in compounds of formulae (I)-(IV), ring A is chosen from 5-10 membered aryls, 5-10 membered heteroaryls, 3-10 membered cycloalkyls, and 3-10 membered heterocycloalkyls, wherein each 6-10 membered aryl, 5-10 membered heteroaryl, 3-10 membered cycloalkyl, and 3-10 membered heterocycloalkyl is independently optionally substituted with 1 to 5 instances of $R^A$.

In some embodiments, each $R^A$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and —NR"R".

In some embodiments, in compounds of formulae (I)-(IV), ring A is chosen from 3-10 membered cycloalkyl optionally substituted with 1 to 5 instances of $R^A$. In some embodiments, ring A is chosen from cyclopropyl, cyclobutyl, cyclopentyl, cyclohexyl, cycloheptyl, and cyclooctyl optionally substituted with 1 to 5 instances of $R^A$. In some embodiments, ring A is chosen from 6-8 membered aryls optionally substituted with 1 to 5 instances of $R^A$. In some embodiments, ring A is phenyl optionally substituted with 1 to 3 instances of $R^A$. In some embodiments, ring A is chosen from 5-8 membered heteroaryls optionally substituted with 1 to 5 instances of $R^A$.

In some embodiments, ring A is chosen from pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl, wherein each of pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl is independently optionally substituted with 1 to 3 instances of $R^A$. In some embodiments, ring A is triazolyl optionally substituted with 1 to 3 instances of $R^A$. In some embodiments, ring A is pyrazolyl optionally substituted with 1 to 3 instances of $R^A$.

In some embodiments, ring A is chosen from 5-8 membered heterocycloalkyls optionally substituted with 1 to 5 instances of $R^A$. In some embodiments, ring A is chosen from pyrrolidinyl, pyrazolidinyl, piperidinyl, piperazinyl, morpholino, azepinyl, tetrahydropyranyl, and tetrahydrofuranyl, wherein each of pyrrolidinyl, pyrazolidinyl, piperidinyl, piperazinyl, morpholino, azepinyl, tetrahydropyranyl, and tetrahydrofuranyl is independently optionally substituted with 1 to 3 instances of $R^A$.

In some embodiments, each $R^A$ is independently chosen from halos, $C_1$-$C_{10}$ alkyls, $C_1$-$C_{10}$ haloalkyls, $C_1$-$C_{10}$ alkoxys, $C_1$-$C_{10}$ haloalkoxys, and —NR"R". In some embodiments, each $R^B$ is independently chosen from halos, $C_1$-$C_{10}$ alkyls, and $C_1$-$C_{10}$ haloalkyls. In some embodiments, each R" is independently chosen from hydrogen and $C_1$-$C_{10}$ alkyls.

In some embodiments, each $R^A$ is independently chosen from halos, $C_1$-$C_{10}$ alkyls, $C_1$-$C_{10}$ haloalkyls, $C_1$-$C_{10}$ alkoxys, $C_1$-$C_{10}$ haloalkoxys, and —NR"R"; each $R^B$ is independently chosen from halos, $C_1$-$C_{10}$ alkyls, and $C_1$-$C_{10}$ haloalkyls; and each R" is independently chosen from hydrogen and $C_1$-$C_{10}$ alkyls. In some embodiments, ring A is triazolyl or pyrazolyl, and ring A is optionally substituted with 1 to 3 methyl groups.

In some embodiments, ring A is chosen from 5-10 membered aryls, 4-10 membered heteroaryls, 3-10 membered cycloalkyls, and 3-10 membered heterocycloalkyls, wherein each 5-10 membered aryl, 4-10 membered heteroaryl, 3-10 membered cycloalkyl, and 3-10 membered heterocycloalkyl is independently optionally substituted with 1 to 5 instances of $R^A$; and each $R^A$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and —NR"R", wherein each R" is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls.

In some embodiments, ring A is chosen from 5-8 membered heteroaryls optionally substituted with 1 to 4 instances of $R^A$. In some embodiments, ring A is chosen from 5-8 membered aryls optionally substituted with 1 to 4 instances of $R^A$. In some embodiments, ring A is chosen from 4-8 membered cycloalkyls optionally substituted with 1 to 4 instances of $R^A$.

In some embodiments, ring A is chosen from pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl, wherein each of pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl is independently optionally substituted with 1 to 3 instances of $R^A$. In some embodiments, ring A is chosen from pyrazolyl optionally substituted with 1 to 3 instances of $R^A$ and triazolyl rings optionally substituted with 1 to 2 instances of $R^A$.

In some embodiments, ring A and ring B, when present, are independently chosen from

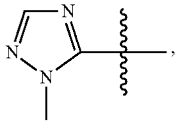, 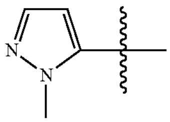,

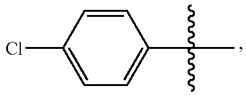, 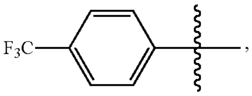,

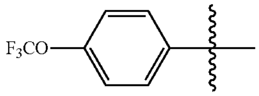, 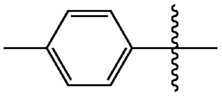,

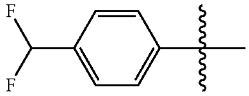, 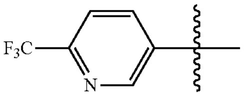,

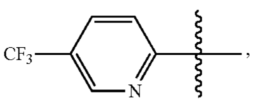, 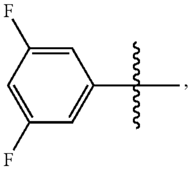,

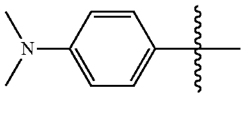, 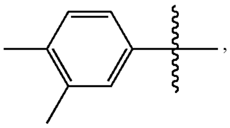,

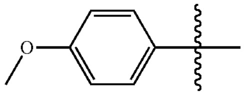,

-continued

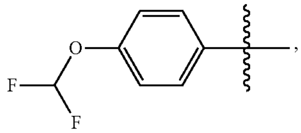,

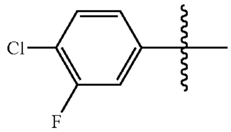, 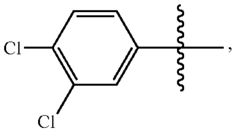,

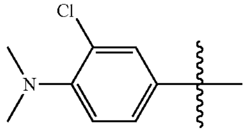, 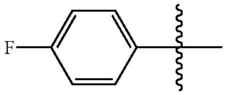,

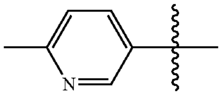, 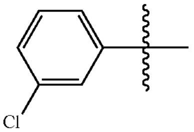,

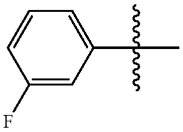, 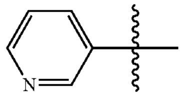,

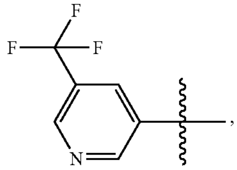, 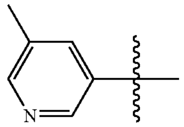,

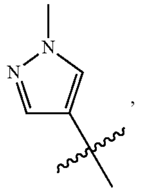, 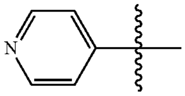, 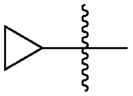,

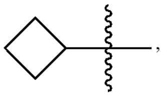, 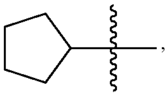,

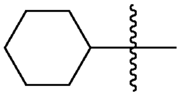, 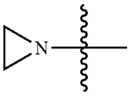, 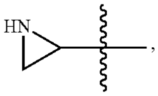,

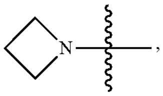, 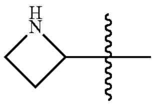, 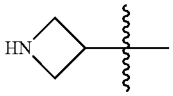,

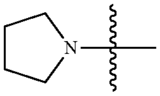, 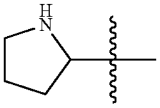,

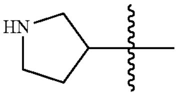, 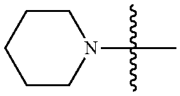,

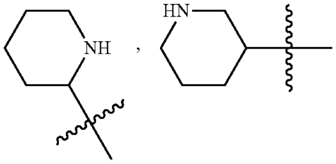,

-continued
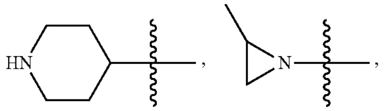
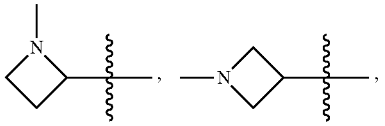
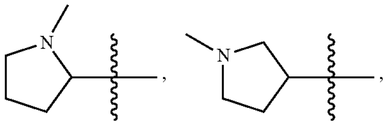
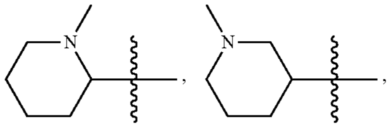
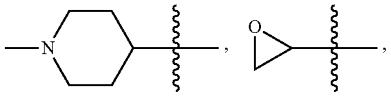
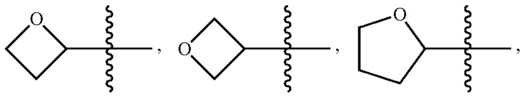
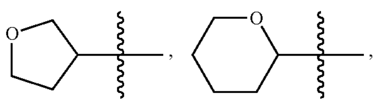
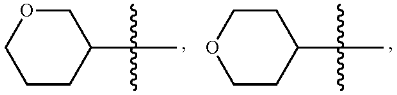
and
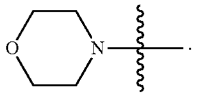
In some embodiments, ring A is chosen from
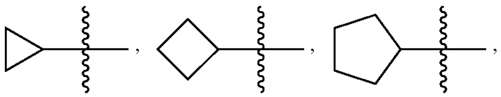
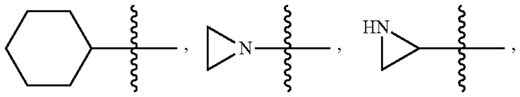
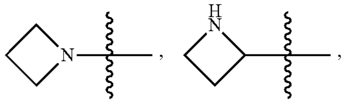
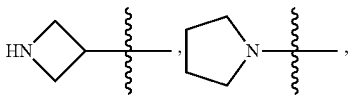
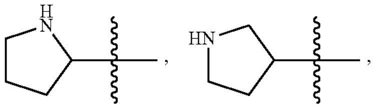
-continued
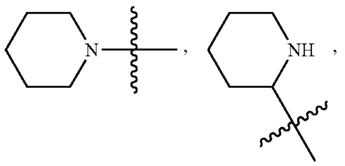
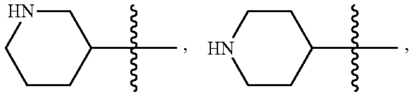
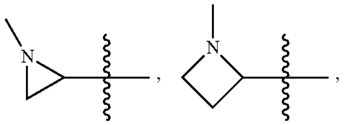
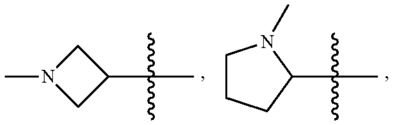
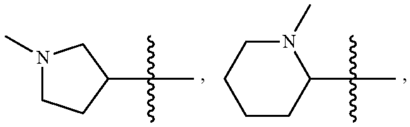
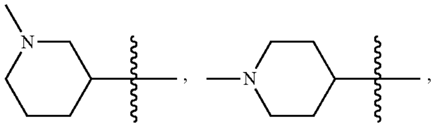
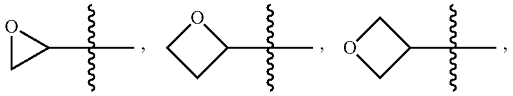
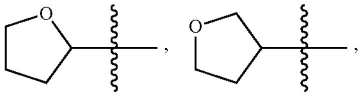
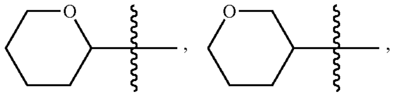
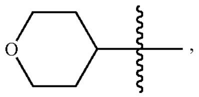
and
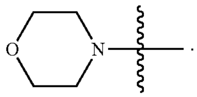
In some embodiments, ring A and ring B, when present, are independently chosen from
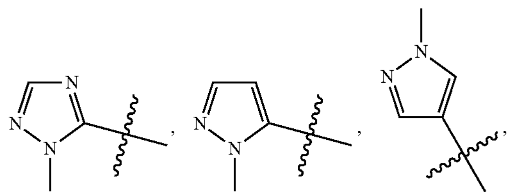
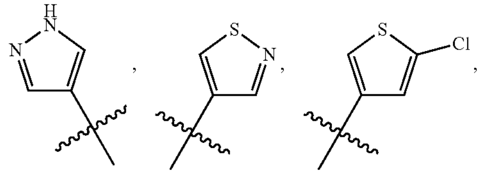

-continued

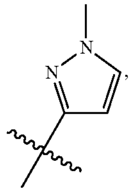,
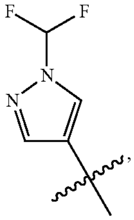,
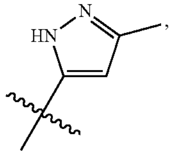,
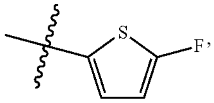,
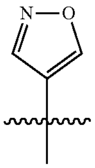,
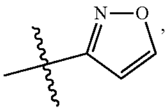,
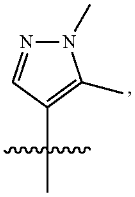,
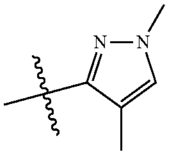,
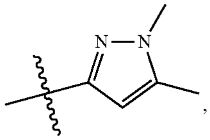,
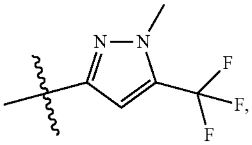,
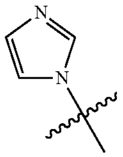,
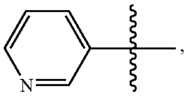,
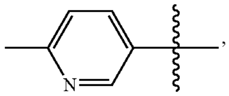,
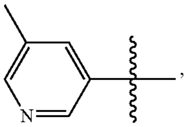,
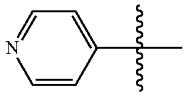,
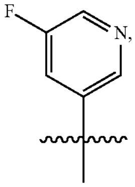
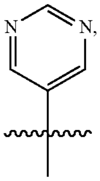
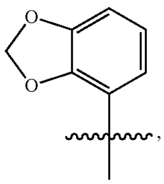,
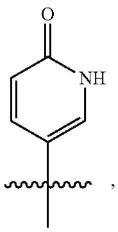,
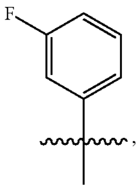,
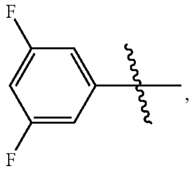,
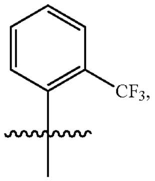
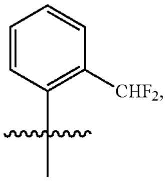

-continued

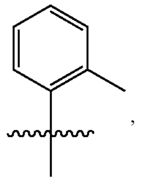,
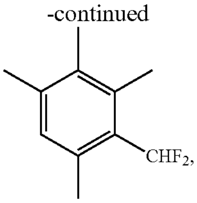
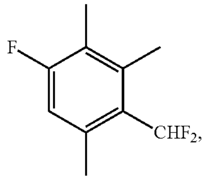
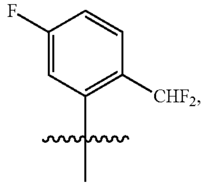
and
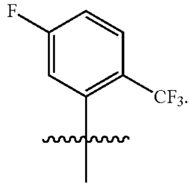

In some embodiments, disclosed herein are compounds of formula (V):

(V)

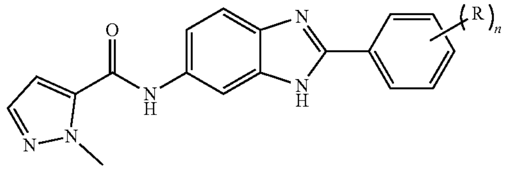

and pharmaceutically acceptable salts thereof, wherein:

n is 0, 1, 2, 3, 4, or 5; and each R is independently chosen from optionally substituted $C_1$-$C_{10}$ alkyls, optionally substituted $C_1$-$C_{10}$ alkoxys, optionally substituted aminos, cyano, halos, hydroxy, and —C(O)H.

In some embodiments, disclosed herein are compounds of formula (VI):

(VI)

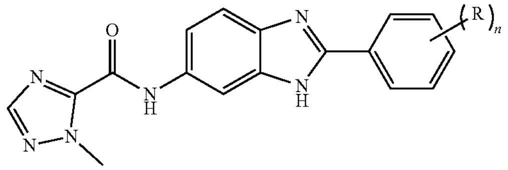

and pharmaceutically acceptable salts thereof, wherein:

n is 0, 1, 2, 3, 4, or 5; and each R is independently chosen from optionally substituted $C_1$-$C_{10}$ alkyls, optionally substituted $C_1$-$C_{10}$ alkoxys, optionally substituted aminos, cyano, halos, hydroxy, and —C(O)H.

In some embodiments, in compounds of formula (III)-(VI), R is chosen from methyl, $—CF_3$, $—CHF_2$, $CH_2F$ and n is an integer chosen from 0-5.

In some embodiments, the present disclosure is drawn to one or more compounds recited in Table 1.

TABLE 1

A

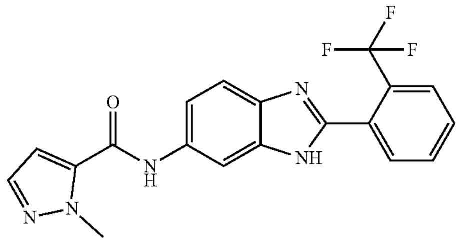 [SMILES: Cn1nccc1C(=O)Nc1ccc2nc(-c3ccccc3C(F)(F)F)[nH]c2c1]

B

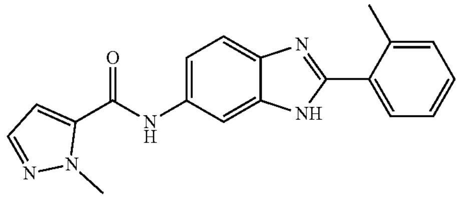 [SMILES: Cc1ccccc1-c1nc2ccc(NC(=O)c3ccnn3C)cc2[nH]1]

G

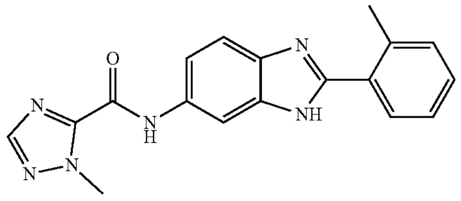

H

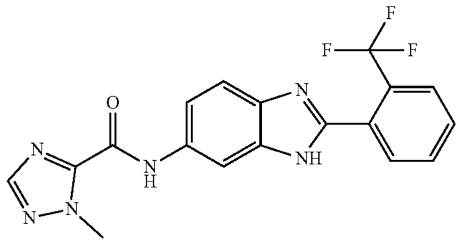 [SMILES: Cn1ncnc1C(=O)Nc1ccc2nc(-c3ccccc3C(F)(F)F)[nH]c2c1]

C

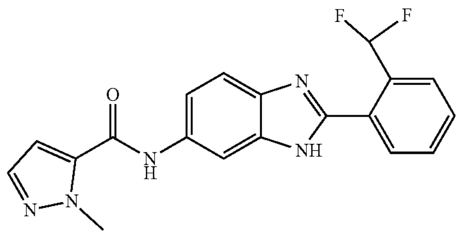 [SMILES: Cn1nccc1C(=O)Nc1ccc2nc(-c3ccccc3C(F)F)[nH]c2c1]

E

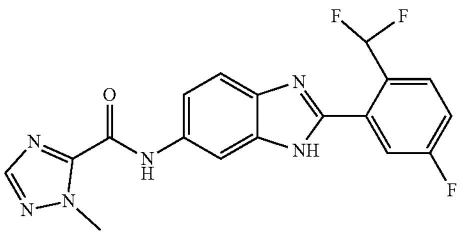

TABLE 1-continued

D

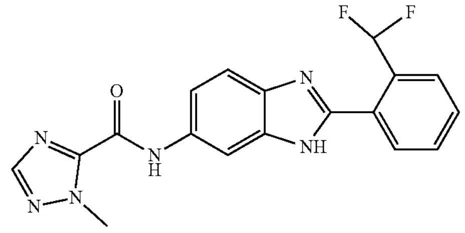 [SMILES: Cn1ncnc1C(=O)Nc1ccc2nc(-c3ccccc3C(F)F)[nH]c2c1]

F

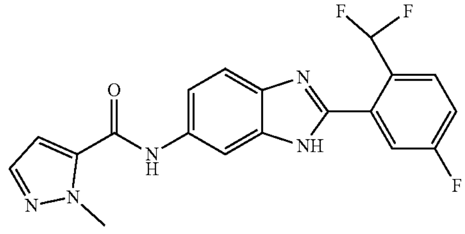 [SMILES: Cn1nccc1C(=O)Nc1ccc2nc(-c3cc(F)ccc3C(F)F)[nH]c2c1]

I

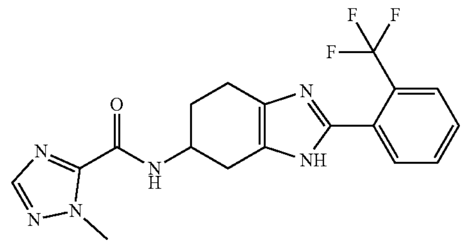 [SMILES: Cn1ncnc1C(=O)NC1CCc2nc(-c3ccccc3C(F)(F)F)[nH]c2C1]

In some embodiments, disclosed herein is at least one entity chosen from the following compounds and pharmaceutically acceptable salts thereof:

N-(2-(2-(difluoromethyl)-5-fluorophenyl)-1H-benzo[d]imidazol-6-yl)-1-methyl-1H-1,2,4-triazole-5-carboxamide;

N-(2-(2-(difluoromethyl)phenyl)-1H-benzo[d]imidazol-6-yl)-1-methyl-1H-1,2,4-triazole-5-carboxamide;

N-(2-(2-(difluoromethyl)-5-fluorophenyl)-1H-benzo[d]imidazol-6-yl)-1-methyl-1H-pyrazole-5-carboxamide;

N-(2-(2-(difluoromethyl)phenyl)-1H-benzo[d]imidazol-6-yl)-1-methyl-1H-pyrazole-5-carboxamide;

1-methyl-N-(2-(2-(trifluoromethyl)phenyl)-1H-benzo[d]imidazol-6-yl)-1H-1,2,4-triazole-5-carboxamide;

1-methyl-N-(2-(o-tolyl)-1H-benzo[d]imidazol-6-yl)-1H-1,2,4-triazole-5-carboxamide;

1-methyl-N-(2-(o-tolyl)-1H-benzo[d]imidazol-6-yl)-1H-pyrazole-5-carboxamide;

1-methyl-N-(2-(2-(trifluoromethyl)phenyl)-1H-benzo[d]imidazol-6-yl)-1H-pyrazole-5-carboxamide; and 1-methyl-N-(2-[2-(trifluoromethyl)phenyl]-4,5,6,7-tetrahydro-1H-1,3-benzodiazol-6-yl)-1H-1,2,4-triazole-5-carboxamide.

The compounds of formulae (I)-(VI) and pharmaceutically acceptable salts thereof can be incorporated into pharmaceutical compositions. In some embodiments, the disclosure is drawn to a pharmaceutical composition comprising at least one entity chosen from compounds of formulae (I)-(VI) and pharmaceutically acceptable salts thereof. In some embodiments, the disclosure is drawn to a pharmaceutical composition consisting essentially of at least one entity chosen from compounds of formulae (I)-(VI) and pharmaceutically acceptable salts thereof.

In some embodiments, the pharmaceutical composition comprises at least one entity chosen from compounds of formulae (I)-(VI) and pharmaceutically acceptable salts thereof and at least one pharmaceutically acceptable excipient. Pharmaceutically acceptable excipients are well-known to persons having ordinary skill in the art and are described in, as a non-limiting example, Remington: The Science and Practice of Pharmacy, 22nd Edition, Lippincott Williams & Wilkins, Philadelphia, Pa. (2013) and any other editions, which are hereby incorporated by reference.

Compounds of the disclosure, pharmaceutically acceptable salts thereof, and/or pharmaceutical compositions comprising said at least one entity chosen from compounds of formulae (I)-(VI) and pharmaceutically acceptable salts thereof can be used in therapeutic treatments.

The compounds, pharmaceutically acceptable salts, and/or pharmaceutical compositions can be administered in unit forms of administration to mammalian subjects, including human beings. Suitable non-limiting examples of unit forms of administration include orally administered forms and forms administered via a parenteral/systemic route, non-limiting examples of which including inhalation, subcutaneous administration, intramuscular administration, intravenous administration, intradermal administration, and intravitreal administration.

In some embodiments, pharmaceutical compositions suitable for oral administration can be in the form of tablets, pills, powders, hard gelatine capsules, soft gelatine capsules, and/or granules. In some embodiments of such pharmaceutical compositions, a compound of the disclosure and/or a pharmaceutically acceptable salt of a compound of the disclosure is (or are) mixed with one or more inert diluents, non-limiting examples of which including starch, cellulose, sucrose, lactose, and silica. In some embodiments, such pharmaceutical compositions may further comprise one or more substances other than diluents, such as (as non-limiting examples), lubricants, coloring agents, coatings, or varnishes.

In some embodiments, pharmaceutical compositions for parenteral administration can be in the form of aqueous solutions, non-aqueous solutions, suspensions, emulsions, drops, or any combination(s) thereof. In some embodiments, such pharmaceutical compositions may comprise one or more of water, pharmaceutically acceptable glycol(s), pharmaceutically acceptable oil(s), pharmaceutically acceptable organic esters, or other pharmaceutically acceptable solvents.

In some embodiments, disclosed herein is a method of inhibiting AhR comprising administering to a subject in need thereof at least one entity chosen from compounds of formulae (I)-(VI) and pharmaceutically acceptable salts thereof. In some embodiments, disclosed herein is a method of reducing the activity of AhR comprising administering to a subject in need thereof at least one entity chosen from compounds of formulae (I)-(VI) and pharmaceutically acceptable salts thereof.

In some embodiments, disclosed herein is a method of treating a cancer comprising administering to a subject in need thereof at least one entity chosen from compounds of formulae (I)-(VI) and pharmaceutically acceptable salts thereof. In some embodiments, the cancers are chosen from liquid tumors and solid tumors. In some embodiments, the cancer is chosen from breast cancers, respiratory tract cancers, brain cancers, cancers of reproductive organs, digestive tract cancers, urinary tract cancers, eye cancers, liver cancers, skin cancers, head and neck cancers, thyroid cancers, parathyroid cancers, and metastases of any of the foregoing. In some embodiments, the cancers are chosen from breast cancers, pancreatic cancers, prostate cancers, and colon cancers. In some embodiments, the cancers are chosen from lymphomas, sarcomas, and leukemias.

In some embodiments, disclosed herein is a method of treating a disease or condition mediated by AhR signaling in a subject in need thereof comprising administering to the subject a therapeutically effective amount of at least one entity chosen from the compounds of formulae (I)-(VI) and pharmaceutically acceptable salts thereof, or at least one pharmaceutical composition comprising the at least one entity. In some embodiments, disclosed herein is a method of treating a disease or condition associated with aberrant AhR signaling in a subject in need thereof comprising administering to the subject a therapeutically effective amount of at least one entity chosen from the compounds of formulae (I)-(VI) and pharmaceutically acceptable salts thereof, or at least one pharmaceutical composition comprising the at least one entity.

In some embodiments, the disease is chosen from cancers. In some embodiments, the disease is chosen from liquid tumors and solid tumors. In some embodiments, the disease is chosen from breast cancers, respiratory tract cancers, brain cancers, cancers of reproductive organs, digestive tract cancers, urinary tract cancers, eye cancers, liver cancers, skin cancers, head and neck cancers, thyroid cancers, parathyroid cancers, and metastases of any of the foregoing. In some embodiments, the disease is chosen from breast cancers, pancreatic cancers, prostate cancers, and colon cancers. In some embodiments, the disease is chosen from lymphomas, sarcomas, melanomas, glioblastomas, and leukemias.

In some embodiments, the methods disclosed herein may further comprise administering to the subject a therapeutically effective amount of at least one immune checkpoint inhibitor. In some embodiments, the immune checkpoint inhibitor is chosen from PD-1 inhibitors, PD-L1 inhibitors, and CTLA-4 blockers.

In some embodiments, disclosed herein is a method of inhibiting cancer cell proliferation mediated by AhR signaling in a subject in need thereof comprising administering to the subject a therapeutically effective amount of at least one entity chosen from the compounds of formulae (I)-(VI) and pharmaceutically acceptable salts thereof, or at least one pharmaceutical composition comprising the at least one entity.

In some embodiments, disclosed herein is a method of inhibiting tumor cell invasion or metastasis mediated by AhR signaling in a subject in need thereof comprising administering to the subject a therapeutically effective amount of at least one entity chosen from the compounds of formulae (I)-(VI) and pharmaceutically acceptable salts thereof, or at least one pharmaceutical composition comprising the at least one entity.

With regard to the methods disclosed herein, the mode (or modes) of administration, dose (or doses), and pharmaceutical form (or forms) can be determined according to criteria generally considered during the establishment of a treatment of a patient, such as, by way of non-limiting examples, the potency of the compound(s) and/or pharmaceutically acceptable salts of the compound(s), the age of the patient, the body weight of the patient, the severity of the patient's condition (or conditions), the patient's tolerance to the treatment, and secondary effects observed in treatment. Determination of doses effective to provide therapeutic benefit for specific modes and frequency of administration is within the capabilities of those skilled in the art.

In some embodiments, a compound of formulae (I)-(VI) and/or pharmaceutically acceptable salt thereof is present in a pharmaceutical composition in an amount ranging from 5

μg to 2,000 mg. In some embodiments, a compound of the disclosure and/or pharmaceutically acceptable salt thereof is present in a pharmaceutical composition in an amount ranging from 5 μg to 1,000 mg. In some embodiments, a compound of the disclosure and/or pharmaceutically acceptable salt thereof is present in a pharmaceutical composition in an amount ranging from 5 μg to 500 mg. In some embodiments, a compound of the disclosure and/or pharmaceutically acceptable salt thereof is present in a pharmaceutical composition in an amount ranging from 5 μg to 250 mg. In some embodiments, a compound of the disclosure and/or pharmaceutically acceptable salt thereof is present in a pharmaceutical composition in an amount ranging from 5 μg to 100 mg. In some embodiments, a compound of the disclosure and/or pharmaceutically acceptable salt thereof is present in a pharmaceutical composition in an amount ranging from 5 μg to 50 mg.

In some embodiments, a compound of the disclosure and/or pharmaceutically acceptable salt thereof is present in a pharmaceutical composition in an amount ranging from 1 mg to 5,000 mg. In some embodiments, a compound of the disclosure and/or pharmaceutically acceptable salt thereof is present in a pharmaceutical composition in an amount ranging from 1 mg to 3,000 mg. In some embodiments, a compound of the disclosure and/or pharmaceutically acceptable salt thereof is present in a pharmaceutical composition in an amount ranging from 1 mg to 2,000 mg. In some embodiments, a compound of the disclosure and/or pharmaceutically acceptable salt thereof is present in a pharmaceutical composition in an amount ranging from 1 mg to 1,000 mg. In some embodiments, a compound of the disclosure and/or pharmaceutically acceptable salt thereof is present in a pharmaceutical composition in an amount ranging from 1 mg to 500 mg. In some embodiments, a compound of the disclosure and/or pharmaceutically acceptable salt thereof is present in a pharmaceutical composition in an amount ranging from 1 mg to 250 mg. In some embodiments, a compound of the disclosure and/or pharmaceutically acceptable salt thereof is present in a pharmaceutical composition in an amount ranging from 1 mg to 100 mg. In some embodiments, a compound of the disclosure and/or pharmaceutically acceptable salt thereof is present in a pharmaceutical composition in an amount ranging from 1 mg to 50 mg.

In some embodiments, a compound of the disclosure and/or pharmaceutically acceptable salt thereof is present in a pharmaceutical composition in an amount of 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 125 mg, 150 mg, 175 mg, 200 mg, 225 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1,000 mg, 1,100 mg, 1,200 mg, 1,300 mg, 1,400 mg, 1,500 mg, 1,600 mg, 1,700 mg, 1,800 mg, 1,900 mg, 2,000 mg, 2,100 mg, 2,200 mg, 2,300 mg, 2,400 mg, 2,500 mg, 2,600 mg, 2,700 mg, 2,800 mg, 2,900 mg, 3,000 mg, 3,100 mg, 3,200 mg, 3,300 mg, 3,400 mg, 3,500 mg, 3,600 mg, 3,700 mg, 3,800 mg, 3,900 mg, 4,000 mg, 4,100 mg, 4,200 mg, 4,300 mg, 4,400 mg, 4,500 mg, 4,600 mg, 4,700 mg, 4,800 mg, 4,900 mg, or 5,000 mg.

Effective amounts and dosages can be estimated initially from in vitro assays. For example, an initial dosage for use in animals can be formulated to achieve a circulating blood or serum concentration of active compound that is at or above an $IC_{50}$ of the particular compound as measured in an in vitro assay. Calculating dosages to achieve such circulating blood or serum concentrations taking into account the bioavailability of the particular compound is well within the capabilities of skilled artisans. For guidance, the reader is referred to Fingl & Woodbury, "General Principles," in *Goodman and Gilman's The Pharmaceutical Basis of Therapeutics*, Chapter 1, pp. 1-46, latest edition, Pergamagon Press, and the references cited therein, which methods are incorporated herein by reference in their entirety. Initial dosages can also be estimated from in vivo data, such as animal models. Animal models useful for testing the efficacy of compounds to treat or prevent the various diseases described in this disclosure are well-known in the art.

In some embodiments, the administered dose ranges from 0.0001 or 0.001 or 0.01 mg/kg/day to 100 mg/kg/day, but can be higher or lower, depending upon, among other factors, the activity of the compound, its bioavailability, the mode of administration and various factors discussed above. Doses and intervals can be adjusted individually to provide plasma levels of the compound(s) which are sufficient to maintain therapeutic or prophylactic effect. For example, the compounds can be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Non-limiting embodiments of the present disclosure include:

1. A compound of Formula I

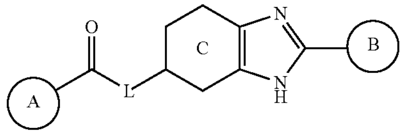

(I)

or a pharmaceutically acceptable salt thereof, wherein:

ring A is chosen from optionally substituted 5-10 membered aryls, optionally substituted 4-10 membered heteroaryls, optionally substituted 3-10 membered cycloalkyls, and optionally substituted 3-10 membered heterocycloalkyls;

ring B is chosen from optionally substituted 5-10 membered aryls, optionally substituted 4-10 membered heteroaryls, optionally substituted 3-10 membered cycloalkyls, and optionally substituted 3-10 membered heterocycloalkyls;

ring C is chosen from optionally substituted cyclohexenyls and optionally substituted phenyls; and L is chosen from divalent linking groups, provided that ring B is not

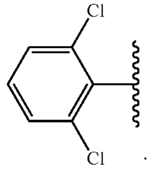 [SMILES: *c1c(Cl)cccc1Cl]

.

2. The compound of embodiment 1, or a pharmaceutically acceptable salt thereof, wherein the compound is chosen from compounds of formula (II):

(II)

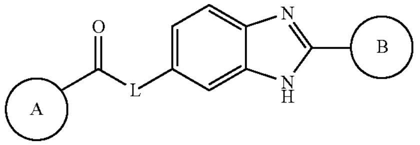

and pharmaceutically acceptable salts thereof, wherein:

ring A is chosen from optionally substituted 5-10 membered aryls, optionally substituted 4-10 membered heteroaryls, optionally substituted 3-10 membered cycloalkyls, and optionally substituted 3-10 membered heterocycloalkyls;

ring B is chosen from optionally substituted 5-10 membered aryls, optionally substituted 4-10 membered heteroaryls, optionally substituted 3-10 membered cycloalkyls, and optionally substituted 3-10 membered heterocycloalkyls; and L is chosen from divalent linking groups, provided that ring B is not

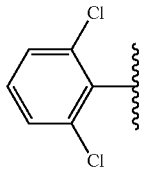

.

3. The compound of any one of embodiments 1 and 2, or a pharmaceutically acceptable salt thereof, wherein the compound is chosen from compounds of formula (III):

(III)

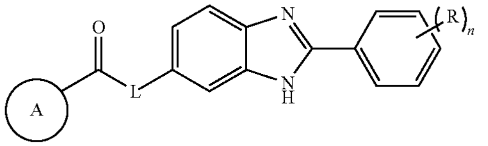

and pharmaceutically acceptable salts thereof, wherein:

ring A is chosen from optionally substituted 5-10 membered aryls, optionally substituted 4-10 membered heteroaryls, optionally substituted 3-10 membered cycloalkyls, and optionally substituted 3-10 membered heterocycloalkyls;

L is chosen from divalent linking groups;

n is 0, 1, 2, 3, 4, or 5; and each R is independently chosen from optionally substituted $C_1$-$C_{10}$ alkyls, optionally substituted $C_1$-$C_{10}$ alkoxys, optionally substituted aminos, cyano, halos, hydroxy, and —C(O)H.

4. The compound of any one of embodiments 1-3, or a pharmaceutically acceptable salt thereof, wherein the compound is chosen from compounds of formula (IV):

(IV)

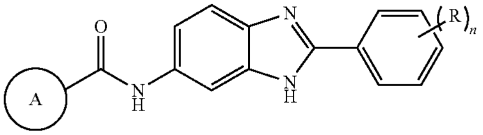

and pharmaceutically acceptable salts thereof, wherein:

ring A is chosen from optionally substituted 5-10 membered aryls, optionally substituted 4-10 membered heteroaryls, optionally substituted 3-10 membered cycloalkyls, and optionally substituted 3-10 membered heterocycloalkyls;

n is 0, 1, 2, 3, 4, or 5; and each R is independently chosen from optionally substituted $C_1$-$C_{10}$ alkyls, optionally substituted $C_1$-$C_{10}$ alkoxys, optionally substituted aminos, cyano, halos, hydroxy, and —C(O)H.

5. The compound of any one of embodiments 1-4, or a pharmaceutically acceptable salt thereof, wherein the compound is chosen from compounds of formula (V):

(V)

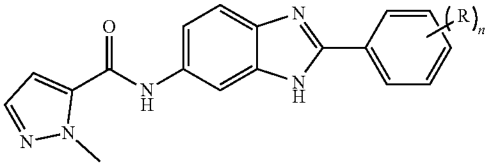

and pharmaceutically acceptable salts thereof, wherein:

n is 0, 1, 2, 3, 4, or 5; and each R is independently chosen from optionally substituted $C_1$-$C_{10}$ alkyls, optionally substituted $C_1$-$C_{10}$ alkoxys, optionally substituted aminos, cyano, halos, hydroxy, and —C(O)H.

6. The compound of any one of embodiments 1-4, or a pharmaceutically acceptable salt thereof, wherein the compound is chosen from compounds of formula (VI):

(VI)

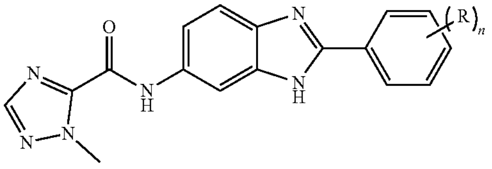

and pharmaceutically acceptable salts thereof, wherein:

n is 0, 1, 2, 3, 4, or 5; and each R is independently chosen from optionally substituted $C_1$-$C_{10}$ alkyls, optionally substituted $C_1$-$C_{10}$ alkoxys, optionally substituted aminos, cyano, halos, hydroxy, and —C(O)H.

7. The compound of any one of embodiments 1-4, or a pharmaceutically acceptable salt thereof, wherein:
ring A is chosen from 5-10 membered aryls, 4-10 membered heteroaryls, 3-10 membered cycloalkyls, and 3-10 membered heterocycloalkyls, wherein each 5-10 membered aryl, 4-10 membered heteroaryl, 3-10 membered cycloalkyl, and 3-10 membered heterocycloalkyl is independently optionally substituted with 1 to 5 instances of $R^A$; and
each $R^A$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and —NR"R", wherein each R" is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls.

8. The compound of embodiment any one of embodiments 1-4, or a pharmaceutically acceptable salt thereof, wherein ring A is chosen from 5-8 membered heteroaryls optionally substituted with 1 to 4 instances of $R^A$.

9. The compound of one of embodiments 1-4, or a pharmaceutically acceptable salt thereof, wherein ring A is chosen from 5-8 membered aryls optionally substituted with 1 to 4 instances of $R^A$.

10. The compound of one of embodiments 1-4, or a pharmaceutically acceptable salt thereof, wherein ring A is chosen from 4-8 membered cycloalkyls optionally substituted with 1 to 4 instances of $R^A$.

11. The compound of one of embodiments 1-4, or a pharmaceutically acceptable salt thereof, wherein ring A is chosen from pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl,
wherein each of pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl is independently optionally substituted with 1 to 3 instances of $R^A$.

12. The compound of one of embodiments 1-4 and 11, or a pharmaceutically acceptable salt thereof, wherein ring A is chosen from pyrazolyl optionally substituted with 1 to 3 instances of $R^A$ and triazolyl rings optionally substituted with 1 to 2 instances of $R^A$.

13. The compound of any one of embodiments 1-4, or a pharmaceutically acceptable salt thereof, wherein rings A and B are independently chosen from

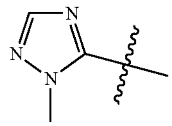, 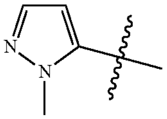, 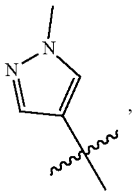,

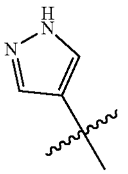, 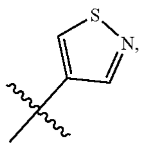 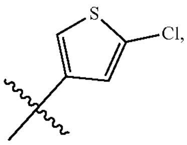

-continued

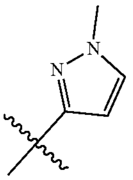, 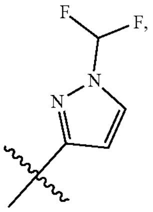 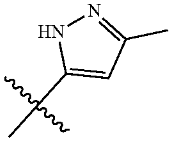,

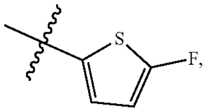 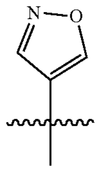, 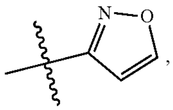,

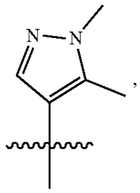, 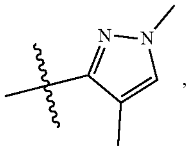, 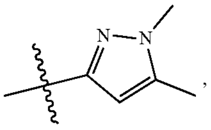,

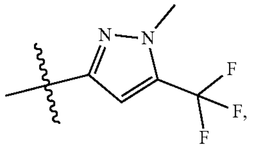 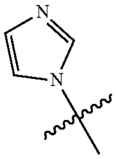,

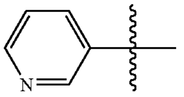, 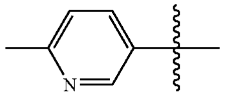,

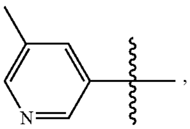, 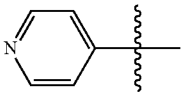, 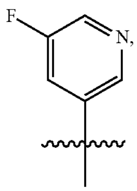

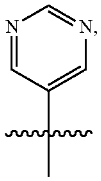 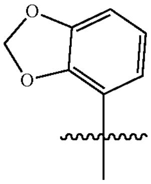, 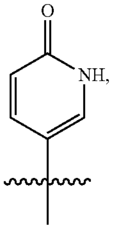

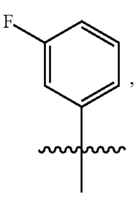, 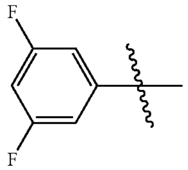, 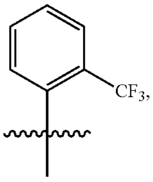

-continued
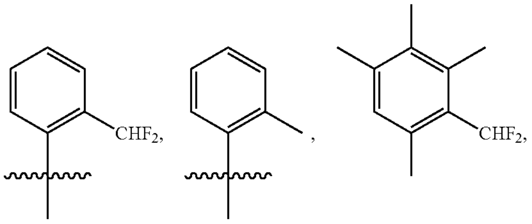
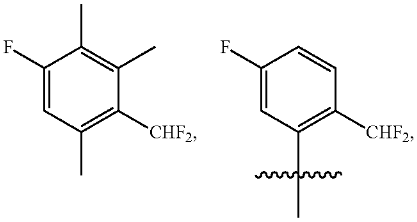
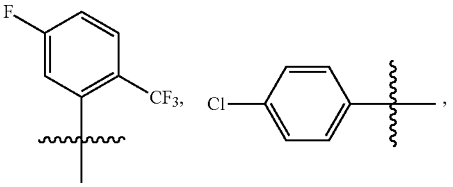
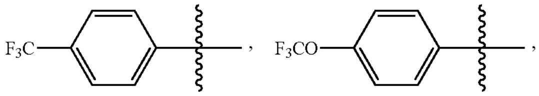
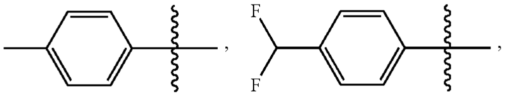
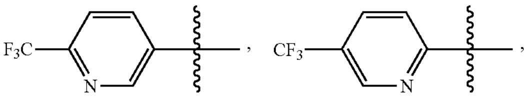
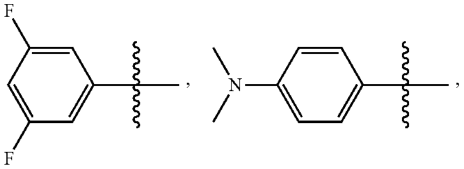
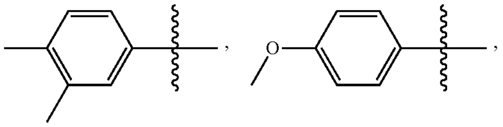
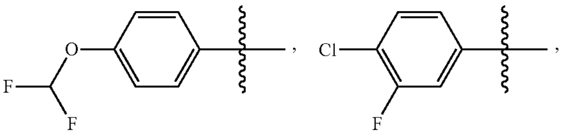
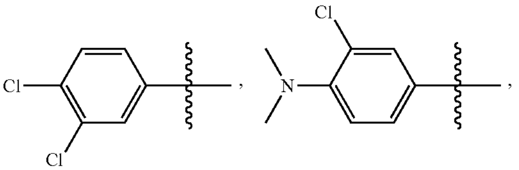
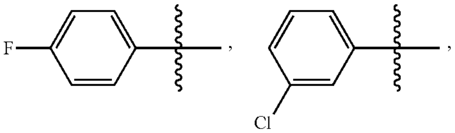
-continued
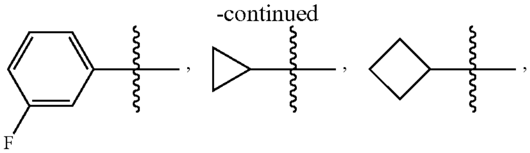
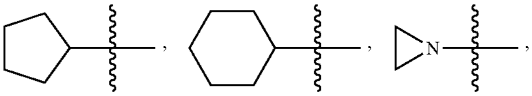
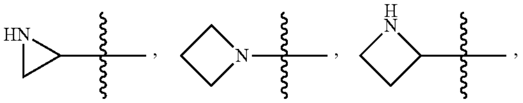
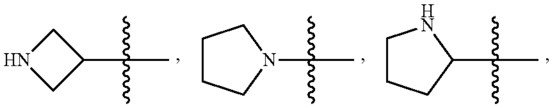
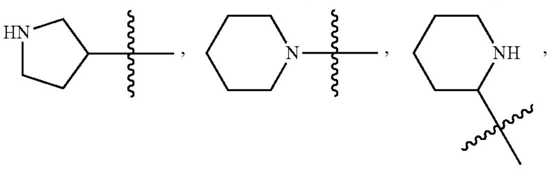
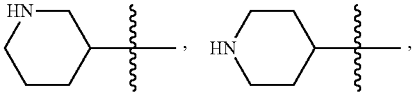
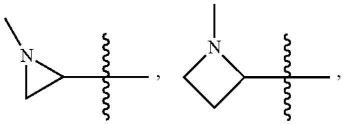
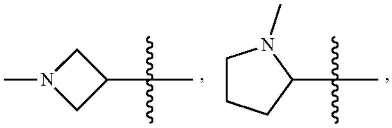
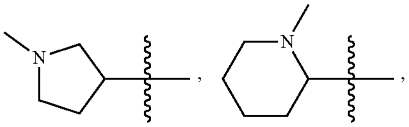
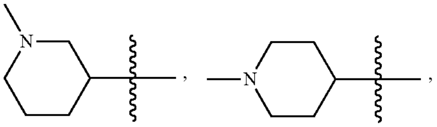
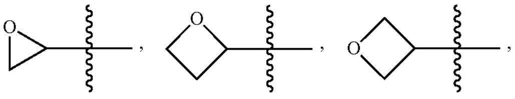
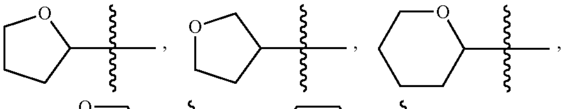
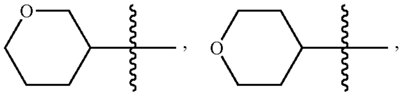
and
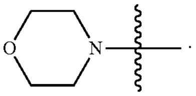
14. The compound of any one of embodiments 1, 2, and 7-13, or a pharmaceutically acceptable salt thereof, wherein:

ring B is chosen from optionally substituted 6-10 membered aryls, optionally substituted 5-10 membered heteroaryls, optionally substituted 3-10 membered cycloalkyls, and optionally substituted 3-10 membered heterocycloalkyls.

15. The compound of any one of embodiments 1, 2, and 7-14, or a pharmaceutically acceptable salt thereof, wherein ring B is chosen from 6-8 membered aryls optionally substituted with 1 to 5 instances of $R^B$.

16. The compound of any one of embodiments 1, 2, and 7-15, or a pharmaceutically acceptable salt thereof, wherein ring B is phenyl optionally substituted with 1 to 3 instances of $R^B$.

17. The compound of any one of embodiments 1, 2, and 7-14, or a pharmaceutically acceptable salt thereof, wherein ring B is chosen from 6-8 membered heteroaryls optionally substituted with 1 to 5 instances of $R^B$.

18. The compound of any one of embodiments 1, 2, 7-14, and 17, or a pharmaceutically acceptable salt thereof, wherein ring B is chosen from benzodioxolyl, pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, pyridinonyl, and pyrimidinyl, wherein each of benzodioxolyl, pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl is independently optionally substituted with 1 to 3 instances of $R^B$.

19. The compound of any one of embodiments 1-3 and 7-18, or a pharmaceutically acceptable salt thereof, wherein:

L is chosen from $C_1$-$C_5$ alkyl divalent linking groups, $C_1$-$C_5$ heteroalkyl divalent linking groups, —O—, $C_1$-$C_5$ alkoxy divalent linking groups, —NH—, substituted divalent amines, $C_1$-$C_5$ amino divalent linking groups, —S—, and $C_1$-$C_5$ thio divalent linking groups.

20. The compound of any one of embodiments 1-3, and 7-18, or a pharmaceutically acceptable salt thereof, wherein L is chosen from —NH— and substituted divalent amines of formula —NR'—, wherein R' is chosen from halos, $C_1$-$C_{10}$ alkyls, $C_1$-$C_{10}$ haloalkyls, $C_1$-$C_{10}$ alkoxys, and $C_1$-$C_{10}$ haloalkoxys.

21. The compound of any one of embodiments 3-20, or a pharmaceutically acceptable salt thereof, wherein n is 1 or 2.

22. The compound of any one of embodiments 3-21, or a pharmaceutically acceptable salt thereof, wherein each R is independently chosen from halos, optionally substituted $C_1$-$C_{10}$ alkyls, and optionally substituted $C_1$-$C_{10}$ alkoxys.

23. The compound of any one of embodiments 3-22, or a pharmaceutically acceptable salt thereof, wherein each R is independently chosen from halos and optionally substituted $C_1$-$C_5$ alkyls.

24. The compound of any one of embodiments 3-22, or a pharmaceutically acceptable salt thereof, wherein each R is independently chosen from optionally substituted $C_1$ alkyls.

25. The compound of any one of embodiments 3-24, or a pharmaceutically acceptable salt thereof, wherein each R is independently chosen from methyl and halogenated methyls.

26. The compound of any one of embodiments 3-25, or a pharmaceutically acceptable salt thereof, wherein each R is independently chosen from fluoro, methyl, monofluoromethyl, difluoromethyl, and trifluoromethyl.

27. At least one entity chosen from the following compounds and pharmaceutically acceptable salts thereof.

N-(2-(2-(difluoromethyl)-5-fluorophenyl)-1H-benzo[d]imidazol-6-yl)-1-methyl-1H-1,2,4-triazole-5-carboxamide;

N-(2-(2-(difluoromethyl)phenyl)-1H-benzo[d]imidazol-6-yl)-1-methyl-1H-1,2,4-triazole-5-carboxamide;

N-(2-(2-(difluoromethyl)-5-fluorophenyl)-1H-benzo[d]imidazol-6-yl)-1-methyl-1H-pyrazole-5-carboxamide;

N-(2-(2-(difluoromethyl)phenyl)-1H-benzo[d]imidazol-6-yl)-1-methyl-1H-pyrazole-5-carboxamide;

1-methyl-N-(2-(2-(trifluoromethyl)phenyl)-1H-benzo[d]imidazol-6-yl)-1H-1,2,4-triazole-5-carboxamide;

1-methyl-N-(2-(o-tolyl)-1H-benzo[d]imidazol-6-yl)-1H-1,2,4-triazole-5-carboxamide;

1-methyl-N-(2-(o-tolyl)-1H-benzo[d]imidazol-6-yl)-1H-pyrazole-5-carboxamide;

1-methyl-N-(2-(2-(trifluoromethyl)phenyl)-1H-benzo[d]imidazol-6-yl)-1H-pyrazole-5-carboxamide; and 1-methyl-N-(2-[2-(trifluoromethyl)phenyl]-4,5,6,7-tetrahydro-11H-1,3-benzodiazol-6-yl)-1H-1,2,4-triazole-5-carboxamide.

28. A pharmaceutical composition comprising at least one entity chosen from the compounds of any one of embodiments 1 to 27 and pharmaceutically acceptable salts thereof, and at least one pharmaceutically acceptable excipient.

29. A method of treating a disease or condition mediated by AhR signaling in a subject in need thereof comprising administering to the subject a therapeutically effective amount of at least one entity chosen from the compounds of any one of embodiments 1 to 27 and pharmaceutically acceptable salts thereof, or at least one pharmaceutical composition of embodiment 28.

30. A method of treating a disease or condition associated with aberrant AhR signaling in a subject in need thereof comprising administering to the subject a therapeutically effective amount of at least one entity chosen from the compounds of any one of embodiments 1 to 27 and pharmaceutically acceptable salts thereof, or at least one pharmaceutical composition of embodiment 28.

31. The method of embodiment 29 or 30, wherein the disease is chosen from cancers.

32. The method of embodiment 29 or 30, wherein the disease is chosen from liquid tumors and solid tumors.

33. The method of any one of embodiments 29 to 32, wherein the disease is chosen from breast cancers, respiratory tract cancers, brain cancers, cancers of reproductive organs, digestive tract cancers, urinary tract cancers, eye cancers, liver cancers, skin cancers, head and neck cancers, thyroid cancers, parathyroid cancers, and metastases of any of the foregoing.

34. The method of any one of embodiments 29 to 33, wherein the disease is chosen from breast cancers, pancreatic cancers, prostate cancers, and colon cancers.

35. The method of any one of embodiments 29 to 33, wherein the disease is chosen from lymphomas, sarcomas, melanomas, glioblastomas, and leukemias.

36. The method of any one of embodiments 29 to 35, further comprising administering to the subject a therapeutically effective amount of at least one immune checkpoint inhibitor.

37. The method of embodiment 36, wherein the immune checkpoint inhibitor is chosen from PD-1 inhibitors, PD-L1 inhibitors, and CTLA-4 blockers.

38. A method of inhibiting cancer cell proliferation mediated by AhR signaling in a subject in need thereof comprising administering to the subject a therapeutically effective amount of at least one entity chosen from the compounds of any one of embodiments 1 to 27 and pharmaceutically acceptable salts thereof, or at least one pharmaceutical composition of embodiment 28.

39. A method of inhibiting tumor cell invasion or metastasis mediated by AhR signaling in a subject in need thereof comprising administering to the subject a therapeutically effective amount of at least one entity chosen from the compounds of any one of embodiments 1 to 27 and pharmaceutically acceptable salts thereof, or at least one pharmaceutical composition of embodiment 28.

EXAMPLES

The following non-limiting examples and data illustrate various aspects and features relating to the compounds and/or methods of the present disclosure, including the preparation of various compounds, as are available through the synthetic methodologies described herein. In comparison with the prior art, in some embodiments, the present compounds and/or methods provide results and data which are surprising, unexpected and contrary thereto. While the utility of this disclosure is illustrated through the use of several compounds and moieties/groups which can be used therewith, it will be understood by those skilled in the art that comparable results are obtainable with various other compounds, moieties and/or groups, as are commensurate with the scope of this disclosure.

Example 1. Synthesis of Compounds A-H

Preparation of 1-methyl-N-(2-(2-(trifluoromethyl)phenyl)-1H-benzo[d]imidazol-6-yl)-1H-pyrazole-5-carboxamide (A)

Preparation of 6-nitro-2-(2-(trifluoromethyl)phenyl)-1H-benzo[d]imidazole (3)

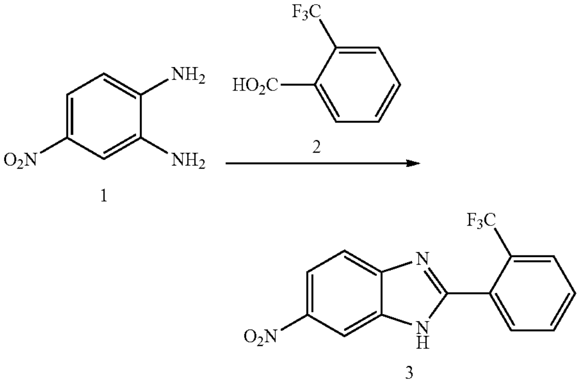

A mixture of 4-nitrobenzene-1,2-diamine (1, 5.0 g, 32.65 mmol) and 2-(trifluoromethyl)benzoic acid (2, 5.64 g, 29.68 mmol) in polyphosphoric acid (60 mL) heated at 120° C. was stirred for 5 hours under nitrogen atmosphere. The mixture was cooled to 25° C., water (150 mL) was added and the pH was adjusted to 6.0 with saturated aqueous NaOH. The solid material was collected by filtration, washed thoroughly with water (30 mL) and recrystallized from ethyl acetate (30 mL) to provide the title compound (3, 4.9 g, 15.95 mmol, 53.73% yield). $^1$H-NMR ($CH_3OH-d_4$, 400 MHz): δH 8.59 (1H, s), 8.28 (1H, dd, J=2.0 Hz, J=9.2 Hz), 7.95-7.97 (1H, m), 7.78-7.85 (4H, m).

Preparation of 2-(2-(trifluoromethyl)phenyl)-1H-benzo[d]imidazol-6-amine (4)

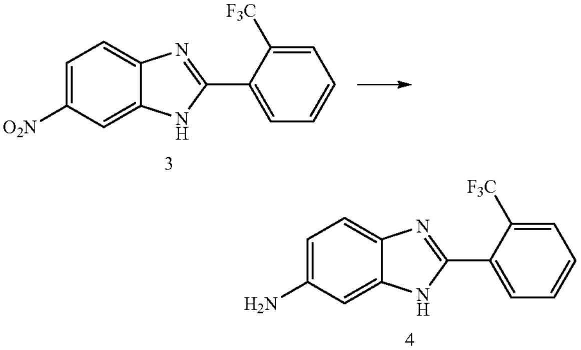

A mixture of 6-nitro-2-(2-(trifluoromethyl)phenyl)-1H-benzo[d]imidazole (3, 4.9 g, 15.95 mmol), Pd/C (1 g, 10% purity) in MeOH (200 mL) was degassed, purged with hydrogen for 3 times and then stirred under hydrogen (15 psi) for 12 hours at 25° C. The mixture was filtered through celite and the solvent was removed under reduced pressure to afford the crude material that was then triturated with petroleum ether (30 mL) and ethyl acetate (30 mL). The remaining cake was dried under reduced pressure to afford the crude product of the title compound (4, 3 g, 10.82 mmol, 67.85% yield). $^1$H-NMR (CHCl3-d, 400 MHz): δH 9.34 (1H, s), 8.04 (1H, d, J=8.0 Hz), 7.81 (1H, d, J=8.0 Hz), 7.67 (1H, t, J=7.2 Hz), 7.58 (1H, t, J=7.6 Hz), 6.74 (2H, d, J=8.4 Hz), 3.75 (2H, s), 1.65 (1H, s).

Preparation of 1-methyl-1H-pyrazole-5-carbonyl Chloride (7)

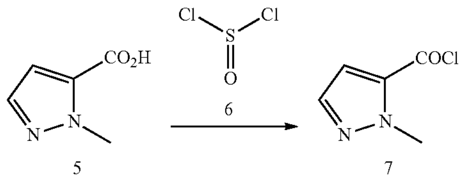

To a solution of 1-methyl-1H-pyrazole-5-carboxylic acid (5, 1 g, 7.93 mmol) and $SOCl_2$ (943.36 mg, 7.93 mmol, 575.22 μL) in DCM (20 mL), two drops of DMF (28.98 mg, 396.47 μmol, 30.50 μL) were added. The mixture was degassed and purged with nitrogen for 3 times and stirred at 60° C. for 2 hours under nitrogen atmosphere. The reaction mixture was concentrated under reduced pressure to afford the crude material of the title compound (7, 0.8 g).

Preparation of 1-methyl-N-(2-(2-(trifluoromethyl)phenyl)-1H-benzo[d]imidazol-6-yl)-1H-pyrazole-5-carboxamide (A)

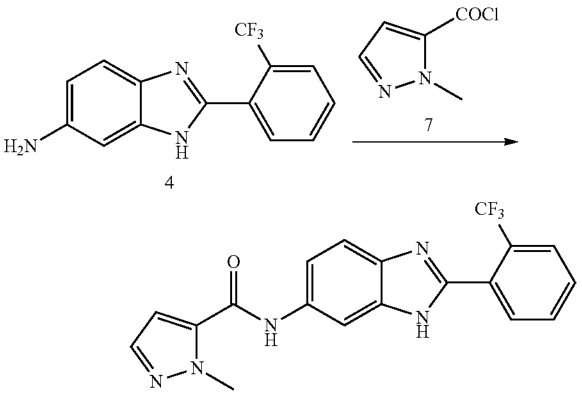
4
7
A

A mixture of 2-(2-(trifluoromethyl)phenyl)-1H-benzo[d]imidazol-6-amine (4, 1.5 g, 5.41 mmol), 1-methyl-1H-pyrazole-5-carbonyl chloride (7, 800 mg, 5.53 mmol) and TEA (547.48 mg, 5.41 mmol, 753.06 μL) in DCM (20 mL) was degassed, purged with nitrogen for 3 times and then was stirred at 25° C. for 8 hours under nitrogen atmosphere. The solvent was evaporated and the residue was taken up in ethyl acetate (20 mL), washed with saturated aqueous sodium bicarbonate (10 mL), dried over anhydrous sodium sulfate, filtered and evaporated. The residue was purified by column chromatography ($SiO_2$, Petroleum ether/Ethyl acetate=5/1 to 0/1) and then washed with the mixture of water (20 mL) and methyl alcohol (20 mL). The remaining solid was freeze-dried to provide the title compound (A, 1.33 g, 3.42 mmol, 63.16% yield). $^1$H-NMR (DMSO-$d_6$, 400 MHz): δH 12.73 (1H, s), 10.25 (1H, d, J=24.8 Hz), 8.12 (1H, d, J=27.2 Hz), 7.76-7.87 (3H, m), 7.56 (1H, dd, J=8.8 Hz, J=82.8 Hz), 7.55 (2H, s), 7.09 (1H, s), 4.11 (3H, s); MS (m/z): 386.1 $[M+H]^+$; purity 99%.

Preparation of 1-methyl-N-(2-(o-tolyl)-1H-benzo[d]imidazol-6-yl)-1H-pyrazole-5-carboxamide (B)

Preparation of 6-nitro-2-(o-tolyl)-1H-benzo[d]imidazole (9)

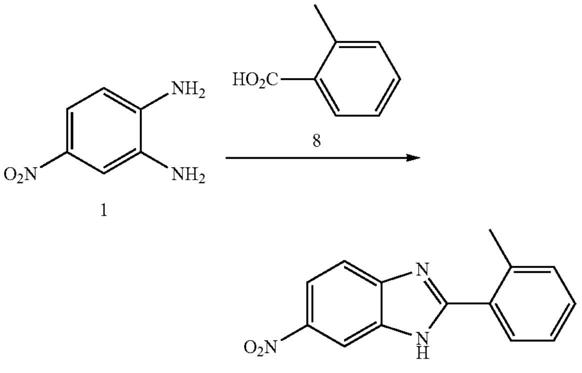
1
8
9

Compound (9) was synthesized according to the procedure reported for compound (3) starting from 4-nitrobenzene-1,2-diamine and 2-methylbenzoic acid (8). $^1$H-NMR ($CH_3OH$-$d_4$, 400 MHz): δH 8.58 (1H, s), 8.25 (1H, d, J=8.8 Hz), 7.76 (1H, s), 7.69 (1H, d, J=7.6 Hz), 7.38-7.51 (3H, m), 2.57 (3H, s).

Preparation of 2-(o-tolyl)-1H-benzo[d]imidazol-6-amine (10)

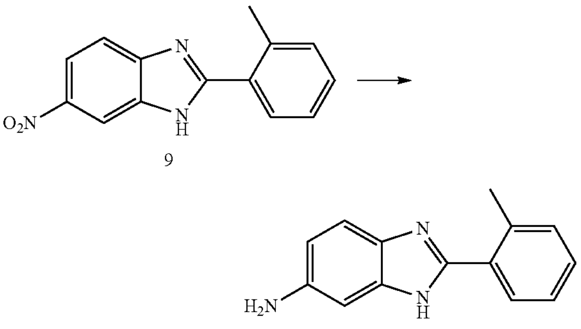
9
10

Compound (10) was synthesized according to the procedure reported for compound (4) starting from 6-nitro-2-(o-tolyl)-1H-benzo[d]imidazole (9). $^1$H-NMR ($CH_3OH$-$d_4$, 400 MHz): δH 7.57 (1H, d, J=7.6 Hz), 7.28-7.40 (4H, m), 6.95 (1H, s), 6.78 (1H, dd, J=2.0 Hz, J=8.4 Hz), 2.49 (3H, s).

Preparation of 1-methyl-N-(2-(o-tolyl)-1H-benzo[d]imidazol-6-yl)-1H-pyrazole-5-carboxamide (B)

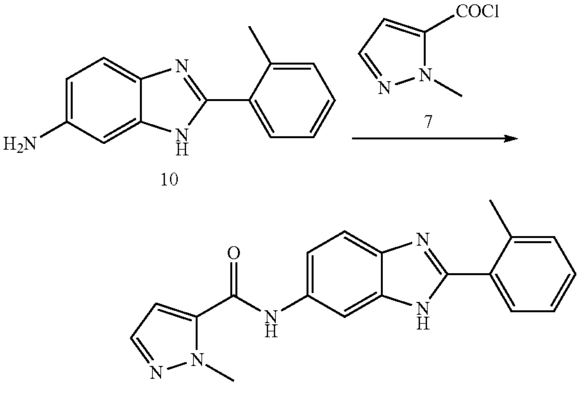
10
7
B

The title compound B was synthesized according to the procedure reported for compound A starting from 2-(o-tolyl)-1H-benzo[d]imidazol-6-amine (10) and 1-methyl-1H-pyrazole-5-carbonyl chloride (7). $^1$H-NMR (DMSO-$d_6$, 400 MHz): δH 12.58 (1H, m), 10.24 (1H, d, J=26 Hz), 8.12 (1H, d, J=25.2 Hz), 7.74 (1H, d, J=6.4 Hz), 7.64 (1H, d, J=8.4 Hz), 7.48-7.54 (2H, m), 7.36-7.42 (3H, m), 7.09 (1H, s), 4.11 (3H, s), 2.62 (3H, s); MS (m/z): 332.1 $[M+H]^+$; purity 97%.

Preparation of N-(2-(2-(difluoromethyl)phenyl)-1H-benzo[d]imidazol-6-yl)-1-methyl-1H-pyrazole-5-carboxamide (C)

Preparation of N-(2-amino-4-nitrophenyl)-2-(difluoromethyl) benzamide (12)

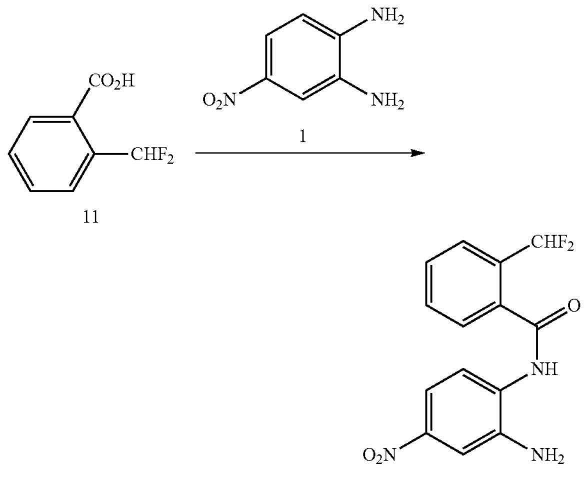

11 1 12

To a solution of 2-(difluoromethyl)benzoic acid (11, 3 g, 17.43 mmol) and 4-nitrobenzene-1,2-diamine (1, 3.20 g, 20.91 mmol) in DMF (20 mL) was added HATU (9.94 g, 26.14 mmol) and DIPEA (6.76 g, 52.29 mmol, 9.11 mL). The mixture was stirred at 25° C. for 3 hours. Water (50 mL) was added and precipitate was filtered and the filtered cake was concentrated to provide the free base of the title compound (12, 4.7 g, 15.30 mmol, 87.77% yield). $^1$H-NMR (DMSO-$d_6$, 400 MHz): δH 9.92 (1H, s), 8.27 (1H, d, J=2.0 Hz), 7.91-7.98 (2H, m), 7.76-7.78 (1H, m) 7.68-7.70 (2H, m), 7.35 (1H, t, J=55.2 Hz), 6.81 (1H, d, J=9.2 Hz), 6.60 (2H, s).

Preparation of 2-(2-(difluoromethyl)phenyl)-6-nitro-1H-benzo[d]imidazole (13)

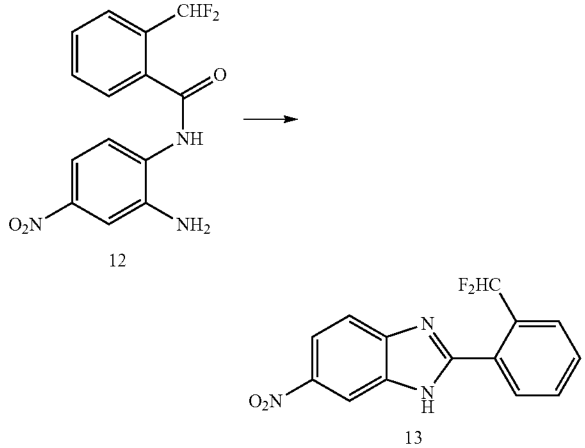

12 13

A mixture of N-(2-amino-4-nitrophenyl)-2-(difluoromethyl) benzamide (12, 1.5 g, 4.88 mmol) in $POCl_3$ (15 mL) was stirred at 80° C. for 3 h. The mixture was concentrated and washed three times by a solution of saturated aqueous $NaHCO_3$ (20 mL), extracted three times with EtOAc (20 mL), dried over anhydrous $Na_2SO_4$ and concentrated. The residue was purified by column chromatography ($SiO_2$, Petroleum ether/Ethyl acetate=30/1 to 2/1) to provide the free base of the title compound (13, 2.5 g, 9.02 mmol, 69.26% yield). $^1$H-NMR (DMSO-$d_6$, 400 MHz): δH 13.71 (1H, s), 8.60 (1H, s), 8.19 (1H, d, J=6.8 Hz), 7.97-8.11 (2H, m), 7.91 (1H, d, J=7.6 Hz), 7.74-7.83 (3H, m).

Preparation of 2-(2-(difluoromethyl)phenyl)-1H-benzo[d]imidazol-6-amine (14)

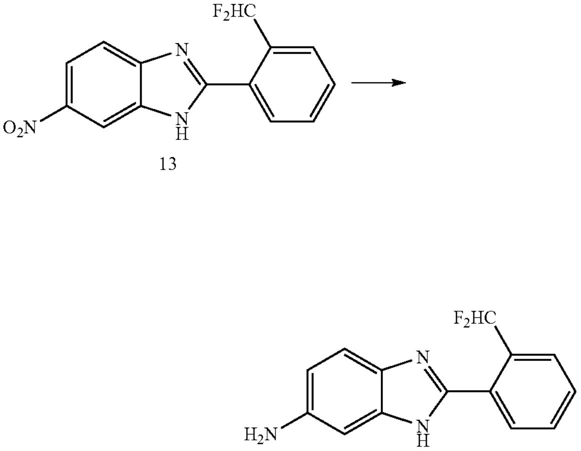

13 14

To a solution of 2-(2-(difluoromethyl)phenyl)-6-nitro-1H-benzo[d]imidazole (13, 370 mg, 1.28 mmol) in EtOH (12 mL) was added $H_2O$ (4 mL) and $NH_4Cl$ (684.28 mg, 12.79 mmol). Subsequently, Fe (357.19 mg, 6.40 mmol) was added at 50° C. The mixture was stirred at 50° C. for 1 h. The mixture was filtered and the filtrate was concentrated. The residue was purified by column chromatography ($SiO_2$, Petroleum ether/Ethyl acetate=10/1 to 1/1) to provide the free base of the title compound (14, 300 mg, 1.16 mmol, 90.46% yield).

Preparation of N-(2-(2-(difluoromethyl)phenyl)-1H-benzo[d]imidazol-6-yl)-1-methyl-1H-pyrazole-5-carboxamide (C)

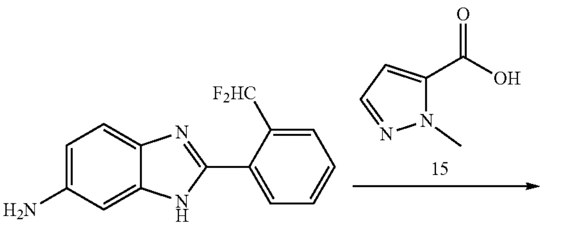

14 15

-continued

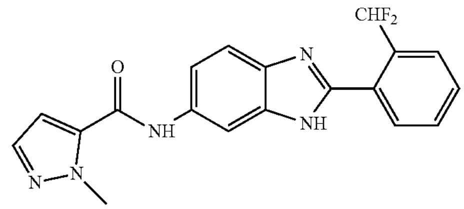

C

To a solution of 2-(2-(difluoromethyl)phenyl)-1H-benzo[d]imidazol-6-amine (14, 200 mg, 771.45 μmol) and 1-methyl-1H-pyrazole-5-carboxylic acid (15, 107.02 mg, 848.59 μmol) in DMF (5.0 mL) was added HATU (439.99 mg, 1.16 mmol) and DIPEA (299.11 mg, 2.31 mmol, 403.12 μL). The mixture was stirred at 25° C. for 12 h. The reaction mixture was quenched by addition of water (10 mL) at 25° C. and then extracted three times with EtOAc (10 mL). The combined organic layers were washed three times with brine (5 mL), dried over anhydrous $Na_2SO_4$, filtered and concentrated under reduced pressure to provide the crude product. The residue was purified by column chromatography ($SiO_2$, Petroleum ether/Ethyl acetate=10/1 to 1/1) to provide the free base of the title compound (C, 146 mg, 397.44 μmol, 50.49% yield). $^1$H-NMR (DMSO-$d_6$, 400 MHz): δH 12.99 (1H, s), 10.29 (1H, s), 8.11-8.25 (2H, m), 7.98 (1H, t, J=7.6 Hz), 7.87 (1H, d, J=8.0 Hz), 7.76 (1H, t, J=7.6 Hz), 7.63-7.70 (2H, m), 7.50-7.55 (2H, m), 7.09 (1H, d, J=2.0 Hz), 4.12 (3H, s); MS (m/z): 368.0 $[M+H]^+$; purity 98%.

Preparation of N-(2-(2-(difluoromethyl)phenyl)-1H-benzo[d]imidazol-6-yl)-1-methyl-1H-1,2,4-triazole-5-carboxamide (D)

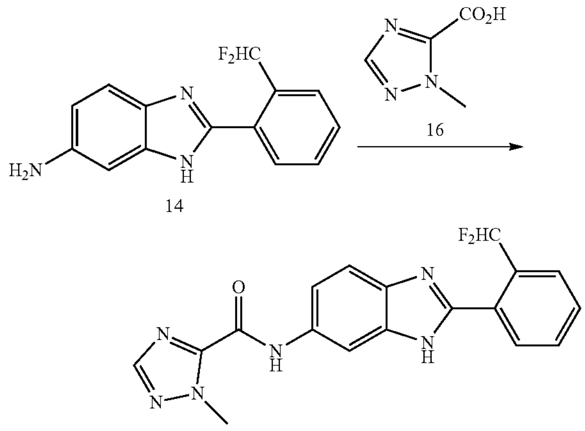

14

16

D

The title compound D was synthesized according to the procedure reported for compound C starting from 2-(2-(difluoromethyl)phenyl)-1H-benzo[d]imidazol-6-amine (14) and 1-methyl-1H-1,2,4-triazole-5-carboxylic acid (16). $^1$H-NMR (DMSO-$d_6$, 400 MHz): δH 13.02 (1H, s), 10.81 (1H, s), 8.24-8.10 (3H, m), 7.99 (1H, t, J=7.2 Hz), 7.87 (1H, d, J=7.6 Hz), 7.76 (1H, t, J=7.6 Hz), 7.64-7.70 (3H, m), 4.21 (3H, s); MS (m/z): 369.0 $[M+H]^+$; purity 96%.

Preparation of N-(2-(2-(difluoromethyl)-5-fluorophenyl)-1H-benzo[d]imidazol-6-yl)-1-methyl-1H-pyrazole-5-carboxamide (E)

Preparation of 2-bromo-1-(difluoromethyl)-4-fluorobenzene (18)

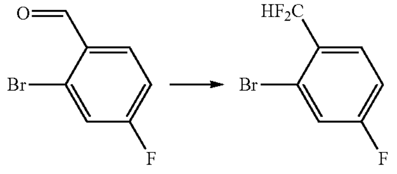

17 18

To a solution of 2-bromo-4-fluorobenzaldehyde (17, 20 g, 98.52 mmol) in DCM (200 mL) was added dropwise DAST (23.82 g, 147.78 mmol, 19.52 mL) and stirred at 0° C. for 30 min. Then the mixture was stirred at 40° C. for 9.5 hours. The reaction mixture was quenched with EtOH 50 mL at 0° C., and then washed twice with water (45 mL), dried over anhydrous $Na_2SO_4$, filtered and the filtrate was concentrated under reduced pressure to give the crude product that was purified by column chromatography ($SiO_2$, Petroleum ether/Ethyl acetate=1/0 to 20/1) to give the title compound (18, 19.3 g, 85.78 mmol, 43.53% yield). $^1$H-NMR (400 MHz, $CDCl_3$): δH 7.64-7.67 (1H, m), 7.34-7.37 (1H, m), 7.11-7.16 (1H, m), 6.67 (1H, t, J=54.8 Hz).

Preparation of methyl 2-(difluoromethyl)-5-fluorobenzoate (19)

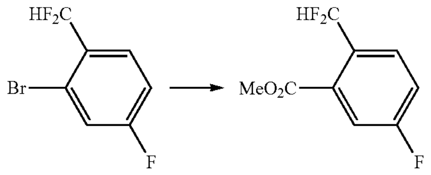

18 19

To a solution of 2-bromo-1-(difluoromethyl)-4-fluorobenzene (18, 9.8 g, 43.55 mmol, 1 eq) in DMF (100 mL) and MeOH (20 mL) was added TEA (14.39 g, 142.24 mmol, 19.80 mL), $Pd(OAc)_2$ (978.02 mg, 4.36 mmol) and 1,3-bis (diphenylphosphino) propane (DPPP, 1.80 g, 4.35 mmol). The mixture was stirred at 70° C. for 24 h under CO (15 psi). The reaction mixture was diluted with EtOAc (20 mL) and water (20 mL) and filtered. The filtrate was extracted three times with EtOAc (100 mL). The combined organic layers were washed three times with brine (30 mL), dried over anhydrous $Na_2SO_4$, filtered and the filtrate was concentrated under reduced pressure to give a residue. The crude product was purified by column chromatography ($SiO_2$, Petroleum ether/Ethyl acetate=1/0 to 1/1) to give the title compound (19, 8.4 g, 41.15 mmol, 47.24% yield). $^1$H-NMR (400 MHz, $CDCl_3$): δH 7.80-7.83 (1H, m), 7.70-7.73 (1H, m), 7.30-7.63 (2H, m), 3.94 (3H, s).

Preparation of 2-(difluoromethyl)-5-fluorobenzoic Acid (20)

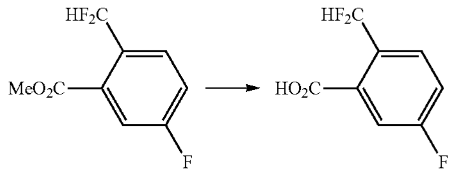

19 20

To a solution of methyl 2-(difluoromethyl)-5-fluorobenzoate (19, 8.4 g, 41.15 mmol) in MeOH (80 mL) was added NaOH (2 M in water, 30.00 mL, in $H_2O$). The mixture was stirred at 25° C. for 2 hours. The reaction mixture was adjusted to pH ~6-7 with 1M HCl and then concentrated under reduced pressure to remove MeOH. Then the mixture was extracted three times with $CHCl_3$:MeOH=10:1 (50 mL). The combined organic layers were dried over anhydrous $Na_2SO_4$, filtered and the filtrate was concentrated under reduced pressure to give the title completed (20, 7 g, 36.82 mmol, 89.48% yield). 1H-NMR (400 MHz, d-DMSO): δH 8.04 (1H, t, J=56.8), 7.58-7.62 (1H, m), 7.52-7.55 (1H, m), 7.20-7.25 (1H, m); MS (m/z): 189.0 [M−H].

Preparation of N-(2-amino-5-nitrophenyl)-2-(difluoromethyl)-5-fluorobenzamide (21)

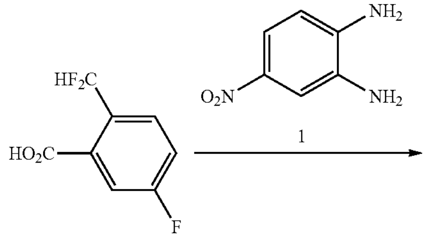

1

20

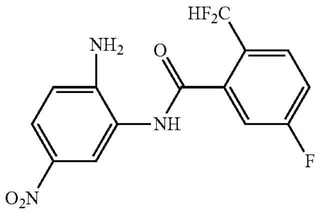

21

Compound 21 was synthesized according to the procedure reported for compound 12 starting from 2-(difluoromethyl)-5-fluorobenzoic acid (20). 1H-NMR (400 MHz, DMSO): δH 9.98 (1H, s), 8.23 (1H, d, J=2.8 Hz), 7.91-7.95 (2H, m), 7.79-7.83 (1H, m), 7.51-7.56 (1H, m), 7.31 (1H, t, J=55.2 Hz), 6.79 (1H, d, J=9.2 Hz), 6.63 (2H, s); MS (m/z): 326.0 [M+H]

Preparation of 2-(2-(difluoromethyl)-5-fluorophenyl)-6-nitro-1H-benzo[d]imidazole (22)

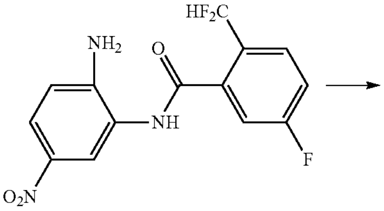

21

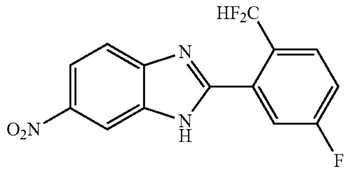

22

Compound 22 was synthesized according to the procedure reported for compound 13 starting from N-(2-amino-5-nitrophenyl)-2-(difluoromethyl)-5-fluorobenzamide (21). MS (m/z): 308.0 [M+H$^+$].

Preparation of 2-(2-(difluoromethyl)-5-fluorophenyl)-1H-benzo[d]imidazol-6-amine (23)

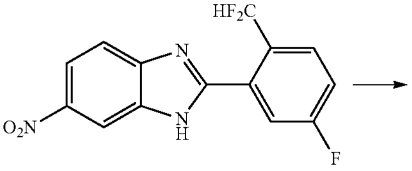

22

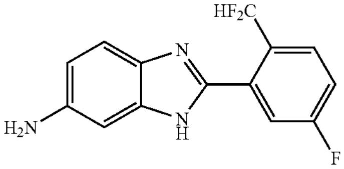

23

Compound 23 was synthesized according to the procedure reported for compound 14 starting from 2-(2-(difluoromethyl)-5-fluorophenyl)-6-nitro-1H-benzo[d]imidazole (22). 1H-NMR (400 MHz, d-DMSO): δH 12.44 (1H, s), 8.17 (1H, t, J=55.6 Hz), 7.85-7.89 (1H, m), 7.77 (1H, d, J=9.6 Hz), 7.36-7.44 (2H, m), 6.56-6.66 (2H, m), 5.11 (2H, s); MS (m/z): 278.0 [M+H$^+$].

Preparation of N-(2-(2-(difluoromethyl)-5-fluorophenyl)-1H-benzo[d]imidazol-6-yl)-1-methyl-1H-pyrazole-5-carboxamide (E)

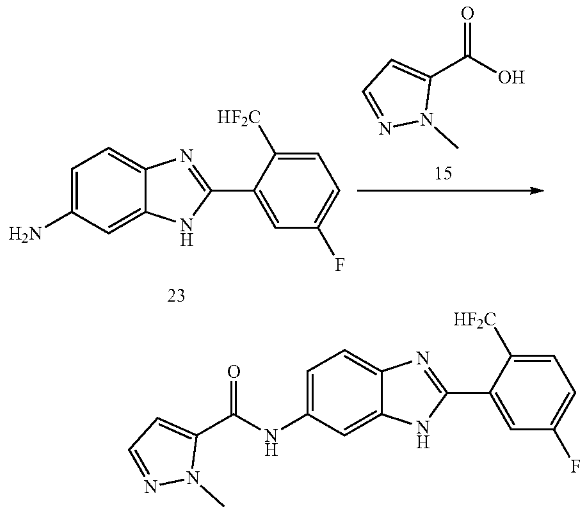

15

23

E

The title compound E was synthesized according to the procedure reported for compound C starting from 2-(2-(difluoromethyl)-5-fluorophenyl)-1H-benzo[d]imidazol-6-amine (23) and 1-methyl-1H-pyrazole-5-carboxylic acid (15). 1H-NMR (400 MHz, d-DMSO): δH 13.05 (1H, s), 10.29 (1H, s), 7.98-8.25 (2H, m), 7.91-7.94 (1H, m), 7.86-7.89 (1H, m), 7.64 (1H, d, J=8.8 Hz), 7.50-7.55 (3H, m), 7.08 (1H, d, J=1.6 Hz), 4.11 (3H, s); MS (m/z): 386.0 [M+H$^+$]; purity 95.6%.

Preparation of N-(2-(2-(difluoromethyl)-5-fluorophenyl)-1H-benzo[d]imidazol-6-yl)-1-methyl-1H-1,2,4-triazole-5-carboxamide (F)

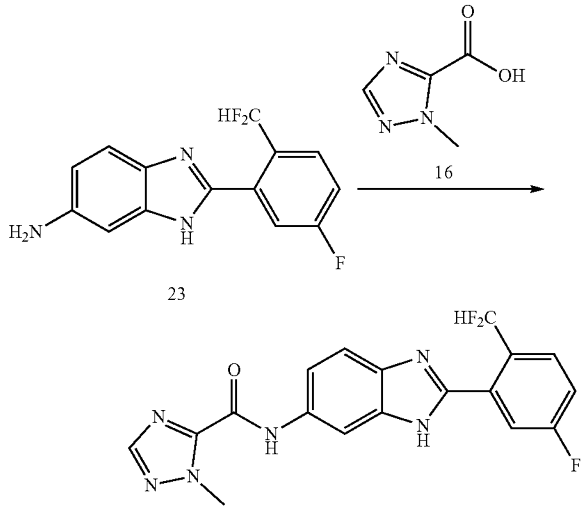

16

23

F

The title compound F was synthesized according to the procedure reported for compound C starting from 2-(2-(difluoromethyl)-5-fluorophenyl)-1H-benzo[d]imidazol-6-amine (23) and 1-methyl-1H-1,2,4-triazole-5-carboxylic acid (16). 1H-NMR ($CH_3OH$-$d_4$, 400 MHz): δH 13.22-12.28 (1H, m), 10.84 (1H, s), 8.25-8.09 (3H, m), 7.96-7.85 (2H, m), 7.70-7.66 (2H, m), 7.55-7.50 (1H, m), 4.21 (3H, s); MS (m/z): 387.1 [M+H$^+$]; purity 94.84%.

Preparation of 1-methyl-N-(2-(o-tolyl)-1H-benzo[d]imidazol-6-yl)-1H-1,2,4-triazole-5-carboxamide (G)

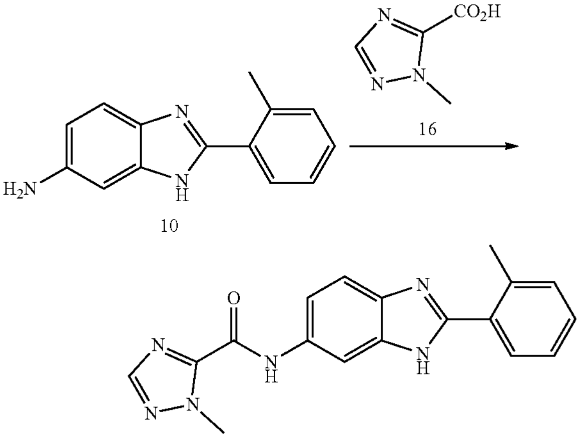

16

10

G

The title compound G was synthesized according to the procedure reported for compound C starting from 2-(o-tolyl)-1H-benzo[d]imidazol-6-amine (10) and 1-methyl-1H-1,2,4-triazole-5-carboxylic acid (16). $^1$H-NMR (DMSO-$d_6$, 400 MHz): δH 12.63 (1H, d, J=4.4 Hz), 10.77 (1H, d, J=30.4 Hz), 8.19 (2H, d, J=20.4 Hz), 7.75 (1H, d, J=6.4 Hz), 7.63-7.69 (1H, m), 7.54 (1H, dd, J=8.4 Hz, J=35.2 Hz), 7.39 (3H, s), 4.21 (3H, s), 2.62 (3H, s); MS (m/z): 333.1 [M+H]$^+$; purity 99%.

Preparation of 1-methyl-N-(2-(2-(trifluoromethyl)phenyl)-1H-benzo[d]imidazol-6-yl)-1H-1,2,4-triazole-5-carboxamide (H)

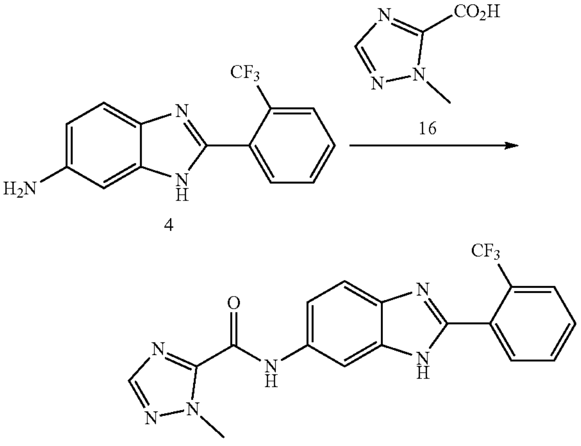

16

4

H

The title compound H was synthesized according to the procedure reported for compound C starting from 2-(2-(trifluoromethyl)phenyl)-1H-benzo[d]imidazol-6-amine (4) and 1-methyl-1H-1,2,4-triazole-5-carboxylic acid (16). $^1$H-NMR (DMSO-$d_6$, 400 MHz): δH 12.78 (1H, s), 10.80 (1H, d, J=26.4 Hz), 8.20 (2H, d, J=18.4 Hz), 7.95 (1H, d, J=7.6 Hz), 7.77-7.85 (3H, m), 7.61-7.65 (2H, s), 4.21 (3H, s); MS (m/z): 387.0 $[M+H]^+$; purity 98%.

Preparation of 1-methyl-N-(2-(2-(trifluoromethyl)phenyl)-4,5,6,7-tetrahydro-1H-benzo[d]imidazol-6-yl)-1H-1,2,4-triazole-5-carboxamide (I)

Step 1. Preparation of tert-butyl (3-bromo-4-oxocyclohexyl)carbamate (2)

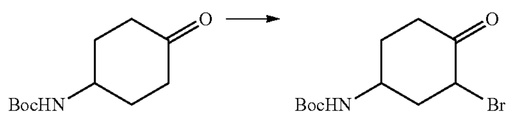

24

25

Aluminum trichloride (150.05 mg, 1.13 mmol, 61.50 mL) was added to a solution of tert-butyl (4-oxocyclohexyl) carbamate (24, 6 g, 28.13 mmol, 6.00 mL) in EtOAc (300 mL). Subsequently, 1 drop of $Br_2$ was added into the mixture at 0° C. After 5 min, $Br_2$ (4.50 g, 28.13 mmol, 1.45 mL) was added at 0° C. and the reaction mixture was stirred at 0° C. for 10 minutes. The mixture was poured into sat. $Na_2SO_4$ (200 mL). Then the mixture was extracted three times with EtOAc (100 mL). The combined organic layers were dried over anhydrous sodium sulfate, filtered and concentrated to get the title compound tert-butyl (3-bromo-4-oxocyclohexyl)carbamate (25, 8.22 g, crude).

Step 2. Preparation of 2-(trifluoromethyl) benzimidamide (27)

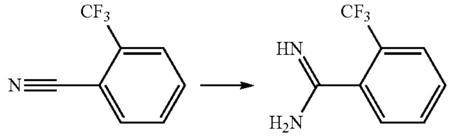

26

27

Potassium bis(trimethylsilyl)amide (1 M, 3.51 mL) was added to a solution of 2-(trifluoromethyl)benzonitrile (26, 200 mg, 1.17 mmol) in THF (1.0 mL). The mixture was stirred at 50° C. for 3 hours. Water (3.0 mL) was added to the mixture and then the mixture was concentrated. The crude product was purified by reversed-phase HPLC to get the title compound 2-(trifluoromethyl) benzimidamide (27, 180 mg, 74% yield).

Step 3. Preparation of tert-butyl (2-(2-(trifluoromethyl)phenyl)-4,5,6,7-tetrahydro-1H-benzo[d]imidazol-6-yl)carbamate (28)

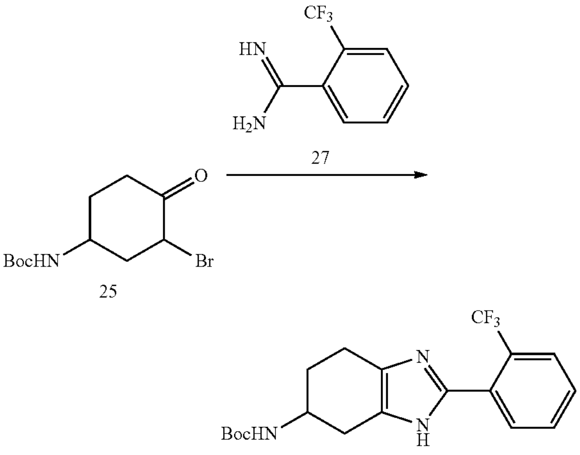

27

25

28

Potassium carbonate (283.82 mg, 2.05 mmol) was added to a solution of tert-butyl (3-bromo-4-oxocyclohexyl)carbamate (25, 200 mg, 684.54 mmol) and 2-(trifluoromethyl) benzimidamide (27, 128.80 mg, 684.54 mmol) in THF (10 mL). The mixture was stirred 12 hours at 85° C. Water (15 mL) was added to the mixture that was then extracted three times with EtOAc (3 mL). the combined organic layers were dried over anhydrous sodium sulfate, filtered and then concentrated under reduced pressure. The residue was purified by silica gel prep-TLC to get the title compound tert-butyl (2-(2-(trifluoromethyl)phenyl)-4,5,6,7-tetrahydro-1H-benzo[d]imidazol-6-yl)carbamate (28, 60 mg, 21% yield).

Step 4. Preparation of 2-(2-(trifluoromethyl)phenyl)-4,5,6,7-tetrahydro-1H-benzo[d]imidazol-6-amine Hydrochloride (29)

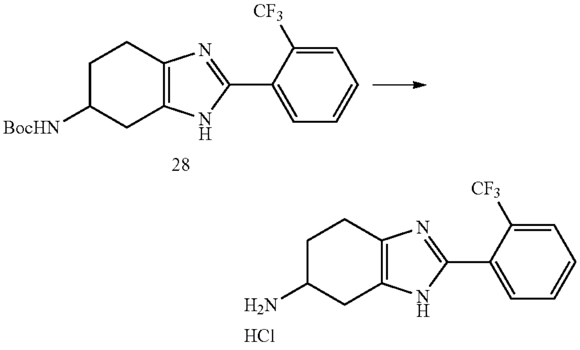

28

29

A solution of tert-butyl (2-(2-(trifluoromethyl)phenyl)-4,5,6,7-tetrahydro-1H-benzo[d]imidazol-6-yl)carbamate (28, 60 mg, 157.32 mmol) in HCl/EtOAc (2 M, 4.0 mL) was stirred for 3 hours at 15° C. The mixture was concentrated to get the title compound 2-(2-(trifluoromethyl)phenyl)-4,5,6,7-tetrahydro-1H-benzo[d]imidazol-6-amine hydrochloride (29, 50 mg, crude).

Step 5. Preparation of 1-methyl-N-(2-(2-(trifluoromethyl)phenyl)-4,5,6,7-tetrahydro-1H-benzo[d]imidazol-6-yl)-1H-1,2,4-triazole-5-carboxamide (I)

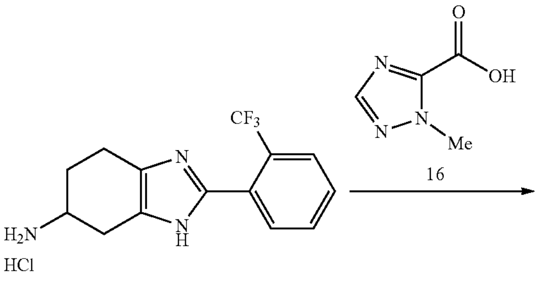
29
16

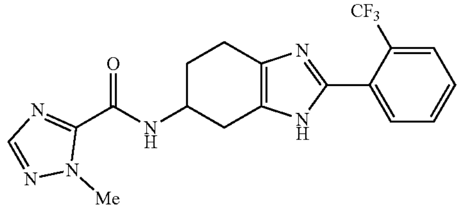
I

1-Methyl-1H-1,2,4-triazole-5-carboxylic acid (16, 24.00 mg, 188.84 mmol), HATU (89.75 mg, 236.04 mmol) and DIEA (101.69 mg, 786.81 mmol, 137.05 mL) were added to a solution of 2-(2-(trifluoromethyl)phenyl)-4,5,6,7-tetrahydro-1H-benzo[d]imidazol-6-amine hydrochloride (29, 50 mg, 157.36 mmol) in DMF (5.0 mL) at 15° C. and the mixture and stirred for 2 hours. Water (5.0 mL) was added to the mixture that was then extracted three times with EtOAc (5 mL). The organic layers were dried over anhydrous sodium sulfate, filtered and concentrated. The residue was first purified by silica gel prep-TLC and then by prep-HPLC to provide the title compound 1-methyl-N-(2-(2-(trifluoromethyl)phenyl)-4,5,6,7-tetrahydro-1H-benzo[d]imidazol-6-yl)-1H-1,2,4-triazole-5-carboxamide (I, 15 mg, 24% yield). $^1$H-NMR (400 MHz, DMSO-d6): $\delta_H$ 11.92 (1H, s), 8.86 (1H, m), 8.06 (1H, d, J=1.6 Hz), 7.82 (1H, d, J=8.0 Hz), 7.72 (1H, t, J=8.0 Hz), 7.56-7.66 (2H, m), 4.22 (1H, brs), 4.15 (3H, s), 2.55-2.90 (4H, m), 1.85-2.05 (2H, m); MS (m/z): $[M+H]^+$ 391.1; purity 98%.

Example 2: DRE-Luciferase Reporter Assay

AHR binds to Dioxin Responsive Elements (DRE) upstream of genes that it activates. One measure of AHR activity is activation of a reporter gene, such as luciferase, downstream of one or multiple DRE elements. Luciferase activity will reflect activation and inhibition of AHR in the cells expressing his reporter. 20000 Human HepG2 liver carcinoma—AhR-Lucia reporter cells or Human HT29 colon adenocarcinoma—AhR reporter cells or other cell line with a DRE-luciferase reporter stably transfected were plated in Eagle's Minimal Essential Medium, 10% heat-inactivated FBS, 1× non-essential amino acids Pen-Strep (10,000 U/mL) and Normocin (100 ug/mL) in plates (96-well, 384-well or other plates) and incubated overnight at 37° C. in a $CO_2$ incubator and treated with and without AhR antagonists at a log dilution starting at 100 uM.

After 1 hr that cells were plated an AHR activating ligand, such as TCDD, kynurenine, ITE (2-(1H-indole-3-ylcarbonyl)-4-thiazolecarboxylic methyl ester), VAF347, BNF (beta-naphthoflavone), FICZ (6-formylindolo(3,2-b) carbazole) or other AHR ligands at their specific $EC_{50}$ concentration, were added to the cells with or without AHR antagonist.

Cells were incubated for 24 or 48 hours or another time point and then, supernatant was analyzed for determination of luciferase activity as a read-out of the AHR activation or inhibition. Luciferase was measured with the commercial kit QUANTI-Luc™ assay solution kit from Invivogen following the manufacturer's instructions.

The level of luciferase with only agonist ligand added was the maximum signal while the luciferase with no antagonist was the minimum signal. $IC_{50}$ values were determined as the concentration which inhibits half of the luciferase activity. The $IC_{50}$ level of luciferase of compounds of the disclosure is reported in Table 2. "a" indicates an $IC_{50}$ value less than 100 nM, "b" indicates an $IC_{50}$ between 100 and 500 nM, "c" indicates an $IC_{50}$ above 500 nM, and "d" indicates that an $IC_{50}$ value could not be generated from the data.

TABLE 2

| Compound No. | HepG2-Luc $IC_{50}$ (nM) |
|---|---|
| A | B |
| B | B |
| C | B |
| D | A |
| E | A |
| F | A |
| G | B |
| H | A |

Example 3: CYP1A1 Gene Expression Assay

Human and mouse colorectal cancer (CRC) cell lines, HT29 and HT26 respectively, American Type Culture Collection (ATCC) are plated in a sterile tissue culture treated 96-well plate (ThermoFisher) at $8.0\times10^5$ cells per well, and grown overnight at 37° C., 5% $CO_2$ in DMEM complete (Gibco) in order to achieve confluence. After the incubation medium is aspirated off the cell monolayers, tissues are then washed with 200 µL of warmed PBS solution, and subsequently 190 µL of pre-warmed growth medium is added to each well. AhR antagonist of interest are diluted at a 20× concentration in growth medium containing 2% DMSO, and 10 µL of compound solutions are added to respective wells in triplicate. After 1 hr, AHR activating ligand, such as TCDD, kynurenine, ITE (2-(1H-indole-3-ylcarbonyl)-4-thiazolecarboxylic methyl ester), VAF347, BNF (beta-naphthoflavone), FICZ (6-formylindolo(3,2-b) carbazole or other AHR ligands, is added with or without AHR antagonist for 24 hours, after which media will be removed and stored at −80 C for later cytokine analysis. At the end of the incubation, medium is aspirated off the CRC cells, and the cells washed with 100 µL of cold PBS solution. RNA is extracted via the TaqMan™ Gene Expression Cells-to-CT™ Kit (ThermoFisher) according to the manufacturer's protocol. The QuantStudio 6 Flex (Applied Biosciences) is used to analyze mRNA levels of CYP1A1 using GAPDH as the endogenous control. TaqMan™ probe sets for both genes are acquired from ThermoFisher. Samples are run in triplicate and data is analyzed using the QuantStudio software and reported as linear and log 2(ΔΔCT) values. Statistical analysis is performed using a two-tailed t-test comparing CYP1A1 levels in the presence of each individual compound to the vehicle negative control. Compounds with $IC_{50}$ in the range of the nanomolar concentration are considered for further evaluation. This assay can be used to confirm the inhibitory effect of the compounds prior to testing using an in vivo model.

Example 4: Human PBMC (CD8+) Assay

Human donor blood (8 mL) is collected in sodium citrate CPT tubes and centrifuged at 1,600×g for 20 minutes at room temperature. Buffy coat containing PBMCs is collected and transferred to a 50 mL conical tube containing 30 mL of RPMI-1640 medium at room temperature (supplemented with penicillin-streptomycin). PBMCs samples are centrifuged at 400×g for 10 minutes at 10° C. The pelleted PBMCs are washed twice in 10 ml of RPMI-1640 medium (supplemented with penicillin-streptomycin), then resuspended in RPMI-1640 medium (supplemented with penicillin-streptomycin, fetal bovine serum, and L-Glutamine: RPMI-1640 complete medium). PBMCs are filtered through a 70-micron mesh to remove any cellular debris. The volume is adjusted to achieve 1.66×106 cells/mL, from which 180 μl (300,000 PBMCs) are added into each well in a 96-well plate (sterile, tissue culture treated, round bottom). PBMCs in a 96-well plate are rested for 30 minutes in a 37° C., 5% $CO_2$ incubator, then subsequently treated with 10 μl of indicated compound. For CD8+ (Killing T cells) differentiation assay, PMBC are cultured (1-10×$10^4$ cells) in RPMI-1640 complete medium for 2, 4 and 6 days and stimulated with 5 uL/ml ImmunoCult™ Human CD3/CD28/CD2 T Cell Activator; Stemcell #10990) with/without AhR antagonist Compounds. Cell viability was determined using a viability dye (eBioscience Fixable Viability Dye eFluor 780: ThermoFisher 65-0865-14) at 1:500 dilution. The cells were gated for CD8+, defined as Live, CD11c–, CD14–, CD19–, CD8+, CD4–, CD3+. Percent (%) CD8+ were calculated as percentage of CD8+ cells over total live T cells. Statistical analysis was performed with GraphPad Prism Software Using One-Way ANOVA.

Example 5: Human PBMC Cytokine Assay

Human donor blood (8 mL) is collected in sodium citrate CPT tubes and centrifuged at 1,600×g for 20 minutes at room temperature. Buffy coat containing PBMCs is collected and transferred to a 50 mL conical tube containing 30 mL of RPMI-1640 medium at room temperature (supplemented with penicillin-streptomycin). PBMCs samples are centrifuged at 400×g for 10 minutes at 10° C. The pelleted PBMCs are washed twice in 10 ml of RPMI-1640 medium (supplemented with penicillin-streptomycin), then resuspended in RPMI-1640 medium (supplemented with penicillin-streptomycin, fetal bovine serum, and L-Glutamine: RPMI-1640 complete medium). PBMCs are filtered through a 70 micron mesh to remove any cellular debris. The volume is adjusted to achieve 1.66×106 cells/mL, from which 180 μl (300,000 PBMCs) are added into each well in a 96-well plate (sterile, tissue culture treated, round bottom). PBMCs in a 96-well plate are rested for 30 minutes in a 37° C., 5% CO2 incubator, then subsequently treated with 10 μl of indicated compound. For cytokine secretion assay, PMBC are cultured (1-10×104 cells) in RPMI-1640 complete medium for 2, 4 and 6 days and stimulated with 5 uL/ml ImmunoCult™ Human CD3/CD28/CD2 T Cell Activator; Stemcell #10990) with/without AhR antagonist compounds. After 2, 4, and 6 days of incubation at 37° C., 5% $CO_2$, 100 μL of cell supernatant is collected and transferred to a 96-well plate (non-tissue treated, flat bottom). The plate is centrifuged at 350×g for 5 minutes at room temperature, and then the clear supernatant transferred to a new 96-well plate (non-tissue treated, flat bottom). The remaining cells are tested for viability using CellTiter-Glo® Luminescent Cell Viability Assay (Promega). The supernatant is analyzed for IL22 and IFg), using Luminex Immunoassay Technology (MAGPIX System). Cytokine levels of PBMC treated DMSO control samples are set to 100%, and compound treated samples are expressed relative to this.

Example 6: Solubility Determination Assay

The stock solutions of test compounds and control compound progesterone were prepared in DMSO at the concentrations of 10 mM. 15 μL of stock solution (10 mM) of each sample was placed in order into their proper 96-well rack. 485 μL of PBS pH 1.6 and pH 7.4 were added into each vial of the cap-less Solubility Sample plate. The assay was performed in singlet. One stir stick was added to each vial and then the vial was sealed using a molded PTFE/Silicone plug. The solubility sample plates were then transferred to the Eppendorf Thermomixer Comfort plate shaker and shaken at 25° C. at 1100 rpm for 2 hours. After completion of the 2 hours, plugs were removed and the stir sticks were removed using a big magnet. The samples from the Solubility Sample plate were transferred into the filter plate. Using the Vacuum Manifold, all the samples were filtered. An aliquot of 5 μL was taken from the filtrate followed by addition of 495 μL of a mixture of H2O and acetonitrile containing internal standard (1:1). A certain proportion of ultrapure water was used to dilute the diluent according to the peak shape. The dilution factor was changed according to the solubility values and the LC-MS signal response.

From the 10 mM DMSO STD plate, 6 μL was transferred into the remaining empty plate, and then 194 μL of DMSO were added to that plate to have a STD concentration of 300 μM. From the 300 μM DMSO STD plate, 5 μL were transferred into the remaining empty plate, and then 495 μL of a mixture of H2O and acetonitrile containing internal standard (1:1) were added to that plate to have a final STD concentration of 3 μM. A certain proportion of ultrapure water was used to dilute the diluent according to the peak shape. The concentrations of the standard samples were changed according to the LC-MS signal response.

The plate was placed into the well plate autosampler. The samples were evaluated by LC-MS/MS analysis.

All calculations were carried out using Microsoft Excel.

The filtrate was analyzed and quantified against a standard of known concentration using LC coupled with mass spectral peak identification and quantitation. Solubility values of the test compound and control compound were calculated as follows:

$$[\text{Sample}] = \frac{\text{Area ratio Sample} \times INJ\ \ VOL\ \ STD \times DF\ \ \text{Sample} \times [STD]}{\text{Area ratio } STD \times INJ\ \ VOL\ \ \text{Sample}}$$

Any value of the compounds that was not within the specified limits was rejected and the experiment was repeated.

The solubility of compounds of the disclosure in pH 1.6 and 7.4 buffers is reported in Table 3. "+++" indicates a solubility value equal to or greater than 10 μM, "++" indicates a solubility value between 1 and 10 μM, and "+" indicates a solubility value less than 1 μM.

TABLE 3

| Compound No. | Aq. Solubility at pH = 1.6 (μM) | Aq. Solubility at pH = 7.4 (μM) |
|---|---|---|
| A | +++ | +++ |
| C | +++ | ++ |
| D | +++ | ++ |
| E | +++ | ++ |
| F | +++ | ++ |
| H | +++ | ++ |

Example 7: Hepatocyte Stability Assay

Preparation of working solutions: 10 mM stock solutions of test compound and positive control were prepared in DMSO. In separate conical tubes, the 10 mM solution of test compound and the positive control were diluted to 100 μM by combining 198 μL of 50% acetonitrile/50% water and 2 μL of 10 mM stock.

Preparation of Hepatocytes: Incubation medium (William's E Medium supplemented with GlutaMAX) and hepatocyte thawing medium were placed in a 37° C. water bath and allowed warming for at least 15 minutes prior to use. A vial of cryopreserved hepatocytes was transferred from storage, ensuring that vials remained at cryogenic temperatures until thawing process ensued. Cells were thawed by placing the vial in a 37° C. water bath and gently shaking the vials for 2 minutes. After thawing was completed, vial was sprayed with 70% ethanol and transferred to a biosafety cabinet. Wide-bore pipette tip were used to transfer hepatocytes into 50 mL conical tube containing thawing medium. The 50 mL conical tube were placed into a centrifuge and spun at 100 g for 10 minutes. Upon completion of spin, thawing medium was aspirated and resuspended hepatocytes in enough incubation medium to yield ~$1.5\times10^6$ cells/mL. Using an AO/PI Staining, cells were counted and the viable cell density was determined. Cells with poor viability (<75% viability) were determined to be not acceptable for use. Cells were diluted with incubation medium to a working cell density of $0.5\times10^6$ viable cells/mL.

Procedure for Stability Determination: 198 μL of hepatocytes were pipetted into each wells of a 96-well non-coated plate. The plate was placed in the incubator to allow the hepatocytes to warm for 10 minutes. 2 μL of the 100 μM test compound or positive control solutions were pipetted into respective wells of the 96-well non-coated plate to start the reaction. The plate was returned to the incubator for the designed time points. Well contents was transferred in 25 μL aliquots at time points of 0, 15, 30, 60, 90 and 120 minutes. The aliquots were then mixed with 6 volumes (150 μL) of acetonitrile containing internal standard, IS (100 nM alprazolam, 200 nM caffeine and 100 nM tolbutamide) to terminate the reaction. The mixture was vortex for 5 minutes. Samples were centrifuged for 45 minutes at 3,220 g. An aliquot of 100 μL of the supernatant was diluted by 100 μL ultra-pure water, and the mixture was used for LC/MS/MS analysis. All incubations were performed in duplicate.

Data Analysis: All calculations were carried out using Microsoft Excel. Peak areas were determined from extracted ion chromatograms. In vitro half-life ($t_{1/2}$) of parent compound was determined by regression analysis of the percent parent disappearance vs. time curve.

The in vitro half-life (in vitro $t_{1/2}$) was determined from the slope value:

$$\text{in vitro } t_{1/2}=0.693/k$$

Conversion of the in vitro $t_{1/2}$ (in min) into the in vitro intrinsic clearance (in vitro $CL_{int}$, in μL/min/$1\times10^6$ cells) was done using the following equation (mean of duplicate determinations):

$$\text{in vitro } CL_{int}=\text{kV/N}$$

V=incubation volume (0.2 mL);

N=number of hepatocytes per well ($0.1\times10^6$ cells).

Data Processing Rules: The rules for data processing are shown in Table 4.

TABLE 4

| Remaining % | |
|---|---|
| ≥80% at 120 min | If T-test with $p < 0.05$ is obtained, report the calculated $CL_{int}$ value;<br>When the calculated $CL_{int}$ value <3.73, then report <3.73 instead of calculated value. If T-test with $p < 0.05$ is not obtained, then report <3.73 for $CL_{int}$ value and >371.12 for $t_{1/2}$ value when all the other data points fall in the range of 80%~120% (one data point within the range of 70%~130% is accepted, otherwise the experiment should be repeated). |
| <80% at 120 min | Always remove from the calculation all points with <10% left of 0.5 min sample, but leave at least 2 points<br>If T-test with $p < 0.05$ is obtained, report the calculated $CL_{int}$ value.<br>If T-test with $p < 0.05$ is not obtained, the experiment must be repeated. |

The human and rat liver hepatocyte clearance of compounds of the disclosure is reported in Table 5. "+++" indicates a $CL_{int}$ value less than 20 mL/min/Kg, "++" indicates a $CL_{int}$ between 20 and 50 mL/min/Kg, and "+" indicates an $CL_{int}$ above 50 mL/min/Kg.

TABLE 5

| Compound No. | Human hepatocyte clearance (mL/min/Kg) | Rat hepatocyte clearance (mL/min/Kg) |
|---|---|---|
| A | +++ | -- |
| H | +++ | +++ |

Example 8: Liver Microsome Stability Assay

The master solution was prepared according to Table 6.

TABLE 6

| Reagent | Stock Concentration | Volume | Final Concentration |
|---|---|---|---|
| Phosphate buffer | 100 mM | 210 μL | 100 mM |
| Microsomes | 20 mg/mL | 6.25 μL | 0.5 mg/mL |

Two separate experiments were performed as follows.

With Cofactors (NADPH): 25 μL of 10 mM NADPH was added to the incubations. The final concentrations of microsomes and NADPH were 0.5 mg/mL and 1 mM, respectively. The final concentration of microsomes was 0.5 mg/mL. The mixture was pre-warmed at 37° C. for 10 minutes. The reaction was started with the addition of 2.5 µL of 100 µM control compound or test compound solutions. Verapamil was used as positive control in this study. The final concentration of test compound or control compound was 1 µM. The incubation solution was incubated in water batch at 37° C. Aliquots of 25 µL were taken from the reaction solution at 0.5, 5, 15, 30 and 60 minutes. The reaction was stopped by the addition of 5 volumes of cold acetonitrile with IS (200 nM caffeine and 100 nM tolbutamide). Samples were centrifuged at 3, 220 g for 40 minutes. Aliquot of 100 µL of the supernatant was mixed with 100 µL of ultra-pure H2O and then used for LC-MS/MS analysis.

Data Analysis: All calculations were carried out using Microsoft Excel. Peak areas were determined from extracted ion chromatograms. The slope value, k, was determined by linear regression of the natural logarithm of the remaining percentage of the parent drug vs. incubation time curve.

The in vitro half-life (in vitro $t_{1/2}$) was determined from the slope value:

$$\text{in vitro } t_{1/2} = -(0.93/k)$$

Conversion of the in vitro $t_{1/2}$ (min) into the in vitro intrinsic clearance (in vitro $CL_{int}$, in µL/min/mg protein) was done using the following equation (mean of duplicate determinations):

$$\text{in vitro } CL_{int} = \left(\frac{0.693}{(t_{1/2})}\right) * \left(\frac{\text{volume of incubation } (\mu L)}{\text{amount of proteins (mg)}}\right)$$

The calculations of Scaled-up $CL_{int}$ (mL/min/kg), Predicted CLH (mL/min/kg) and EH were done using the following equation:

$$\text{Scaled-up } CL_{int} = (0.693/t_{1/2}) \times (1/(\text{microsomal protein concentration}(0.5\text{ mg/mL}))) \times \text{Scaling Factors;}$$

$$\text{Predicted } CLH = (QH \times \text{Scaled-up } CL_{int} \times f_{ub})/(QH + \text{Scaled-up } CL_{int} \times f_{ub});$$

$$EH = \text{Predicted } CLH/QH$$

where QH is the hepatic blood flow (mL/min/kg) (Table 7), $f_{ub}$ is the fraction of unbound drug in plasma which is assumed to be 1.

The scaling factors for intrinsic clearance prediction in the human and mouse microsomes are reported in Table 7.

TABLE 7

| Species | Microsomal protein per gram of liver | Liver weight per Kg of body weight | Scaling factor* | Hepatic blood flow |
|---|---|---|---|---|
| Human | 48.8 | 25.7 (human)<br>40.0 (rat) | 1254.2 human)<br>1792 (rat) | 20.7 (human)<br>55.2 (rat) |

*Scaling Factor = (microsomal protein per gram of liver) × (liver weight per kilogram of body weight)

Data Processing Rules: The rules for data processing are shown in Table 8.

TABLE 8

| Remaining % | Processing Rules |
|---|---|
| ≥80% at 60 min | If T-test with $p < 0.05$ is obtained, report the calculated $CL_{int}$ value<br>If T-test with $p < 0.05$ is obtained, report the calculated $CL_{int}$ value; When the calculated $CL_{int}$ value <7.50, then report <7.50 instead of calculated value.<br>If T-test with $p < 0.05$ is not obtained, then report <7.50 for $CL_{int}$ value and >184.78 for $t_{1/2}$ value when all the other data points fall in the range of 80%~120% (one data point within the range of 70%~130% is accepted, otherwise the experiment should be repeated). |
| <80% at 60 min | Always remove from the calculation all points with <10% left of 0.5 min sample, but leave at least 2 points<br>If T-test with $p < 0.05$ is obtained, report the calculated $CL_{int}$ value.<br>If T-test with $p < 0.05$ is not obtained, the experiment must be repeated. |

The human and rat liver microsome clearance of compounds of the disclosure is reported in Table 9. "+++" indicates a $Cl_{int}$ value less than 10 mL/min/Kg, "C++" indicates a $Cl_{int}$ between 10 and 20 mL/min/Kg, and "+" indicates a $Cl_{int}$ above 20 mL/min/Kg.

TABLE 9

| Compound No. | Human liver microsome clearance (mL/min/Kg) |
|---|---|
| A | +++ |
| C | +++ |
| H | +++ |

Example 9: Caco-2 Permeability Assay

Preparation of Caco-2 Cells: 50 µL and 25 mL of cell culture medium were added to each well of the Transwell insert and reservoir, respectively. The HTS transwell plates were incubated at 37° C., 5% $CO_2$ for 1 hour before cell seeding. Caco-2 cells were diluted to $6.86 \times 10^5$ cells/mL with culture medium and 50 µL of cell suspension were dispensed into the filter well of the 96-well HTS Transwell plate. Cells were cultivated for 14-18 days in a cell culture incubator at 37° C., 5% $CO_2$, 95% relative humidity. Cell culture medium was replaced every other day, beginning no later than 24 hours after initial plating.

Assessment of Cell Monolayer Integrity: Medium was removed from the reservoir and each Transwell insert and replaced with prewarmed fresh culture medium. Transepithelial electrical resistance (TEER) across the monolayer was measured using Millicell Epithelial Volt-Ohm measuring system (Millipore, USA). The Plate was returned to the incubator once the measurement was done. The TEER value was calculated according to the following equation:

$$\text{TEER measurement (ohms)} \times \text{Area of membrane } (cm^2) = \text{TEER value } (ohm \cdot cm^2)$$

TEER value should be greater than 230 $ohm \cdot cm^2$, which indicates the well-qualified Caco-2 monolayer.

Preparation of Solutions: 2 mM stock solutions in DMSO of control compounds were prepared and diluted with HBSS (10 mM HEPES, pH 7.4) to get 10 µM working solution. 0.2 mM stock solutions of test compounds in DMSO were prepared and diluted with HBSS (10 mM HEPES, pH 7.4 with 0.5% BSA) to get 1 μM working solution. Metoprolol, erythromycin and cimetidine were used as control compounds.

Performing the Drug Transport Assay: The Caco-2 plate was removed from the incubator. The monolayer was washed twice with pre-warmed HBSS (10 mM HEPES, pH 7.4). The plate was incubated at 37° C. for 30 minutes. To determine the rate of drug transport in the apical to basolateral direction, 125 μL of the working solution was added to the Transwell insert (apical compartment). A 50 μL sample was transferred immediately from the apical compartment to 200 μL of acetonitrile containing IS (100 nM alprazolam, 200 nM Caffeine and 100 nM tolbutamide) in a new 96-well plate as the initial donor sample (A-B) and it was vortexed at 1000 rpm for 10 minutes. The wells in the receiver plate (basolateral compartment) were filled with 235 μL of transport buffer. To determine the rate of drug transport in the basolateral to apical direction, 285 μL of the working solution were added to the receiver plate wells (basolateral compartment). A 50 μL sample was transferred immediately from the basolateral compartment to 200 μL of acetonitrile containing IS (100 nM alprazolam, 200 nM Caffeine and 100 nM tolbutamide) in a new 96-well plate as the initial donor sample (B-A) and it was vortexed at 1000 rpm for 10 minutes. The Transwell insert (apical compartment) was filled with 75 μL of transport buffer. The apical to basolateral direction and the basolateral to apical direction need to be done at the same time. The plates were incubated at 37° C. for 2 hours. At the end of the incubation, 50 μL samples from donor sides (apical compartment for Ap→Bl flux, and basolateral compartment for Bl→Ap) and receiver sides (basolateral compartment for Ap→Bl flux, and apical compartment for Bl→Ap) were transferred to wells of a new 96-well plate, followed by the addition of 4 volume of acetonitrile containing IS (100 nM alprazolam, 200 nM Caffeine and 100 nM tolbutamide). Samples were vortexed for 10 minutes, 50 μL samples were transferred to wells of a new 96-well plate, followed by the addition of 50 μL Hepes and 200 μL IS. All samples were vortexed for 10 minutes, and then centrifuged at 3,220 g for 40 minutes. An aliquot of 150 μL of the supernatant was mixed with an appropriate volume of ultra-pure water before LC-MS/MS analysis.

Data analysis: All calculations were carried out using Microsoft Excel. Peak areas were determined from extracted ion chromatograms. Lucifer yellow leakage of monolayer can be calculated using the following equation:

$$LY\ \text{Leakage} = \left(\frac{I_{acceptor} \times 0.3}{I_{acceptor} \times 0.3 + I_{donor} \times 0.1}\right) \times 100\%$$

where $I_{acceptor}$ is the fluorescence intensity in the acceptor well (0.3 mL), and $I_{donor}$ is the fluorescence intensity in the donor well (0.1 mL) and expressed as % leakage.

Lucifer yellow percentage amount transported values should be less than 1.5%. However, if the lucifer yellow percentage amount transported value for a particular transwell is higher than 1.5 but the determined digoxin $P_{app}$ in that transwell is qualitatively similar to that determined in the replicate transwells then, based upon the scientific judgement of the responsible scientist, the monolayer is considered acceptable.

Apparent permeability (Papp) can be calculated for drug transport assays using the following equation:

where $P_{app}$ is $$P_{app} = \frac{dQ/dt}{A \times D_o}$$

apparent permeability (cm/s×$10^{-6}$);

dQ/dt is the rate of drug transport (pmol/second);

A is the surface area of the membrane (cm2);

$D_o$ is the initial donor concentration (nM; pmol/$cm_3$).

Efflux ratio can be determined using the following equation:

$$\text{Effinx Ratio} = \frac{P_{app(B-A)}}{P_{app(A-B)}}$$

where $P_{app(B-A)}$ indicates the apparent permeability coefficient in basolateral to apical direction, and $P_{app(A-B)}$ indicates the apparent permeability coefficient in apical to basolateral direction.

The apparent permeability ratio of compounds of the disclosure is reported in Table 10. "A" indicates a $P_{app}$ value greater than 10*$10^{-6}$ cm/s, "B" indicates an $P_{app}$ between 2 and 10*$10^{-6}$ cm/s, and "C" indicates an $P_{app}$ below 2*$10^{-6}$ cm/s.

TABLE 10

| Compound No. | Caco2 $P_{app}$ (AB)/(BA) ($10^{-6}$ cm/s) |
|---|---|
| A | A/A |
| H | A/A |

Example 10: Plasma Protein Binding Determination with Ultracentrifugation Method The frozen plasma (stored at −80° C.) was thawed in a 37° C. water bath, followed by centrifugation at 3,220 g for 10 minutes to remove clots. The supernatant was removed into a new tube as the spun plasma. The spun plasma was pre-warmed in a 37° C. water bath for 10 minutes. The stock solutions of test compounds were diluted to 200 μM in DMSO, and then spiked into the plasma. Duplicate samples were prepared. The final concentration of compound was 1.0 μM. The final concentration of organic solvent was 0.5%. Warfarin was used as positive control in the assay. 1.0 mL of the spiked plasma was transferred to a new balance ultracentrifuge tube. Samples were incubated at 37° C., 5% $CO_2$ for 30 minutes. After incubation, the balance ultracentrifuge tubes were centrifuged at 600,000 g for 5.5 hours at 37° C. After centrifugation, 50 μL solution was removed from the center of the ultracentrifuge tubes as the post-ultracentrifugation samples, followed by the addition of 50 μL blank plasma and 400 μL quench solution (acetonitrile containing internal standards (IS, 100 nM Alprazolam, 500 nM Labetalol and 2 μM Ketoprofen)) to precipitate protein and release compounds. Samples were vortexed for 2 minutes, followed by centrifugation at 20,000 g for 15 minutes at room temperature. The supernatant was diluted with ultrapure water and then used for LC-MS/MS analysis. Stability samples was prepared by transferring 50 μL of the spiked plasma to 0.6 mL tubes and incubated at 37° C., 5% CO2 for 0.5 and 6 hours. After incubation, 50 μL PBS (100 mM, pH7.4) and 400 μL quench solution were added to the stability samples. And then stability samples were treated the same way as the post-ultracentrifugation samples. The supernatant was diluted with ultrapure water and then used for LC-MS/MS analysis. 0.5 hour time point samples were also used as no-spun controls. Time 0 samples were prepared by transferring 50 μL spiked plasma to 0.6 mL tubes containing 50 μL PBS, followed by the addition of 400 μL quench solution to precipitate protein and release compound. And then these samples were treated the same way as the post-ultracentrifugation samples. The supernatant was diluted with ultrapure water and then used for LC-MS/MS analysis.

Data Analysis: All calculations were carried out using Microsoft Excel. The concentrations of test compound in plasma samples and post-ultracentrifugation plasma was determined from peak areas. The percentages of test compound bound was calculated as follows:

$$\% \text{ Unbound} = (\text{Peak Area post-}\mathit{ultracentrifugation}/\text{Peak Area non-spun control}) \times 100\%$$

$$\% \text{ Bound} = 100\% - \% \text{ Unbound}$$

$$\text{Remaining\% at } 0.5\ hr = \text{Area ratio } 0.5\ hr/\text{Area ratio } 0\ hr \times 100\%$$

$$\text{Remaining\% at } 6\ hr = \text{Area ratio } 6\ hr/\text{Area ratio } 0\ hr \times 100\%$$

$$\text{Log}K = \text{Log}\left(\frac{\% \text{ Bound}}{100 - \% \text{ Bound}}\right)$$

The level of binding to human plasma protein of compounds of the disclosure is reported in Table 11. "+++" indicates a % bound value less than 50, "++" indicates a % bound value between 50 and 75, and "+" indicates a % bound value above 75.

TABLE 11

| Compound No. | Human plasma protein binding (% bound) |
|---|---|
| H | + |

Example 11: CYP Inhibition Assay

Stock solutions of test compounds were prepared in DMSO at the concentrations of 10 mM. Stock solution was diluted to 2 mM with acetonitrile. The final concentration of test compounds was 10 μM. The concentration of positive inhibitor is listed in Table 12. For the stock solution preparation, if the positive control could not be well dissolved in the mixture of DMSO and acetonitrile (1:4) at the highest concentration, another mixture of acetonitrile and DMSO, the mixture of acetonitrile and H2O or DMSO will be used to dissolve the compound.

TABLE 12

Table 4. Positive inhibitor nominal concentration

| CYP Isoform | Positive control | Conc. of stock solution (μM) | Final conc. in system (μM) |
|---|---|---|---|
| CYP2D6, 3A4 | Quinidine, Ketoconazole | 100 μM | 0.5 μM |

Preparation details of these substrates are given in Table 13. The substrate solutions are stored in a −20° C. freezer and warmed to room temperature prior to use.

TABLE 13

Table 5. Preparation of Substrate Stock Solution

| CYP Isoform | Substrate | Conc. of stock solution (mM) | Final conc. in system (μM) | Incubation Time |
|---|---|---|---|---|
| 2D6 | Dextromethorphan | 0.4 (in ACN) | 2 | 20 min |
| 3A4 | Midazolam | 0.2 (in MeOH + ACN) | 1 | 5 min |

Preparation of Phosphate Buffer (100 mmol/L, pH 7.4): To prepare the Solution A, 7.098 g of disodium hydrogen phosphate were weighed out and added into 500 mL of pure water, then sonicated to dissolve the content. To prepare the Solution B, 3.400 g of potassium dihydrogen phosphate were weighed out and added into 250 mL of pure water, then sonicated to dissolve the content. Solution A was placed on a stirrer and slowly Solution B was added into Solution A until the pH reached 7.4. Preparation of 10 mmol/L NADPH Solution: NADPH was dissolved at 8.334 mg/mL in phosphate buffer; the solution was freshly prepared prior to use.

The master solution was prepared according to Table 14. The incubation was carried out in 96 deep well plates. The following volumes were dispensed into each well of the incubation plate: 179 μL of the substrate and HLM mixture in phosphate buffer, 1 μL of the compound working solution, or vehicle (mixture of DMSO and acetonitrile (1:4)). The incubation plate was placed into the water bath and pre-warmed at 37° C. for 15 minutes before the reactions was started by the addition of 20 μL of 10 mmol/L NADPH solution in phosphate buffer. After the addition of NADPH, the incubation plate was incubated at 37° C. for corresponding time. The assay was performed in duplicate.

TABLE 14

Table 6. Preparation of master solution

| Buffer | Stock Concentration | Volume | Final Concentration |
|---|---|---|---|
| Microsomes | 20 mg/mL | 2 μL | 0.2 mg/mL |
| Phosphate buffer | 100 mM | 176 μL | 100 mM |
| Substrate | — | 1 μL | — |

The reaction was quenched by the addition of 1.5 volume (300 μL) of cold acetonitrile containing 3% formic acid and internal standards (200 nM Labetalol, 200 nM Alprazolam and 200 nM tolbutamide). The plate was centrifuged at 3,220 g for 40 minutes. 100 μL of the supernatant was transferred to a new plate. The supernatant was diluted with 100 μL pure water. The samples were mixed well and analyzed using UPLC/MS/MS.

Data Analysis: The automatic peak integration areas are checked for all the samples. The Analyte Peak Area and Internal Standard Peak Area are exported into excel spreadsheet. The inhibition of each P450 enzyme in human liver microsomes is measured as the percentage decrease in the activity of marker metabolite formation compared to non-inhibited controls (=100% activity).

The percentage of remaining activity was calculated as follows:

Area Ratio=Peak Area Analyte/Peak Area Internal Standard

Remaining Activity (%)=Area Ratio test compound/Area Ratio vehicle*100%

Inhibition %=100−Remaining Activity (%)

Example 12: hERG Inhibition Assay hERG stably expressed HEK 293 cell line (Cat #K1236) was purchased from Invitrogen. The cells are cultured in 85% DMEM, 10% dialyzed FBS, 0.1 mM NEAA, 25 mM HEPES, 100 U/mL Penicillin-Streptomycin and 5 μg/mL Blasticidin and 400 μg/mL Geneticin. Cells are split using TrypLE™ Express about three times a week and maintained between ~40% to ~80% confluence. Before the assay, the cells were onto the coverslips at 5×105 cells/per 6 cm cell culture dish and induced with doxycycline at 1 μg/mL for 48 hours.

External solution (in mM): 132 NaCl, 4 KCl, 3 CaCl2, 0.5 MgCl2, 11.1 glucose, and 10 HEPES (pH adjusted to 7.35 with NaOH). Internal solution (in mM): 140 KCl, 2 MgCl2, 10 EGTA, 10 HEPES and 5 MgATP (pH adjusted to 7.35 with KOH). Working solution preparation for test compound: test compounds were initially prepared in DMSO with final concentration of 10 mM as stock solution. Stock solution of each compound was serial-diluted by ratio of 1:3 with DMSO to prepare additional 3 intermediate solutions including 3.33, 1.11 and 0.37 mM.

Before performing the hERG assay, the working solutions were prepared by dilution of 10, 3.33, 1.11, and 0.37 mM intermediate solutions in 1000 folds using extracellular solution, while 30 μM working solution was prepared by 333.333-folds dilution of 10 mM DMSO stock. so that the final concentration of working solution was 30, 10, 3.33, 1.11 and 0.37 μM. The final DMSO concentration in working solutions was maintained in range of 0.1-0.3% (v/v).

Experimental procedure: the coverslip was removed from the cell culture dish and placed it on the microscope stage in bath chamber. A desirable cell was located using the ×10 objective. The tip of the electrode was located under the microscope using the ×10 objective by focusing above the plane of the cells. Once the tip was in focus, the electrode was advanced downwards towards the cell using the coarse controls of the manipulator, while simultaneously moving the objective to keep the tip in focus. When directly over the cell, the fine controls of the manipulator were used to approach the surface of the cell in small steps, by using the ×40 objective. Gentle suction was applied through the side-port of the electrode holder to form a gigaohm seal.

Cfast was used to remove the capacity current that is in coincidence with the voltage step. The whole cell configuration was obtained by applying repetitive, brief, strong suction until the membrane patch has ruptured. membrane potential was set to −60 mV at this point to ensure that hERG channels were not open. The spikes of capacity current was then cancelled using the Cslow on the amplifier.

Holding potential was set to −90 mV for 500 ms; current was recorder at 20 kHz and filtered at 10 kHz. Leaking current was tested at −80 mV for 500 ms.

The hERG current was elicited by depolarizing at +30 mV for 4.8 seconds and then the voltage was taken back to −50 mV for 5.2 seconds to remove the inactivation and observe the deactivating tail current. The maximum amount of tail current size was used to determine hERG current amplitude. Current was recorded for 120 seconds to assess current stability. Only stable cells with recording parameters above threshold were proceeded with further drug administrations. Vehicle control was applied to the cells to establish the baseline. Once the hERG current was found to be stabilized for 5 minutes, working solution was applied. hERG current in the presence of test compound were recorded for approximately 5 minutes to reach steady state and then 5 sweeps were captured. For dose response testing, 5 doses of test compound was applied to the cells cumulatively from low to high concentrations. In order to ensure the good performance of cultured cells and operations, the positive control, Dofetilide, with 5 doses was also used to test the same batch of cells.

The following criteria were used to determine data acceptability: initial seal resistance >1 GΩ; leak currents <50% of the control peak tail currents at any time; the peak tail amplitude >300 pA; membrane resistance Rm>500 MΩ; access resistance (Ra)<15 MΩ; apparent run-down of peak current <2.5% per min.

Data that met the above criteria for hERG current quality were further analyzed as the following steps. Percent current inhibition was calculated using the following equation: (Note: PatchMaster or Clampfit software were used to extract the peak current from the original data).

$$\text{Peak current inhibition} = \left(1 - \frac{\text{Peak tail current}_{compound}}{\text{Peak tail current}_{blank\ vehicle}}\right) \times 100$$

The dose response curve of test compounds was plotted with % inhibition against the concentration of test compounds using Graphpad Prism 6.0, and fit the data to a sigmoid dose-response curve with a variable slope.

Example 13: In Vivo Rat PK Studies

The studies were conducted in male SD rats, three rats per group. Compounds were dosed 1.0 mg/Kg i.v. (vehicle ethanol: % PEG400 in deionized water, in proportions suitable for dosing a clear solution) and 3.0 mg/Kg p.o. (vehicle: 1% methyl cellulose: 1,500 cP in DI water (w/v)).

In Vivo Model

Balb/c and C57BL/6 mice will be purchased from certified vendors and used in the studies. Animal husbandry, feeding and health conditions will be according to animal welfare guidelines. AHR agonist, and test compounds will be formulated in suitable vehicles.

CYP1A1 Levels in liver and spleen: C57BL/6 mice (n=3 per group) will be treated with AHR agonist alone or with AHR antagonist. Animals will be sacrificed at 4 or 10 hours after treatment upon which their livers and spleens will be collected and subsequent RT-PCR will be performed to determine levels of Cyplal and GAPDH. Data analysis will be performed including normalization to GAPDH housekeeping gene and to control treatment.

Efficacy Study AHR Antagonist and Checkpoint Inhibitor Anti-PD-1 in the Mouse Colorectal Cancer Model CT26 in Balb/c Mice CT26 is a murine colon carcinoma cell line obtained from ATCC. CT26 cells will be cultured in RPMI supplemented with 10% FBS.1 106 CT26 cells in 100 μL PBS will be implanted subcutaneously in 6-8-week-old Balb/c mice. Dosing for the efficacy study will start 5 days after implantation and after the tumor have reached 100 mm3: AHR antagonist will be dosed orally, every day (QD) at 30 mg/kg and 10 mg/kg for 3 weeks. anti-PD-1 (BioXcell RMPl-14) will be twice a week, intraperitoneally at 10 mg/kg for five total doses. Tumors will be monitored by caliper measurement every day and body weight will be measured three times per week. At the end point, tumors will be recovered and analyzed by Flowcytometry and or IHC for infiltrated tumor immune cells.

Efficacy Study AHR Antagonist and Checkpoint Inhibitor Anti-PD-1 in the Mouse Colorectal Cancer Model MC38 in C57BL/6

MC38 is a murine colon carcinoma cell line obtained from Kerafast. MC38 cells will be cultured in RPMI supplemented with 10% FBS. 1 106 MC38 cells in 100 μL PBS will be implanted subcutaneously in 6-8-week-old C57BL/6 mice. Dosing for the efficacy study will start 5 days after implantation and after the tumor have reached 100 mm3: AHR antagonist will be dosed orally, every day (QD) at 30 mg/kg and 10 mg/kg for 3 weeks. anti-PD-1 (BioXcell RMP1-14) will be twice a week, intraperitoneally at 10 mg/kg for five total doses. Tumors will be monitored by caliper measurement every day and body weight will be measured three times per week. At the end point, tumors will be recovered and analyzed by Flowcytometry and or IHC for infiltrated tumor immune cells.

AHR-Dependent Gene Expression in Tumor, Spleen and Liver:

AHR-dependent gene expression will be measured in tissue samples such as tumor or liver. RNA will be extracted from the tissue via RNA isolation kit such as Qiagen. The RNA extraction will be done from total cells or cells post-sorting for specific populations of cells such as tumor cells, tumor associated-T cells, tumor associated-myeloid cells, Tumor associate-macrophages or others. Gene expression will be determined by quantitative RT-PCR using probes for specific genes including a housekeeping gene such as Gapdh for normalization. AHR-dependent genes will be examined include but are not limited to: CYP1A1, CYP1B1, AHRR, IDO1, IDO2, IL22, IL6, VEGFA, STAT3, cdc2, MMP13, MMP-9.

The invention claimed is:

1. A compound of Formula I (I)

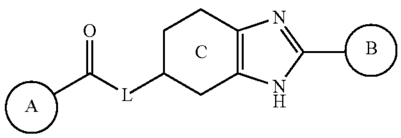

or a pharmaceutically acceptable salt thereof, wherein:

ring A is chosen from optionally substituted 4-10 membered heteroaryls;

ring B is chosen from substituted 6-10 membered aryls;

ring C is chosen from optionally substituted cyclohexenyls and optionally substituted phenyls; and L is chosen from divalent linking groups, provided that ring B is not

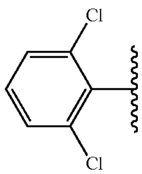

.

2. The compound of claim 1, or a pharmaceutically acceptable salt thereof, wherein the compound is chosen from compounds of formula (II):

(II)

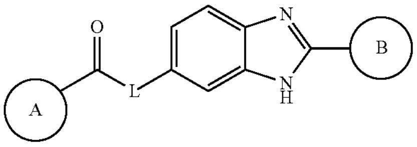

and pharmaceutically acceptable salts thereof.

3. The compound of claim 2, or a pharmaceutically acceptable salt thereof, wherein the compound is chosen from compounds of formula (III):

(III)

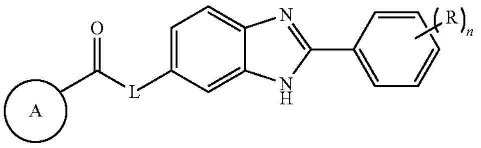

and pharmaceutically acceptable salts thereof, wherein:

n is 1, 2, 3, 4, or 5; and each R is independently chosen from optionally substituted $C_1$-$C_{10}$ alkyls, optionally substituted $C_1$-$C_{10}$ alkoxys, optionally substituted aminos, cyano, halos, hydroxy, and —C(O)H.

4. The compound of claim 3, or a pharmaceutically acceptable salt thereof, wherein the compound is chosen from compounds of formula (IV):

(IV)

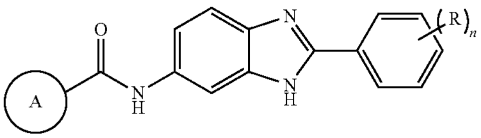

and pharmaceutically acceptable salts thereof.

5. The compound of claim 4, or a pharmaceutically acceptable salt thereof, wherein the compound is chosen from compounds of formula (V):

(V)

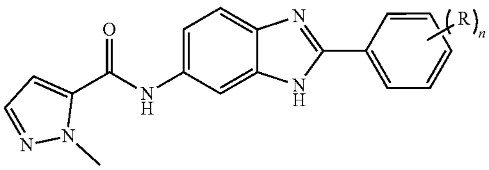

and pharmaceutically acceptable salts thereof, or compounds of formula (VI):

(VI)

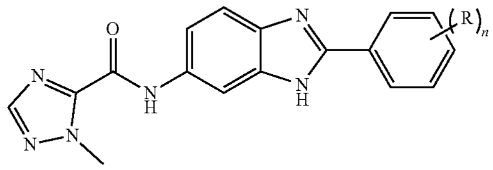

and pharmaceutically acceptable salts thereof.

6. The compound of claim 1, or a pharmaceutically acceptable salt thereof, wherein:

ring A is chosen from 4-10 membered heteroaryls, wherein each 4-10 membered heteroaryl is independently optionally substituted with 1 to 5 instances of $R^A$, and each $R^A$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and —NR"R", wherein each R" is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls.

7. The compound of claim 6, or a pharmaceutically acceptable salt thereof, wherein ring A is chosen from 5-8 membered heteroaryls optionally substituted with 1 to 4 instances of $R^A$.

8. The compound of claim 6, or a pharmaceutically acceptable salt thereof, wherein ring A is chosen from pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl, wherein each of pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl is independently optionally substituted with 1 to 3 instances of $R^A$.

9. The compound of claim 8, or a pharmaceutically acceptable salt thereof, wherein ring A is chosen from pyrazolyl optionally substituted with 1 to 3 instances of $R^A$ and triazolyl rings optionally substituted with 1 to 2 instances of $R^A$.

10. The compound of claim 1, or a pharmaceutically acceptable salt thereof, wherein ring A is

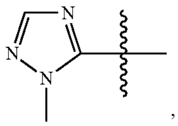 , 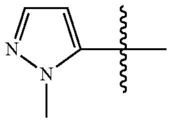 , 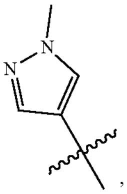 , 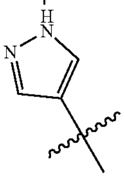 , 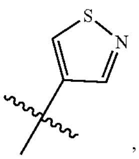 , 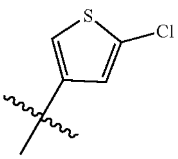 , -continued

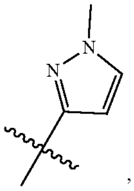 , 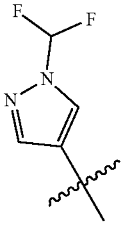 , 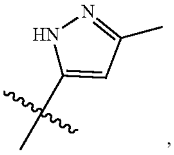 , 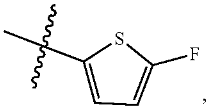 , 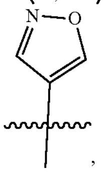 , 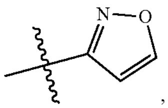 , 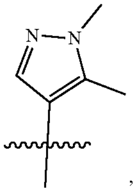 , 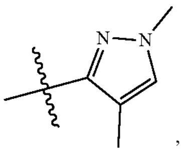 , 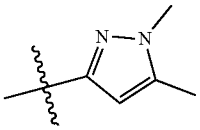 , 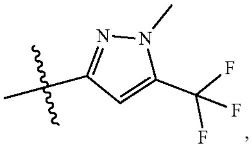 , 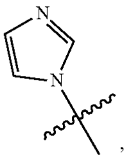 , 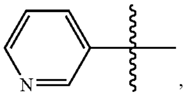 , 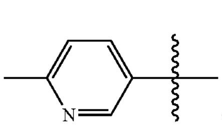 , 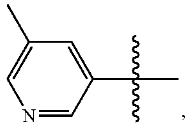 , 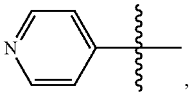 , 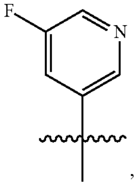 , 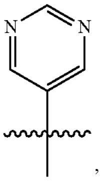 , or 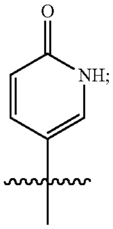

and Ring B is

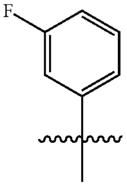 , 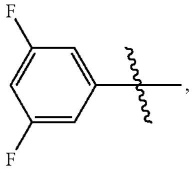 , 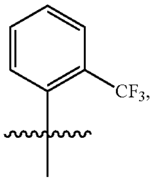

-continued

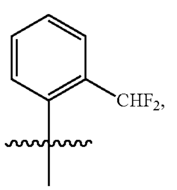, 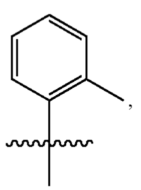,

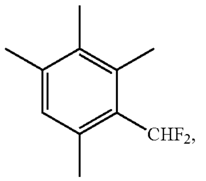, 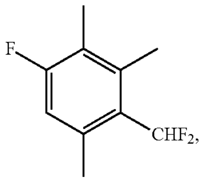,

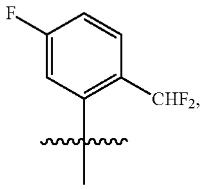, 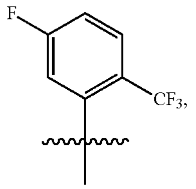,

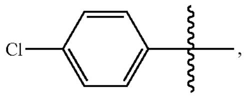, 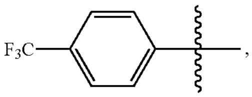,

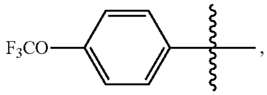, 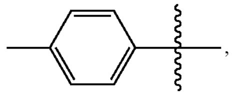,

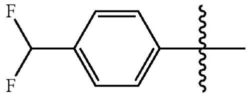, 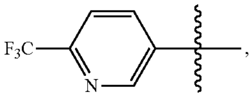,

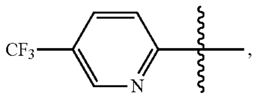, 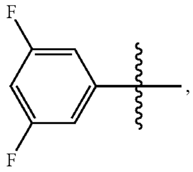,

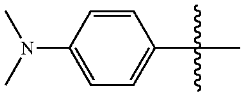, 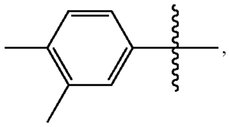,

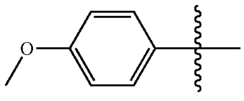,

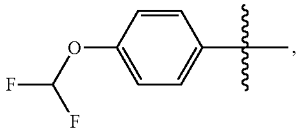,

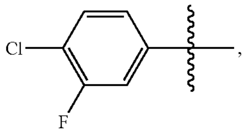, 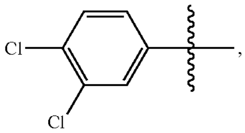,

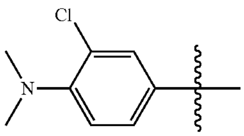, 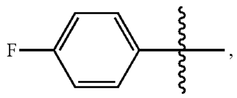,

-continued

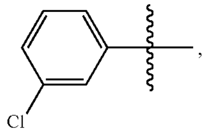, or 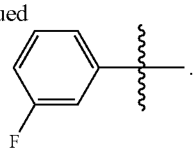.

11. The compound of claim 1, or a pharmaceutically acceptable salt thereof, wherein ring B is phenyl substituted with 1 to 3 instances of $R^B$; and each $R^B$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and —NR"R", wherein each R" is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls.

12. The compound of claim 1, or a pharmaceutically acceptable salt thereof, wherein L is chosen from —NH— and substituted divalent amines of formula —NR'—, wherein R' is chosen from halos, $C_1$-$C_{10}$ alkyls, $C_1$-$C_{10}$ haloalkyls, $C_1$-$C_{10}$ alkoxys, and $C_1$-$C_{10}$ haloalkoxys.

13. The compound of claim 3, or a pharmaceutically acceptable salt thereof, wherein n is 1 or 2.

14. The compound of claim 3, or a pharmaceutically acceptable salt thereof, wherein each R is independently chosen from halos, optionally substituted $C_1$-$C_{10}$ alkyls, and optionally substituted $C_1$-$C_{10}$ alkoxys.

15. The compound of claim 3, or a pharmaceutically acceptable salt thereof, wherein each R is independently chosen from halos and optionally substituted $C_1$-$C_5$ alkyls.

16. The compound of claim 15, or a pharmaceutically acceptable salt thereof, wherein each R is independently chosen from fluoro, methyl, monofluoromethyl, difluoromethyl, and trifluoromethyl.

17. A compound, or a pharmaceutically acceptable salt thereof, selected from:

N-(2-(2-(difluoromethyl)-5-fluorophenyl)-1H-benzo[d]imidazol-6-yl)-1-methyl-1H-1,2,4-triazole-5-carboxamide;

N-(2-(2-(difluoromethyl)phenyl)-1H-benzo[d]imidazol-6-yl)-1-methyl-1H-1,2,4-triazole-5-carboxamide;

N-(2-(2-(difluoromethyl)-5-fluorophenyl)-1H-benzo[d]imidazol-6-yl)-1-methyl-1H-pyrazole-5-carboxamide;

N-(2-(2-(difluoromethyl)phenyl)-1H-benzo[d]imidazol-6-yl)-1-methyl-1H-pyrazole-5-carboxamide;

1-methyl-N-(2-(2-(trifluoromethyl)phenyl)-1H-benzo[d]imidazol-6-yl)-1H-1,2,4-triazole-5-carboxamide;

1-methyl-N-(2-(o-tolyl)-1H-benzo[d]imidazol-6-yl)-1H-1,2,4-triazole-5-carboxamide;

1-methyl-N-(2-(o-tolyl)-1H-benzo[d]imidazol-6-yl)-1H-pyrazole-5-carboxamide;

1-methyl-N-(2-(2-(trifluoromethyl)phenyl)-1H-benzo[d]imidazol-6-yl)-1H-pyrazole-5-carboxamide; or 1-methyl-N-(2-[2-(trifluoromethyl)phenyl]-4,5,6,7-tetrahydro-1H-1,3-benzodiazol-6-yl)-1H-1,2,4-triazole-5-carboxamide.

18. A pharmaceutical composition comprising a compound of claim 1, or a pharmaceutically acceptable salt thereof, and at least one pharmaceutically acceptable excipient.

19. A method of treating a disease or condition mediated by AhR signaling or associated with aberrant AhR signaling in a subject in need thereof comprising administering to the subject a therapeutically effective amount of a compound of claim 1, or a pharmaceutically acceptable salt thereof, wherein the disease or condition is cancer.

20. A method of inhibiting cancer cell proliferation or tumor cell invasion or metastasis mediated by AhR signaling in a subject in need thereof comprising administering to the subject a therapeutically effective amount of a compound of claim 1, or a pharmaceutically acceptable salt thereof.

* * * * *